(12) United States Patent
Azdoud et al.

(10) Patent No.: US 11,839,734 B2
(45) Date of Patent: Dec. 12, 2023

(54) ROBOTIC TATTOOING SYSTEMS AND RELATED TECHNOLOGIES

(71) Applicant: Blackdot, Inc., Austin, TX (US)

(72) Inventors: Yan Azdoud, Austin, TX (US); Joel Richard Pennington, Austin, TX (US); Eric Nelson Watts, Austin, TX (US); Deniz Ozturk, Philadelphia, PA (US); Anna Ailene Scott, Austin, TX (US); Christopher Daniel Kelley, Georgetown, TX (US)

(73) Assignee: Blackdot, Inc., Austin, TX (US)

( * ) Notice: Subject to any disclaimer, the term of this patent is extended or adjusted under 35 U.S.C. 154(b) by 450 days.

(21) Appl. No.: 17/157,935

(22) Filed: Jan. 25, 2021

(65) Prior Publication Data

US 2021/0386987 A1   Dec. 16, 2021

Related U.S. Application Data

(63) Continuation-in-part of application No. PCT/US2020/043588, filed on Jul. 24, 2020.

(60) Provisional application No. 62/964,579, filed on Jan. 22, 2020, provisional application No. 62/878,673, filed on Jul. 25, 2019.

(51) Int. Cl.
*A61M 37/00* (2006.01)
*A61B 34/30* (2016.01)
(Continued)

(52) U.S. Cl.
CPC ......... *A61M 37/0076* (2013.01); *A61B 34/30* (2016.02); *A61M 37/0084* (2013.01);
(Continued)

(58) Field of Classification Search
CPC ...... A61M 37/0076; A61M 2205/3306; A61M 2205/6063; A61M 2210/04;
(Continued)

(56) References Cited

U.S. PATENT DOCUMENTS

| 2,735,780 A | 2/1956 | Le Compte et al. |
| 3,640,889 A | 2/1972 | Stewart |

(Continued)

FOREIGN PATENT DOCUMENTS

| WO | 2008085758 | 7/2008 |
| WO | WO2015193513 | 12/2015 |

(Continued)

OTHER PUBLICATIONS

ISR, Counterpart PCT Application No. PCT/US2020/043588, filed Jul. 24, 2020, 14 pages.

(Continued)

*Primary Examiner* — Thomas Randazzo
(74) *Attorney, Agent, or Firm* — Perkins Coie LLP

(57) ABSTRACT

An automatic tattoo apparatus can be used to robotically apply tattoos. A customer can shop on an online tattoo marketplace to select designs created by various artists located anywhere. The online tattoo marketplace can process and manage payments, artist and/or customer profiles, bookings, tattoo design uploads, browsing and design selection, design changes, and/or perform other actions. The automatic tattoo device can apply tattoos precisely, quickly, and may with reduced pain. The tattoo apparatus can apply a wide range of different types of tattoos, including but not limited to micro tattoos, dotwork, blackwork tattoos, realism tattoos, fine-line tattoos, etc.

28 Claims, 27 Drawing Sheets

(51) Int. Cl.
  *B25J 9/16* (2006.01)
  *B25J 15/00* (2006.01)
  *G06V 10/22* (2022.01)
  *G05B 19/4155* (2006.01)
  *G06Q 20/12* (2012.01)
  *G06Q 20/38* (2012.01)
  *G06Q 20/40* (2012.01)
  *G06V 10/56* (2022.01)
  *G06V 10/24* (2022.01)

(52) U.S. Cl.
  CPC ........... *B25J 9/1679* (2013.01); *B25J 9/1697* (2013.01); *B25J 15/0019* (2013.01); *G05B 19/4155* (2013.01); *G06Q 20/1235* (2013.01); *G06Q 20/3825* (2013.01); *G06Q 20/40* (2013.01); *G06V 10/225* (2022.01); *G06V 10/56* (2022.01); *A61M 2205/3306* (2013.01); *A61M 2205/6063* (2013.01); *A61M 2210/04* (2013.01); *G05B 2219/50391* (2013.01); *G06V 10/245* (2022.01)

(58) Field of Classification Search
  CPC .... A61M 37/0084; A61B 34/30; A61B 34/25; A61B 2034/2068; A61B 2090/365; A61B 2090/372; A61B 2090/3937; B25J 9/1679; B25J 9/1697; B25J 15/0019; G05B 19/4155; G05B 2219/50391; G06Q 20/1235; G06Q 20/3825; G06Q 20/40; G06V 10/225; G06V 10/56; G06V 10/245; G06N 3/0464; G06N 3/09
  See application file for complete search history.

(56) References Cited

U.S. PATENT DOCUMENTS

| | | | |
|---|---|---|---|
| 3,873,687 A | 3/1975 | Demko | |
| 4,155,886 A | 5/1979 | DeGoler | |
| 4,204,438 A | 5/1980 | Binaris et al. | |
| 4,610,806 A | 9/1986 | Rosen | |
| 4,894,547 A | 1/1990 | Leffell et al. | |
| 5,401,242 A | 3/1995 | Yacowitz | |
| 6,013,122 A | 1/2000 | Klitzman et al. | |
| 6,207,874 B1 | 3/2001 | Felton et al. | |
| 6,208,749 B1 | 3/2001 | Gutkowicz-Krusin et al. | |
| 6,341,831 B1 | 1/2002 | Weber et al. | |
| 6,470,891 B2 | 10/2002 | Carroll | |
| 6,550,356 B1 | 4/2003 | Underwood | |
| 6,800,122 B2 | 10/2004 | Anderson et al. | |
| 6,890,319 B1 | 5/2005 | Crocker | |
| 7,024,033 B2 | 4/2006 | Li et al. | |
| 7,207,242 B1 | 4/2007 | Daigle | |
| 7,344,587 B2 | 3/2008 | Khan et al. | |
| 7,510,603 B2 | 3/2009 | Michel | |
| 7,634,142 B1 | 12/2009 | Bourdev et al. | |
| 7,738,032 B2 | 6/2010 | Kollias et al. | |
| 7,945,302 B2 | 5/2011 | McAdams | |
| 8,036,448 B2 | 10/2011 | Gildenberg | |
| 8,083,422 B1 | 12/2011 | Simmons et al. | |
| 8,090,224 B2 | 1/2012 | Lapstun et al. | |
| 8,189,905 B2 | 5/2012 | Eaton et al. | |
| 8,452,778 B1 | 5/2013 | Song et al. | |
| 8,679,096 B2 | 3/2014 | Farritor et al. | |
| 8,811,680 B2 | 8/2014 | Takiguchi | |
| 8,819,024 B1 | 8/2014 | Toderici et al. | |
| 9,022,949 B2 | 5/2015 | Herndon | |
| 9,087,297 B1 | 7/2015 | Filippova et al. | |
| 9,364,171 B2 | 6/2016 | Harris et al. | |
| 9,445,087 B2 | 9/2016 | Hillebrand et al. | |
| 9,452,281 B2* | 9/2016 | Chan | A61M 37/0076 |
| 9,486,290 B2 | 11/2016 | Zingaretti et al. | |
| 9,505,134 B2 | 11/2016 | Guo et al. | |
| 9,589,190 B2 | 3/2017 | Ramakrishnan et al. | |
| 9,772,270 B2 | 9/2017 | Hyde et al. | |
| 10,052,469 B2 | 8/2018 | Chan et al. | |
| 10,130,260 B2 | 11/2018 | Patwardhan | |
| 10,198,821 B2 | 2/2019 | Hougen et al. | |
| 10,229,322 B2 | 3/2019 | Fridental et al. | |
| 10,455,808 B1 | 10/2019 | Heath et al. | |
| 10,692,220 B2 | 6/2020 | Gao et al. | |
| 10,799,129 B2 | 10/2020 | Shiono et al. | |
| 2002/0110672 A1 | 8/2002 | Muratore-Pallatino | |
| 2003/0095582 A1 | 5/2003 | Ackley | |
| 2004/0146290 A1 | 7/2004 | Kollias et al. | |
| 2004/0267121 A1 | 12/2004 | Sarvazyan et al. | |
| 2005/0172852 A1 | 8/2005 | Anderson et al. | |
| 2005/0234751 A1 | 10/2005 | Ingalls | |
| 2007/0004972 A1 | 1/2007 | Cole et al. | |
| 2007/0006497 A1 | 1/2007 | Alberts | |
| 2007/0032846 A1 | 2/2007 | Ferren et al. | |
| 2007/0060867 A1 | 3/2007 | Xu | |
| 2008/0027279 A1 | 1/2008 | El Kheir | |
| 2008/0033356 A1 | 2/2008 | Kluge et al. | |
| 2008/0039827 A1 | 2/2008 | Ferren et al. | |
| 2008/0078271 A1 | 4/2008 | Atkinson | |
| 2008/0195043 A1 | 8/2008 | Schwach et al. | |
| 2008/0208236 A1 | 8/2008 | Hobbs et al. | |
| 2008/0214987 A1 | 9/2008 | Xu | |
| 2008/0247637 A1 | 10/2008 | Gildenberg | |
| 2008/0273748 A1 | 11/2008 | Meiring et al. | |
| 2008/0300615 A1 | 12/2008 | Colton et al. | |
| 2009/0000513 A1 | 1/2009 | Michel | |
| 2009/0183602 A1 | 7/2009 | Crockett | |
| 2009/0227994 A1 | 9/2009 | Grundfest et al. | |
| 2010/0030111 A1 | 2/2010 | Perriere | |
| 2010/0245823 A1 | 9/2010 | Chhibber et al. | |
| 2011/0148132 A1 | 6/2011 | Park et al. | |
| 2011/0230833 A1 | 9/2011 | Landman et al. | |
| 2011/0242132 A1 | 10/2011 | Bailey et al. | |
| 2011/0246878 A1 | 10/2011 | Dowdell | |
| 2011/0288575 A1* | 11/2011 | Colton | A61M 37/0076 606/185 |
| 2012/0040314 A1 | 2/2012 | Rubino, Jr. | |
| 2012/0192681 A1 | 8/2012 | Klebs et al. | |
| 2012/0300050 A1 | 11/2012 | Korichi et al. | |
| 2013/0046324 A1 | 2/2013 | Williams | |
| 2013/0098265 A1 | 4/2013 | Story et al. | |
| 2013/0278716 A1 | 10/2013 | Kennedy et al. | |
| 2014/0324089 A1 | 10/2014 | Chan et al. | |
| 2016/0030134 A1 | 2/2016 | Shapter et al. | |
| 2016/0067739 A1 | 3/2016 | Jones | |
| 2016/0324586 A1 | 11/2016 | Zingaretti et al. | |
| 2016/0328644 A1 | 11/2016 | Lin et al. | |
| 2017/0259599 A1 | 9/2017 | Shinoda | |
| 2018/0000419 A1* | 1/2018 | Rassman | A61B 5/01 |
| 2018/0147400 A1 | 5/2018 | Brown | |
| 2018/0177992 A1 | 6/2018 | Smith | |
| 2018/0361589 A1 | 12/2018 | Paquin et al. | |
| 2019/0294924 A1 | 9/2019 | Gould et al. | |
| 2020/0311945 A1 | 10/2020 | Lim | |
| 2020/0376855 A1 | 12/2020 | Lee et al. | |
| 2020/0398036 A1* | 12/2020 | Wittendorff | A61M 37/0076 |
| 2021/0060325 A1* | 3/2021 | Xiao | G10L 15/00 |
| 2022/0152371 A1 | 5/2022 | Azdoud et al. | |

FOREIGN PATENT DOCUMENTS

| | | |
|---|---|---|
| WO | WO2016109746 | 7/2016 |
| WO | WO2018073439 | 4/2018 |
| WO | WO2020178818 | 9/2020 |
| WO | WO2021016590 | 1/2021 |

OTHER PUBLICATIONS

Provisional U.S. Appl. No. 62/813,085, filed Mar. 3, 2019, 34 pages.

ISA: United States Patent and Trademark Office, International Search Report and Written Opinion, PCT Patent Application No. PCT/US2022/013691, dated Jun. 6, 2022, 14 pages.

(56) References Cited

OTHER PUBLICATIONS

European Patent Office, European Patent Application No. 20844851.4, Supplemental European Search Report dated Aug. 4, 2023, 12 pages.

* cited by examiner

Digital Representation

Image from Image Capture Device

Machine Vision Algorithm

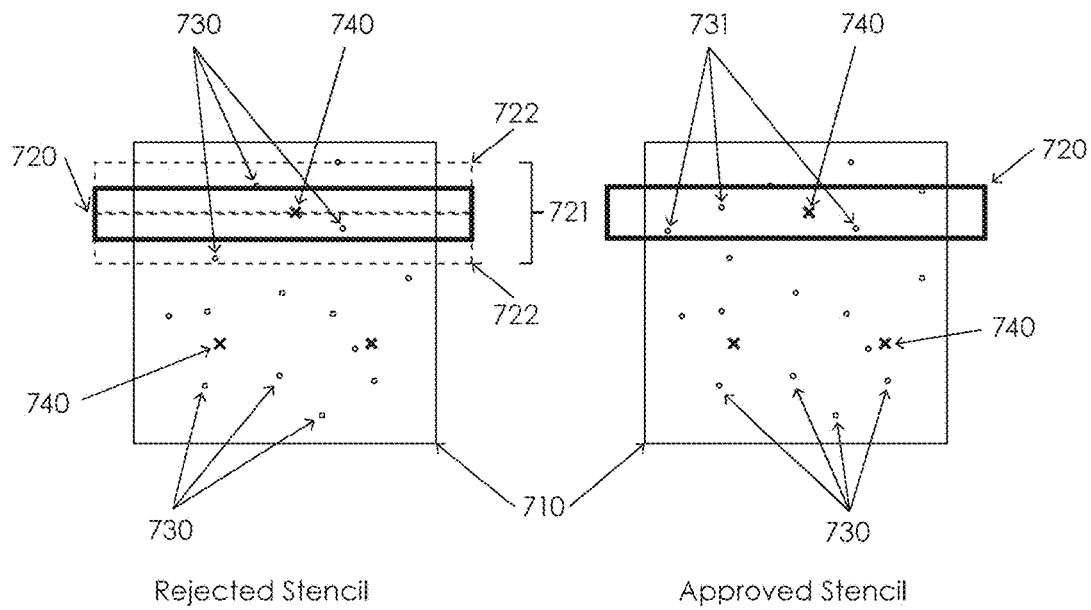
Rejected Stencil
FIG. 11A
Approved Stencil
FIG. 11B
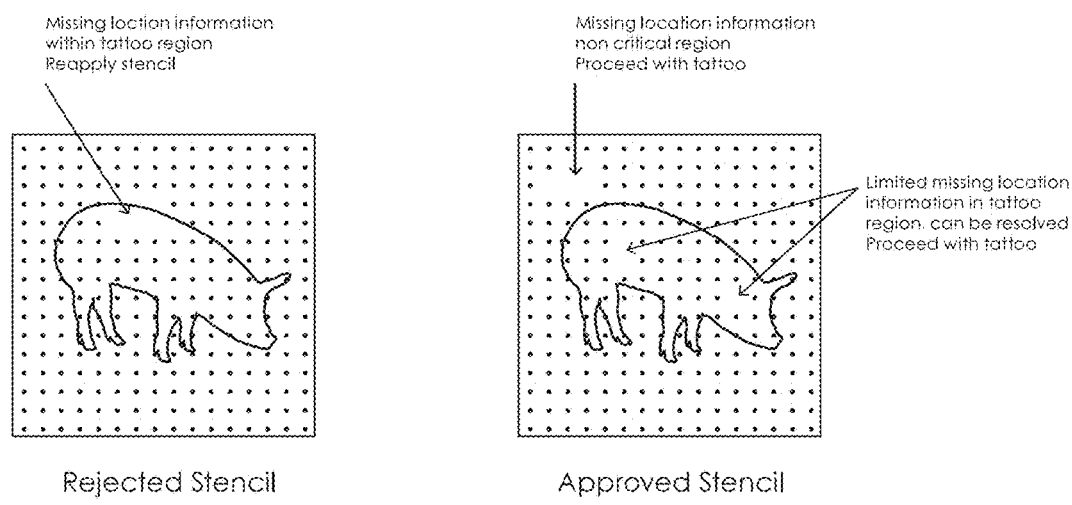
Rejected Stencil
FIG. 11C
Approved Stencil
FIG. 11D

ROBOTIC TATTOOING SYSTEMS AND RELATED TECHNOLOGIES

CROSS-REFERENCE TO RELATED APPLICATIONS

The present application is a continuation-in-part of International Patent Application No. PCT/US2020/043588, which claims priority to and the benefit of U.S. Provisional Application No. 62/878,673, filed Jul. 25, 2019, and U.S. Provisional Application No. 62/964,579 filed Jan. 22, 2020, all of which are hereby incorporated by reference in their entireties for all purposes.

TECHNICAL FIELD

The present disclosure relates generally to systems, devices, and methods for tattooing and applying substances to skin.

BACKGROUND

To apply a tattoo, a tattooing device is held by a tattoo artist while the tattooing device vibrates a needle to inject pigment into the skin. If the injection is too deep, it may have a different hue due to scattering or may look blurred due to subdermal diffusion. If it is too superficial, it may not be held in proper position and may migrate to produce a blurred image or be gradually removed to produce a faded image as the dermis is recycled. Unfortunately, artistic ability varies between tattoo artists, and a particular tattoo artist may be unable to apply visually appealing tattoos. Tattoo artists may develop an expertise applying particular types of tattoos, such as micro tattoos, dotwork, blackwork tattoos, realism tattoos, or fine-line tattoos. An individual may want a tattoo that cannot be produced by a local tattoo artist, so the individual may travel to visit tattoo artists at other locations. In-demand tattoo artists often have exceptional skill that cannot be adequately replicated by other tattoo artists, so they may require booking weeks, months, or years in advance and the tattoos can be expensive. Accordingly, conventional tattooing equipment and techniques have numerous drawbacks.

SUMMARY

In some embodiments, an automatic tattoo apparatus can be used to robotically apply tattoos. A customer can shop on an online tattoo marketplace to select designs created by various artists located anywhere. The online tattoo marketplace can manage payments, artist and/or customer profiles, bookings, tattoo design uploads, browsing and design selection, design changes, and/or perform other actions. The automatic tattoo device can apply tattoos quickly with reduced pain. The tattoo apparatus can apply a wide range of different types of tattoos, including but not limited to micro tattoos, dotwork, blackwork tattoos, realism tattoos, fine-line tattoos, etc.

The online tattoo marketplace can provide an augmented reality shopping experience enabling the customer to see how the tattoo will look at a particular target site on the body. Once a tattoo is selected, the online tattoo marketplace can notify a designated retail location of the purchase. The tattoo marketplace can supply the designated retail location with a token (e.g., a digital token, credit, etc.) or license to apply a tattoo design. An artist can receive payment for the application of the tattoo. The online tattoo marketplace can be used to provide graphics and designs from tattoo artists, non-tattoo artists such as visual artists, artistic celebrities, influencers, brands, artwork provided by customers themselves, or other sources. This allows customers to access artwork irrespective of an artist's physical location. In some embodiments, the artist can receive payment based on royalties, commissions, or other payment schemes. The online tattoo marketplace can include original designs, limited edition designs, resident designs, custom lettering, custom designs, customer provided designs, or other designs. Additionally, the online tattoo marketplace may offer other goods and services including but not limited to tattoo auctions or sale of artwork (e.g., original works and/or prints). After the tattoo apparatus has applied the art, one or more pictures can be supplied to the marketplace, tagged to the artists/studio. The pictures can either be taken by the tattoo machine or by a mobile phone, tablet, or other image capture device of the tattoo recipient, artist, etc.

The automatic tattoo apparatus can communicate with an artist or originator of the graphic and/or design via a network (e.g., a wide area network). A remote server can store the designs/graphics available via the online tattoo marketplace so the tattooing can be performed at any location (e.g., tattoo studio or retail location). For example, tattooing can be performed at retail locations with one or more automatic tattoo apparatuses that can be local and convenient for the customer. Each retail location may additionally provide other goods or services to offer an elevated tattooing experience, such as after-tattoo lotion and sunscreen, bandages, merchandise, etc. An operator of the automatic tattoo apparatus may require less and/or different expertise than a traditional tattoo artist. The automatic tattoo apparatus can apply tattoos visually the same as the originator of the graphic and/or design who can be an in-demand tattoo artists with exceptional skill. Individuals can obtain tattoos of artwork from an artist without having to travel to or book a session with that artist. This allows artwork to be reproduced at a wide range of locations. In some embodiments, the automatic tattoo apparatus is in the form of a tattoo robot capable of applying tattoos. The tattoo robot can include one or more controllers, robotic arms, tattoo needle assemblies, etc.

At least some embodiments can include a tattoo apparatus comprising a tattoo shuttle configured to carry a tattoo needle, at least one sensor configured to measure at least one characteristic of a portion of a customer's skin, a machine vision device positioned to obtain one or more images of the portion of skin, and at least one controller. The controller can be configured to calculate a skin position and/or a skin deformation based on the obtained images and/or sensor signals, and control a puncture depth based at least in part on at least one of the skin position, the skin deformation, or the characteristic(s) of the portion of skin. The needle can be disposable. In some embodiments, the tattoo apparatus can apply tattoos to articles made of natural materials, synthetic materials, or combinations thereof. For example, the tattoos can be applied to belts, clothing, wallets, etc. In some embodiments, the tattoo apparatus is a portable handheld tattooing apparatus with integrated components.

In at least some embodiments, the sensor can be configured to measure information about a puncture operation on the portion of skin. The information can include a load applied to the needle structure during puncture, an acceleration of the needle structure, a speed of the needle structure, a velocity of the needle structure, an angular position of the needle structure, an impedance of contact between the needle structure and skin while in contact with the portion of skin relative to an impedance of the portion of skin alone, and/or an amount of vibration. Accelerometers, gyroscopes, and position sensors can measure the acceleration, rotation, and/or position of the needle or other components. The characteristic(s) of the portion of skin can also include, but is not limited to, a skin elasticity, impedance, and/or thickness (e.g., thickness of the skin, thickness of each layer of the skin, etc.). In some implementations, a force/pressure sensor is used to determine the load and based on displacement output, skin elasticity is determined. Electrical sensors can monitor tissue impedance and based on changes on measured impedance during punctures. Changes in impedance can be correlated to when the needle passes through tissue, at a particular depth, etc. Identification of tissue layers, thicknesses of tissue layers, and other tissue information can be determined based on the output from such sensors.

The controller can be configured to determine a depth of a tissue layer interface based at least in part on a relationship between a force applied to the portion of skin and the depth of the tissue layer interface. Determination of the skin deformation can be based at least in part on an initial deflection of the portion of skin resulting from a force applied to the portion of skin. The controller can be configured to determine characteristics of leather and other materials, whether natural or synthetic.

At least some embodiments can include a tattoo device comprising at least one sensor configured to detect skin puncture events for various needles, at least one characteristic of a portion of skin, or the like. The characteristic can include a depth of a tissue layer interface, and a means for controlling a piercing depth (i.e., puncture depth) based at least in part on the measured characteristic of the portion of skin. In some embodiments, the skin puncture event can relate to one or more of (1) the initial contact with the skin, (2) the initial epidermis failure, (3) where the needle is at the junction of an epidermal and a dermal layer of the skin, (4) where the needle tip is at the junction between a dermal and a hypodermal layer of the skin, (5) where the needle is at its deepest position and/or (6) where the needle exits the skin. The characteristic of the skin can include at least one of a skin elasticity, impedance, or thickness. The characteristics of undeformed or deformed skin can be determined. An optical sensor can be used to determine one or more characteristics of undeformed skin whereas a galvanic sensor or an electrical sensor can be used to determine one or more characteristics of deformed skin. Characteristics of the skin in different states (e.g., deformed state, undeformed state, etc.) can be used to monitor a site before, during, and after application of the tattoo.

In some embodiments, the sensor can be configured to detect the depth of the needle when a puncture event occurs based, at least in part, on a relationship between a force applied to the portion of skin and the depth of the tissue layer interface. The sensor can be further configured to detect a deflection distance or initial deflection of the skin resulting from a force applied to the portion of skin. In some embodiments, the sensor measures the deflection of the skin caused by a needle.

In some embodiments, the sensor can detect the position and/or depth of the needle, when a puncture event occurs, based at least in part on impedance. For example, the sensor can detect the variation of a contact conductivity of the needle against the skin relative to the conductivity of the skin alone. The sensor can be further configured to detect a deflection distance (e.g., initial deflection to puncture) of the skin resulting from a force applied to the portion of skin. In some embodiments, the sensor measures, whether directly or indirectly, the deflection of the skin caused by a needle.

At least some embodiments can include a method for robotic tattooing that includes measuring at least one characteristic of a portion of skin corresponding to a dot position and controlling a piercing depth (i.e., puncture depth) for the dot position based at least in part on the characteristic(s) of the portion of skin. In some embodiments, the dot position can be one of a plurality of dot positions, and the method can be repeated for each dot position. In some embodiments, the dot position can be one of a plurality of dot positions, and the measuring step can be repeated for some of the dot positions. The characteristic of a portion of skin for the remainder of the plurality of dot positions can be determined based at least on interpolation from the measured characteristic of the portion of skin of the measured dot positions. The measured characteristic of the portion of skin can include at least one of a skin elasticity, impedance, or thickness. In some embodiments, the measured characteristic can include one or more mechanical characteristics (e.g., elasticity of tissue, puncture strength, and/or tear strength), electrical characteristics (e.g., impedance), dimensions (e.g., position and/or layer thickness), or the like.

In at least some embodiments, the method can further comprise detecting a position and/or depth of the needle when a puncture event occurs based at least in part on a relationship between a force applied to the portion of skin and the depth of the tissue layer interface. In at least some other embodiments, the method may further comprise detecting a skin deformation of the portion of skin based at least in part on an initial deflection of the portion of skin resulting from a force applied to the portion of skin. The skin can be leather, skin of a living animal (e.g., a human, livestock, etc.), or the like. The method can also be used to apply tattoos to synthetic materials.

The method, in at least some embodiments, can further comprise detecting a position and/or depth of the needle when a puncture event occurs based at least in part on the variation of the contact conductivity of the needle against the skin relative to the conductivity of the skin alone. In some embodiments, the method may further comprise detecting a skin deformation of the portion of skin based at least in part on an initial deflection distance of the portion of skin resulting from a force applied to the portion of skin.

At least some embodiments can include a method for tattooing skin, comprising: acquiring at least one skin puncture property, updating a dot parameter table with a machine setting based on the acquired at least one skin puncture property, and controlling deposit of a substance into the skin based at least in part on the updated dot parameter table. In some embodiments, the method may further comprise applying a stencil (e.g., a stencil with a plurality of dot positions) prior to acquiring the skin puncture property. In some embodiments, the skin puncture property includes a skin deformation measurement. The skin deformation measurement can be based at least in part on an initial deflection of the skin resulting from a force applied to the skin.

The dot parameter table can include a plurality of dot positions and the updating can further include updating a machine setting for each of the plurality of dot positions. In some embodiments, updating the dot parameter table step further comprises determining the machine setting based on interpolation from the skin puncture property. The skin puncture property can include a skin elasticity, impedance, tissue layer depth, tissue layer thickness, and/or layer junction locations.

In at least some embodiments, the method can further comprise detecting a position and/or depth of the needle when a puncture event occurs based at least in part on a relationship between a force applied to the portion of skin and the depth of the tissue layer interface. The deposit of a substance can be controlled based at least in part on the position and/or depth of the needle when the puncture event occurs.

In at least some embodiments the method can further comprise detecting a position and/or depth of the needle when a puncture event occurs based at least in part on the variation of the contact conductance, relative to the conductivity of the skin alone. The deposit of a substance in the skin can be controlled based at least in part on the depth of the needle when a puncture event occurs. In some embodiments, the contact conductivity can be monitored to evaluate changes of the contact conductivity as the puncture depths increases, position of the needle changes, or the like.

At least some embodiments can include methods for managing a marketplace. The method can include providing a user interface illustrating one or more tattoo designs. The method can include receiving a selection of one or more designs and providing the one or more designs to an automatic tattooing apparatus at a retail location in association with a digital token. The automatic tattooing apparatus applies the one or more designs to a tattoo recipient in response to receiving an indication of the digital token. A user can select and receive a tattoo by browsing an online tattoo marketplace, selecting one or more designs, going to a retail location housing an automatic tattooing apparatus, and receiving a tattoo of the one or more selected designs from the automatic tattooing apparatus. The browsing and selecting steps can be performed by different users (e.g., a customer, an artist, or the like) through a mobile application, computer, website, or the like. In other embodiments, the browsing and selecting steps can be performed by a user through a computing device, such as a smartphone, an augmented reality device, a computer. In some embodiments, designs available on the online tattoo marketplace could have been contributed by one or more of an artist, another user, company, or the user. A user can select a tattoo selection tool via an online tattoo marketplace, at the retail location, or any other suitable location. In some embodiments, the user can use the computing device to preview the location and the design of the selected tattoo. For example, the user can use augmented reality to view the location of the tattoo on his or her body. The user can then accept the location or reposition that tattoo. The tattoo system can lock the tattoo location based on the user's acceptance.

The tattoo design can be rendered on an image of a portion of the skin or on the skin itself. In some embodiments, a light projecting device can render a tattoo design on the skin. In some embodiments, an image is visualized on the skin using a real time feed from an augmented reality apparatus, such as a smart phone, a smart TV, AR googles, a smart mirror, a computer, or any user device containing a camera for real time feed and a screen or lenses for visualization of augmented reality images. A method for altering the positioning and scaling of a tattoo design rendering can be based on user input.

An artist who created at least one of the selected designs can receive payment for each created design that was received as a tattoo. In some embodiments, the retail location can be a location remote from an artist who created the design. The artist can receive information about alterations to tattoo designs to help the artist generate new tattoo designs.

At least some embodiments are directed to an automated apparatus configured to analyze a site and to puncture a subject's skin at the site. The analysis can include, without limitation, one or more optical analyses, electrical analyses, mechanical analyses, chemical analyses, or combinations thereof. The apparatus can puncture the subject skin to apply one or more liquids, medications, substances, or combinations thereof. In some embodiments, the apparatus can perform multiple analyses to perform a task, such as applying one or more tattoos. The apparatus can perform analyses to position a piercing element (e.g., a needle, needle array, etc.) for injecting a fluid (e.g., liquid ink, pigment, dyes, etc.) into one or more layers of skin or other tissue. The apparatus can be used in tattooing applications, medical applications, aesthetic applications, or other suitable uses.

In tattooing applications, a temporary pigment can be injected into the epidermal layer to provide a reference feature (e.g., a temporary dot). A permanent pigment can be injected into the dermal or other layer using the reference feature. The subject's body can naturally cause the reference feature to break down and be absorbed into the subject's body leaving only the permanent features (e.g., tattoo dots). An optical analysis can include using machine vision or computer vision to identify reference features (e.g., applied and/or natural fiducials), landmarks, stenciling, applied dots (e.g., previously applied dots when applying the tattoo), skin features (e.g., moles, scars, hair, etc.), or the like. The apparatus can be programmed to identify such features and determine one or more of the following: position of stenciling, tattoo placement, puncture sites (e.g., interrogation sites), volume of ink to be applied at each puncture site, depth of puncture site, needle characteristics, and/or position information. If the subject's body part moves during a session, the apparatus can identify the movement and determine an appropriate protocol for continuing one or more tasks based on the new body position. This allows a tattoo to be robotically applied without disrupting the session. The apparatus can apply a wide range of substances, including fluids, gels, or other suitable substances. For example, during or after the session, the apparatus can inject one or more medicants, analgesics, pigment enhancing agents, antibacterial agents, or other substances in the dermal and/or epidermal layers to, for example, reduce discomfort, promote healing, inhibit infection, or combinations thereof. In a following session (e.g., a session days, weeks, or months after a tattoo is applied), the automated apparatus can analyze the tattoo and identify areas to be modified by, for example, reapplying dots, touching up dots, etc. Images of the applied tattoo can be compared to a virtual tattoo to identify the areas to be modified.

In non-tattoo applications, the apparatus can apply botulinum toxin (e.g., Botox®), anti-wrinkle agents, denervating agents, anti-acne agents, collagen, or the like. The apparatus can optically analyze a site and identify wrinkles (using a trained computer vision system similar to that described below). Targeted wrinkles can be located along the subject face (e.g., along the forehead, surrounding the eyes, etc.) or any other location. The apparatus can determine one or more puncture sites based on characteristics (e.g., size, depth, location, etc.) of the wrinkles. The apparatus can inject one or more anti-wrinkle agents at puncture sites to reduce or limit the appearance of the targeted wrinkles.

The apparatus can include one or more machine vision systems configured for imaging-based automatic inspection and analysis. The machine vision systems can be configured for one-dimensional, two-dimensional, or three-dimensional analysis and can include one or more image capture devices, such as digital cameras. The machine vision system can analyze non-planar surfaces, planar or flat surfaces, optically identifiable features, and other features. The non-planar surfaces can include, without limitation, curved surfaces (e.g., highly-contoured regions of skin), undulating surfaces, or the like. The flat surfaces can be generally flat areas of tissue. A frame can be pressed against the subject's tissue to flatten the site. The optically identifiable features can include, without limitation, dots, tattoos (e.g., portions of tattoos, entire tattoos, etc.), stenciling (e.g., dots, patterns of dots, etc.), body parts, or the like. In some embodiments, the machine vision systems can be configured to perform, without limitation, one or more line scans, area scans, triangulation data collection (e.g., 3D images suitable for triangulation), etc. The machine vision systems can capture images and generate one or more maps based on the captured images. For example, captured images can be combined to generate multi-dimensional maps (e.g., two-dimensional maps, three-dimensional maps, etc.), or the like. In some implementations, such a computer vision system can use a machine learning model or other suitable analytical models trained to identify desired features (e.g., skin landmarks, stenciling, applied tattoo dots, wrinkles, moles, scars, hair, etc.). For example, a neural network can be trained to identify such features with supervised learning, applying training items comprising images with parts tagged as having or not having these features. The training data can be based on human tagged images, medial databases, etc. In various implementations, different types of neural networks (e.g., deep neural networks, convolutional neural networks, etc.) can be used or other types of machine learning models (e.g., decision trees, support vector machines, etc.) can be used. Further, different types of training can be applied (e.g., supervised, unsupervised, applying different types of loss or activation functions, etc.).

In some embodiments, the apparatus can include one or more cameras, sensors (e.g., 2D or 3D sensors such as laser-displacement sensors, imaging sensors, calibration sensors, etc.) for outputting data for inspection, feature identification, surface topology, area evaluation, volume measurement, or the like. The output from the sensors can be used to produce, without limitation, images (e.g., digital images), maps of target sites, height maps (e.g., height maps generated from displacement of reflected lasers), or the like.

In some embodiments, a system can be used to analyze one or more interrogation sites to determine at least in part how to apply a tattoo or a portion thereof. The interrogation sites can be punctured to determine skin characteristics, including number of skin layers within a certain depth, dimensions of skin layers, characteristics of skin layers (e.g., elasticity, puncture characteristics, etc.), or the like. Puncture sites can be the same as or different from the interrogation sites. Puncture sites suitable for receiving dye can be selected based on, for example, target site characteristics, the tattoo design to be applied, stencils, etc. During the tattooing process, a tattoo site can be periodically or continuously analyzed to adaptively adjust the application of the tattoo to enhance application by, for example, compensating for, without limitation, skin stretch, appearances of applied dots, body part movement, or the like.

Establishing skin position may not be sufficient to execute an accurate rendition of the tattoo. This is because skin is rarely in its relaxed, non-stretched or undeformed state during tattooing. When a tattoo is applied to deformed skin, the tattoo may look stretched or contracted when the skin is relaxed. This may result in a less accurate tattoo application, because skin is constantly stretched or deformed based on the position of the body part being tattooed. In order to perform an accurate rendition (e.g., a non-distorted rendition of a reference tattoo design), the system can measure deformation of the skin and apply a compensation of the positioning.

The system can periodically or constantly compensate for the position and deformation of the portion of the skin to identify the appropriate location of the applied ink. In-plane skin deformation is a field of displacement associated with the surface of the skin as the skin stretches, contracts, and/or rotates. The skin deformation is null when the skin is in its relaxed state. The skin can have a non-null deformation when force is applied to it (e.g., when an object pushes against the skin, skin is stretched by natural movement of the body, etc.). If deformation is not compensated for, the applied tattoo may look deformed or distorted when the skin is relaxed. In some embodiments, skin deformation is compensated for by analyzing skin fiducials in different states (e.g., an undeformed state, deformed state, etc.). This is done by, for example, (i) scanning/analyzing the skin in an undeformed state to identify fiducials in an undeformed state using machine vision and/or (ii) applying a stencil (e.g., containing a known pattern of fiducials) on the skin while the skin is in an undeformed relaxed state of the skin and tracking the stencil with machine vision during the tattoo session. Deformation is tracked as the displacement field from the undeformed state of the skin to the state of the skin in the configuration in which the tattoo is performed.

In general, compensating for skin changes during tattooing can be important because skin is not in its undeformed state. Tracking fiducials during the tattooing process alone may not account for the deformation occurring between the relaxed state of the skin and the potentially deformed state. Image analyses can analyze skin over a period of time to determine how to compensate for skin deformation. In some embodiments, a machine vision method analyzes one or more images collected during tattooing and compares it to the undeformed, relaxed skin analysis. The skin deformation compensation can be performed by applying the same deformation to the portion of the tattoo design being applied in order to have an undeformed result when the skin is at rest (e.g., undeformed or in a natural state).

The tattoo systems can include a frame used to grossly maintain or immobilize a part of the body containing the portion of the skin to be tattooed. The frame can be configured to securely hold the body part. In some embodiments, the tattoo system includes a contactor which maintains or immobilizes a portion of the skin to be tattooed. The contactor can stabilize the skin distance to a needle head. The contactor can inhibit, limit, or prevent run-off liquids. The contactor can also integrate a movement detection apparatus or a suction system, and can position, hold, and/or flatten the skin to be tattooed.

A tattoo system can include cleaning an area by, for example, removing excess fluids using a suction system. Nozzle geometry, angle of attack, and suction nozzle position can be selected to improve suction of target substances (e.g., liquids) only. The suction system can provide suction near to or at the edge of a contactor. In some embodiments, a cleaning system includes one or more suction systems, lubricant and contactor heads. The lubricant can serve as a barrier to protect against stains due to excess fluids. The lubricant can facilitate sliding of the contactor along the skin. The contactor can be configured to inhibit or prevent runoff of excess fluids. The system can be configured to determine when cleaning procedures should be performed.

A method of tattooing includes pausing a tattooing operation and evaluating a new position if a movement is detected. In some embodiments, machine vision is used to detect movement of skin. In some embodiments, an optical sensor on a portion of skin that is not being tattooed detects movement. In some embodiments, one or more non-optical sensors, such as accelerometer or vibration sensors, detect the movement. The number, position, and functionality of the sensors can be selected based on desired movement detection, skin position, needle position/movement, etc. In some embodiments, a robotic tattooing system can detect movement of a tattoo site or body part. The detected movement can be analyzed to determine whether to adjust the tattooing protocol. The tattooing protocol can be adjusted to compensate for the movement. For example, a frame of reference of the tattooing protocol can be adjusted to match the detected movement of the body part. Additionally or alternatively, the detected movement can be movement of the needle, contactor, or another component of the robotic tattooing system. Different types of movement can be analyzed to control the tattooing process.

In some embodiments, a tattoo system comprises a gross positioning actuator and a camera or machine visions system. The gross positioning actuator and camera can be used to position a tattoo head in contact against a body part. The gross positioning actuator and camera can be used to localize and position the tattoo needle with respect to the portion of the skin to be tattooed. The tattoo system can perform a one-stage or multi-stage tattooing process.

At least some systems disclosed herein can use natural or artificial features or patterns for positioning. At least some robotic systems can identify natural or artificial patterns for skin deformation identification. One or more pattern-detection algorithms can be used to identify fiducials (applied or natural fiducials), patterns (whether natural or artificial patterns), skin changes, or other features of interest based on output from one or more machine vision systems. In further embodiments, a tattooing system can include one or more disposable or reusable ink containers. The tattooing system can include a pump or refilling system for replenishing ink by, for example, replacing or refilling the ink containers. The ink containers can be refilled when the ink is at a low level or at a rate commensurate to the number of punctures performed.

The robotic systems disclosed herein can generate a digital representation of a selected tattoo design. Puncture settings can be selected for individual puncture sites, a group of puncture sites, or the entire tattoo. In some embodiments, puncture settings are individually determined for each puncture site for producing a dot. This allows for precise control of the appearance of each dot. In certain embodiments, the number of punctures per site can be controlled by the user by, for example, inputting maximum and minimum number of punctures per site. Other user inputs can be used to define ranges for parameters disclosed herein. During tattooing, the system can periodically or continuously analyze applied punctures to modify or select puncture settings for dots to be applied. This allows for adaptive control of the tattooing process. For example, if the robotic system identifies an abnormal region of tissue, the robotic system can compensate for variations in skin characteristics to produce dots having a target appearance. Dots with desired appearances can be formed at sites with varying tissue properties (e.g., sites with scar tissue, sites with a thicker or thinner epidermal layer, etc.), visual characteristics, or the like.

BRIEF DESCRIPTION OF THE DRAWINGS

FIGS. 11A and 11B are illustrative diagrams of an example rejection and example approval of a stencil position, respectively, in accordance with an embodiment of the disclosure.

FIGS. 11C and 11D are simplified illustrative diagrams of an example rejected stencil and an example approved stencil, respectively, in accordance with an embodiment of the disclosure.

DETAILED DESCRIPTION

Tattooing Environment and Systems

Figure 1A:
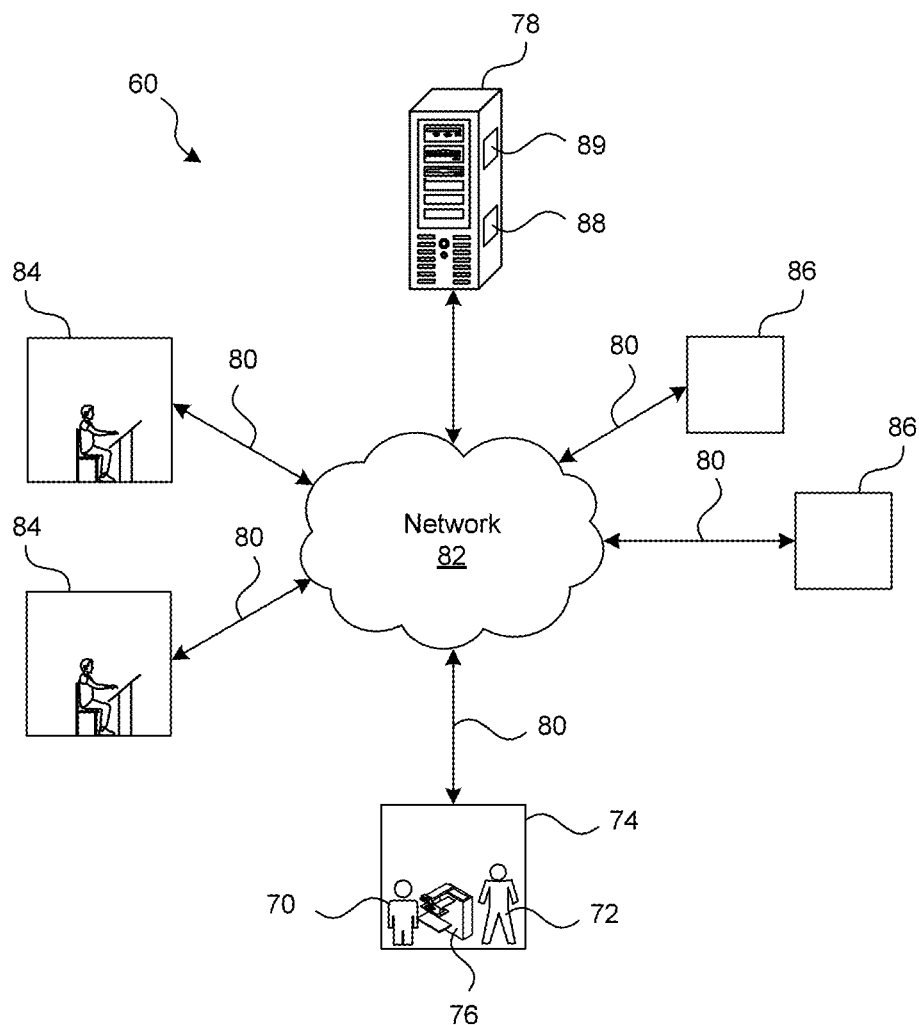
FIG. 1A is a network diagram of a tattooing environment and system in accordance with an embodiment of the disclosure.

FIG. 1A is a network diagram of a tattooing environment and system 60 in accordance with an embodiment of the disclosure. A client or subject 70 ("subject 70") and operator 72 can be located at a tattoo studio 74. The tattoo studio 74 can include one or more automated tattooing systems 76 configured to apply a tattoo based on artwork selected by the subject 70. The operator 72 can prepare the tattoo site and operate the automated tattooing system 76.

A tattoo assistance system 78 can include, without limitation, one or more computing devices and/or system and can provide data used by the automated tattooing systems 76. The tattoo assistance system 78 can perform one or more steps of a tattooing process, such as generating calibration protocols, determining skin puncture properties, generating tables (e.g., dot parameter tables, puncture data, etc.), processing images, generating stenciling, generating tattooing protocols, or the like. The tattoo assistance system 78 can include, for example, one or more servers, processors, and memory storing instructions executable by the one or more processors to perform the methods described herein. In some embodiments, the server implemented can be a distributed "cloud" computing system or facility across any suitable combination of hardware and/or virtual computing resources. The tattoo assistance system 78 can communicate with the automated tattooing systems 76, network 82, and other systems through communication channels 80.

The network 82 can be in communication with artwork providers 84 and users/clients 86. The artwork providers 84 can be artists that upload tattoo artwork to an online tattoo marketplace. In one embodiment, the online tattoo marketplace may be a global online tattoo marketplace where artwork providers 84 may upload, license, and/or sell their designs irrespective of their physical location. Artists may be paid a royalty based on selection and/or licensing of their designs by subjects through the app and/or website. The tattoo assistance system 78 can provide or support a user interface illustrating one or more tattoo designs. The tattoo assistance system 78 can receive a selection of one or more design and provide the one or more designs to an automated tattooing system 76 with a digital token. The automated tattooing systems can use one or more designs to a tattoo recipient (e.g., subject 70 in FIG. 1A) in response to receiving an indication of the digital token. The tattoo assistance system 78 can include features and functionality discussed in connection with FIGS. 20 and 21 and perform one or more of the steps (e.g., all of the steps) of algorithms discussed in connection with FIGS. 3A-7, 9, 12A-13, 17, and 19.

The subject 70 can purchase a tattoo from one of the artwork providers 84 who may be located at a remote location. The subject 70 can obtain artwork for generating a high-quality tattoo that appears similar to original artwork provided by the artist. The tattoo system 76 can reproduce artwork more consistently than a human tattoo artist. Accordingly, individuals across the world can purchase artwork form an artist and receive a tattoo of the artwork without requiring that the individual travel to the artist. The tattoo system 76 can replicate tattoos from an in-demand tattoo artist without requiring booking with that artist, thereby reducing the time to receive the tattoo and costs. Additionally, the tattoo system 76 can apply, for example, micro tattoos, dotwork, blackwork tattoos, realism tattoos, and/or fine-line tattoos. Tattoos can be applied based on artwork from individuals located throughout the world. The tattoo system 76 can include one or more robotic arms (e.g., multi-axis arms, etc.), linear actuators, rails, motors, gantries, controllers, and other suitable components for manipulating and positioning needles to produce the tattoo.

The tattoo assistance system 78 can include at least one database 88 and module 89. The database 88 can be configured to store artwork, protocols, tattoo data, skin data, stencil data, client data, or the like. The module 89 can be configured with one or more algorithms for performing processes disclosed herein and discussed in connection with FIGS. 3A-7, 9, 11A-13, and 17-18. Some or all of the functionality described herein with respect to the module 89 may also be performed by the tattoo systems/apparatuses, and vice-versa. The module 89 can also include some or all of the functionality and features described herein with respect to the controller of FIG. 20 or other controllers disclosed herein. A remote server of the module 89 can store the designs/graphics available via the online tattoo marketplace so the tattooing can be performed at any location (e.g., tattoo studio or retail location). For example, tattooing can be performed at retail locations with one or more automatic tattoo apparatuses that can be local and convenient for the customer. In some embodiments, the tattoo assistance system 78 can communicate with an artist or originator of the graphic and/or design via the network 82 (e.g., a wide area network).

The subject 70 and users/clients 86 can use a user device to select artwork, purchase tattoos, input preferences, submit payment, manage credits/tokens, or the like. Browsing and selection of artwork may be done via a mobile app and/or website that allows access to the online tattoo marketplace, through which subjects may perform actions including, but not limited to, browsing, selecting, saving, rating designs, uploading, creating a profile, booking appointments, participating in auctions, or buying. In one embodiment, the online tattoo marketplace may be a global online tattoo marketplace where artists or users may upload, license, and/or sell their designs irrespective of their physical location. Artists may be paid a royalty based on selection and/or licensing of their designs by subjects through the app and/or website. Browsing, selection, and payment process may vary by location, as well as by individual artists. Exemplary user devices include, without limitation, a personal computer (PC), a laptop, a tablet computer, or a smartphone. Generally, the user device can include a display and/or one or more processors. The displays can offer the user a visual interface for interaction with the system, as discussed in connection with FIG. 9 (e.g., user device 509 of FIG. 9). The tattoo studio 74 can have different robotic tattooing machines disclosed herein for producing a wide range of different types of tattoos to the subject 70.

Figure 1B:
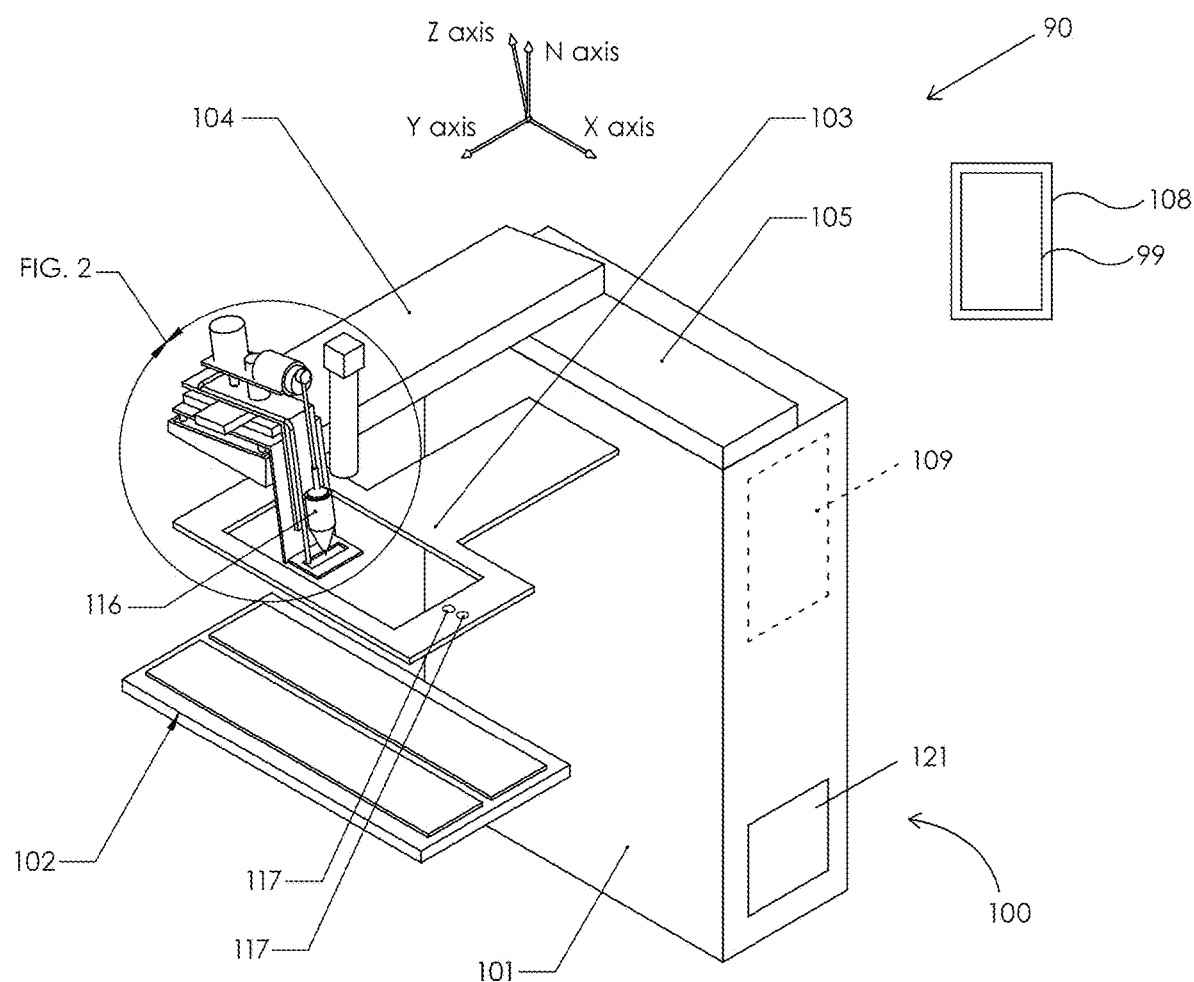
FIG. 1B is a schematic isometric view of a tattooing system in accordance with an embodiment of the disclosure.

FIG. 1B is a schematic isometric view of a tattooing system 90 in accordance with an embodiment of the disclosure. The tattooing system 90 is suitable for use in the environment of FIG. 1A and can include a tattooing apparatus 100 and at least one controller 108. The tattooing system 90 can determine a tattoo protocol or receive a tattoo protocol based on a target tattoo site on the subject. The tattooing apparatus 100 can apply the selected tattoo based on the tattoo protocol. During the tattoo session, the subject's body part can rest on a rest surface 102.

The tattooing apparatus 100 can include a cantilevered tattoo machine 101 ("tattoo machine 101"), a tattoo frame 103, and a tattoo shuttle 104 configured to carry a tattoo needle. The tattoo machine 101 can move the tattoo shuttle 104 while the tattoo frame 103 is against the target tattoo site. The tattooing apparatus 100 can also include one or more sensors 116 and at least one controller 109. The sensors 116 can be carried by the shuttle 104 and/or a component of the shuttle 104 and configured to measure at least one characteristic of a subject's skin. The tattooing process can be controlled based at least in part on the measured characteristic(s) of the portion of skin, such as skin elasticity, impedance, or thickness (including thicknesses of one or more skin layers).

The cantilevered tattoo machine 101 can be a structural element connected to the tattoo shop floor, which holds the rest surface 102, the tattoo frame 103, and the tattoo shuttle 104. The cantilevered tattoo machine 101 can be configured to provide structural support and stability to the tattooing system 90 and its components. In some embodiments, the cantilevered tattoo machine 101 can include motors (e.g., drive motors, stepper motors, etc.), robotic arms (e.g., multi-axis arms), gantry devices, linear slides, rails, sensors (e.g., position sensors, accelerometers, etc.), motors, rails, or the like.

With continued reference to FIG. 1B, the tattooing apparatus 100 can be actuated through a cantilevered X gantry 105 along an axis, illustrated as an X axis. The X gantry 105 may be a mechanical gantry that moves on the X axis and connects the tattoo shuttle 104 to the cantilevered tattoo machine 101. A Y axis may be orthogonal to the X axis in a plane of the tattoo frame 103. An N axis may be normal to a plane formed by the X and Y axes. A Z axis may be formed with a degree of inclination relative to the N axis. In one embodiment, the Z axis is not orthogonal to the plane formed by the X and Y axes. For example, the Z axis may have a 10 degree, 15 degree, or 20 degree inclination to the XY normal (N axis) in the XZ plane, and 0-degrees in the YZ plane. In another example, the Z axis may have more or less than a 15-degree inclination in the XZ plane, and more or less than about 0-degrees in the YZ plane. In another embodiment, the Z axis is orthogonal to the plane formed by the X and Y axes.

Figure 2:
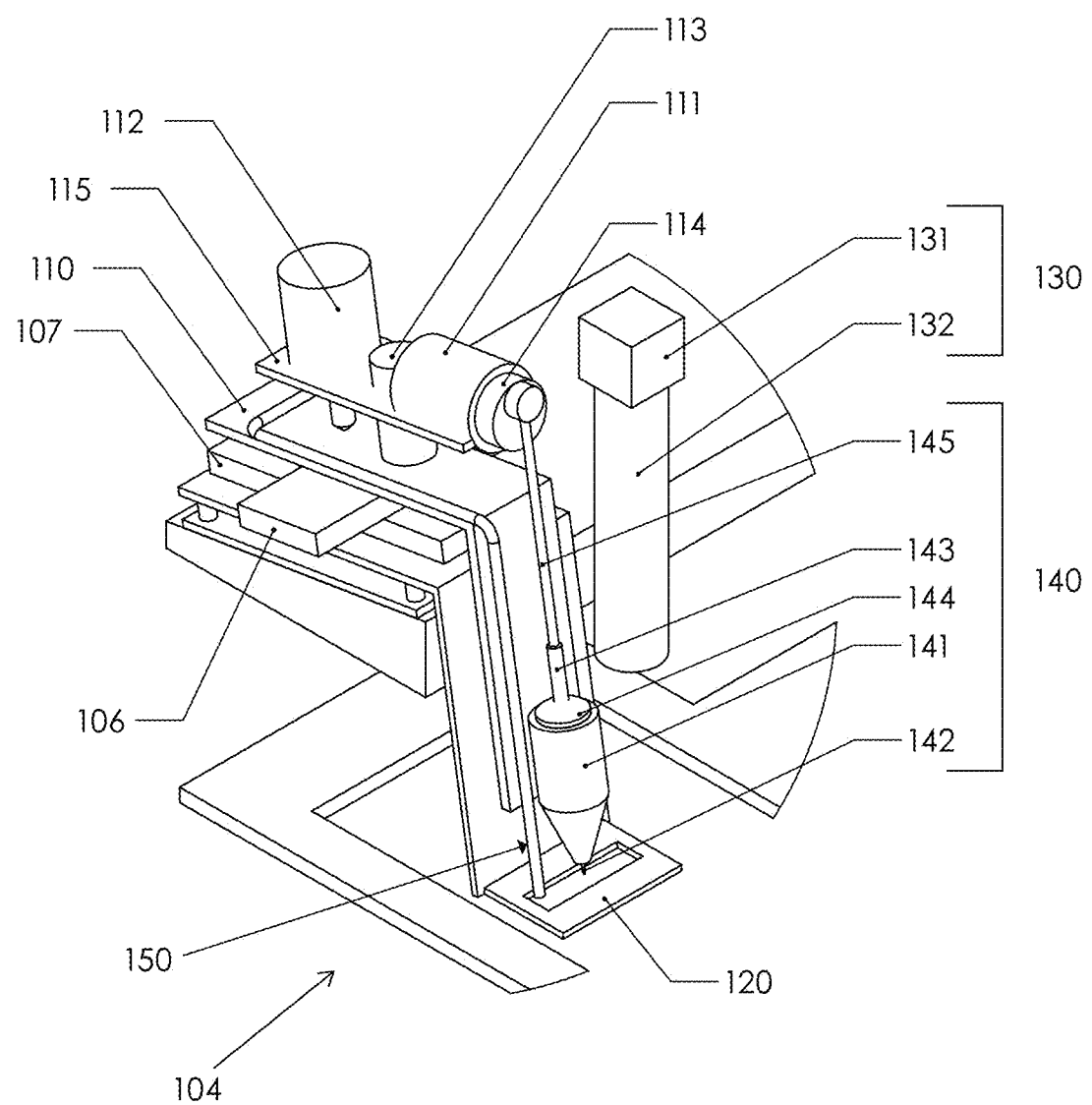
FIG. 2 is a schematic isometric view of a tattoo shuttle of the tattooing system of FIG. 1B in accordance with an embodiment of the disclosure.

The rest surface 102 can be a pad with a set of inflatable bladders or pneumatic actuator for precise alignment of a body part to be tattooed. For example, the pneumatic actuator may be configured to maintain a tattoo area of the body in contact with the tattoo frame 103, while applying low enough pressure as to not interrupt blood perfusion of the body part. The rest surface 102 may be configured to orient the body part to be tattooed in a relaxed position for the subject. The pad of the rest surface 102 may vary in size, shape, and configuration. For example, the pad may be larger or smaller than the tattoo frame 103. In a particular embodiment, the pad may be larger than the largest tattoo frame 103. In another example, the pad may comprise of multiple segments and/or shapes. The rest surface 102 can be raised or lowered so that its height is capable of being set manually, or automatically, with n degrees of freedom. For example, rest surface height can be set with 3+1 degrees of freedom. In another embodiment rest surface height can have more or less than 3+1 degrees of freedom. The rest surface 102 can be rotated manually and/or set monobloc with the cantilevered tattoo machine 101. In some embodiments, the pad 102 may not be actuated or necessary and the tattoo machine 100 may be positioned to apply the appropriate contact force to the body part regardless of its orientation and rest surface, such that the contactor 120 of FIG. 2 is in contact with the area to be tattooed and/or for the frame 103 to hold the body part of interest in place.

The tattoo frame 103 may be a flat frame surface in contact with the skin to isolate the area where the tattoo is to be applied. The tattoo frame 103 may be fixed in the YN direction and all rotations with respect to the tattoo shuttle 104, and/or also fixed with respect to the cantilevered tattoo machine 101. The tattoo frame 103 may comprise a variety of shapes and sizes. In one embodiment, the tattoo frame 103 can be generally rectangular with a window (e.g., a polygonal window, rectangular window, etc.) to isolate the area of skin where the tattoo is to be applied. In other embodiments, the tattoo frame may be, for example, circular, ovular, or any other shape. The tattoo frame 103 may be equal to, larger, or smaller than the rest surface 102. The size and shape of the tattoo frame 103 can generally correspond to an area of the body to be tattooed. For example, in one embodiment, an appropriate tattoo frame 103 may generally match the size of the area of the body to be tattooed. In some embodiments, the tattoo frame 103 size may be between about 20×20 mm to about 100×300 mm. Additionally, the tattooing apparatus 100 may have a plurality of tattoo frames 103 that maintain contact with the skin and expose a tattoo zone. In some embodiments, tattooing apparatus 100 may utilize one or more tattoo frames 103 that are interchangeable and chosen based on the desired tattoo. The tattoo zone can be rotated and repositioned to match a location of the tattoo. In some embodiments, the tattoo frame 103 can be omitted and other means can be employed to hold the body part of interest in place and/or at least detect movement of the body part of interest before, during, and/or after the tattooing process.

The contactor 102 and/or tattoo frame 103 (or other component of the tattoo apparatus 100) disclosed herein can help maintain or immobilize the body part while the contactor 102 maintains a desired distance (e.g., a constant distance, a distance within a range, distance from the skin to the tattoo needle, etc.). If the client twitches or moves the body part being tattooed, the tattoo frame 103 can provide enough resistance to limit or avoid accidental gross movement. On the other hand, the contactor force applied to the skin allows for compensation of small movement of the skin in the vicinity of the contactor 102. For example, if the body part moves by a small amount, and because of the skin friction against the contactor 102 and the inherent elasticity of skin, the portion of skin in the window of the contactor can remain generally static with respect to the contactor. The contactor role in this example is for maintaining the skin in place. Another role of the contactor 102 can be to maintain skin height position. The skin can remain in contact with the contactor window edge during tattooing. As a result, the distance from the needle to the skin can be known within a precision equal to or lower than 0.1 millimeter, 0.3 millimeters, 0.5 millimeters, 1 millimeters, or 2 millimeters, or other suitable distances. The skin may only deform a small amount within the window and can be easily compensated for by varying the needle extension and by using, for example, a galvanic sensing system, one or more position sensors, and/or one or more range-finding sensors. Additionally or alternatively, the contactor 102 can apply a shear force to the skin when moving from position to position, which may stretch the skin. The stretched skin can have more uniform properties than relaxed skin. For example, when the contactor 102 slides across the skin, the skin may be stretched due to the friction between the contactor 102 and the skin. The system can include one or more sensors capable of detecting applied forces (shear forces, compressive forces, etc.), skin stretching, skin movement, etc.

The contactor 102 can serve as a barrier against the skin to prevent runoff of liquids, such as lubricant, bodily fluids, and injected substances, such as ink. For example, during a puncture, excess ink may accumulate in the contactor window. If the contactor 102 is firmly pressed on the skin, ink may not escape the contactor window. The collected ink can be controllable from the contactor window. The contactor systems described herein may be used without tattoo frames. In some embodiments, the contactor system may be pressed against the body part by a robotic arm or gantry system, controlled by the application of an appropriate range of force (0.1-50 N) and/or displacement (0-10 cm) against the skin. Independent of the method of maintaining contact with the body surface, the contactor system may (i) stabilize skin distance, (ii) prevent runoff liquids, (iii) house an integrated suction system in contact with the skin surface, and/or (iv) house integrated movement detection sensors for safety. For example, in one embodiment, the contactor system may be attached to the end of a robotic arm, in order to maintain a stable skin distance that is fixed relative to the tattooing head, upon approaching and landing on a desired part of the body.

The controller 108 can be a computing device with one or more displays for displaying artwork, tattoo designs, stenciling, tattoo needle paths, tattoo session information (e.g., length of session, costs, color of inks to be applied, etc.), and/or visualization of artwork to be applied. In some embodiments, a display 99 can provide visualization of artwork selected by the client. The client can input location information such that the system virtually applies the tattoo using augmented reality or other visualization techniques. A user can specify a location by overlaying an image of the design on an image of their skin (e.g., via a live feed from their camera, a previously captured image, etc.). The system can then use computer vision techniques to identify position and orientation of the design in relation to, for example, the body party and/or one or more skin features, such as existing tattoos, moles, hairs, wrinkles, blemishes, etc. The position and orientation of the design, in relation to these skin features, can then be stored (e.g., stored by controllers 108 and/or 109), allowing the tattooing system 90 to recognize these skin features and apply the selected design with the same position and orientation characteristics.

If a color tattoo will be applied, the tattooing system 90 can automatically select recommended colors based on the tattoo design, skin characteristics (e.g., skin color, skin tone, etc.), and/or other tattoo parameters. For example, the tattooing system 90 can have a pre-determined mapping of skin characteristics to preferred or undesirable tattoo characteristics that it can use to make suggestions when a user identified to have such a skin characteristic selects a design with undesirable tattoo characteristics or without preferred tattoo characteristics. In some implementations, this mapping can include corrective measures, such as a change in color or tattoo position when such a suggestion is made. The client and/or operator can select the size the tattoo, color the tattoo, place in the tattoo, and/or parameters based on the displayed information. The display 99 can be a touchscreen to enable convenient input. Additional details of selecting, viewing designs, and input information about tattoos are discussed in connection with FIG. 9. A stencil can be applied to the customer to review the design's positioning on the skin before starting the tattooing operation. Positioning of the design and/or stencil may also be reviewed using augmented reality. In some embodiments, a final tattoo design can be overlaid on a camera image or live video, based on the positioning and deformation of the applied stencil on the image detected by machine vision.

Referring to FIG. 1B, a container 121 can be fluidically coupled to a needle structure (e.g., needle structure 140 of FIG. 2). The tattooing apparatus 100 (FIG. 1B) can include a fluidic system having one or more lines (e.g., hoses, multi-lumen conduits, etc.), pumps (e.g., peristaltic pumps, diaphragm, piston or centrifugal pumps, piezoelectric pumps, etc.), valves, manifolds, filters, sensors (e.g., pressure sensors, flow sensors, etc.), and other fluidic components. The container 121 can be a bottle, cartridge, or other container suitable for holding fluid. In some embodiments, the tattooing apparatus 100 is configured to hold multiple containers to apply color tattoos, avoiding downtown for replenishing fluid, or the like. The number of containers, volume of the containers, and configuration of the fluidic system can be selected based on the desired system functionality. The tattooing system 90 can include any number of pumping mechanisms, such as peristaltic pumps, diaphragm, piston or centrifugal pumping, piezoelectric pumping, capillary effects and so on. The configuration of the pumping mechanisms can be selected to provide the desired volume of ink to the needle tip when the tattoo is performed while not overflowing the needle reservoir.

FIG. 2 is a schematic isometric view of an embodiment of the tattoo shuttle 104 of the tattooing apparatus 100. The tattoo shuttle 104 can include an arm 110, a contactor 120, a target site analyzer or machine vision device 130 ("machine vision device 130"), and a needle structure 140. The X gantry 105 can connect the tattoo shuttle 104 to the cantilevered tattoo machine 101. In some embodiments, the tattoo shuttle 104 can slide relative to the cantilevered tattoo machine 101 on the N axis. The sliding relation may be provided by one or more spring mechanisms, linear slides, rail systems, or the like. The arm 110 can be part of the tattoo shuttle 104 and may be connected to the tattoo shuttle 104 through the Y gantry 106 and precision X gantry 107. The Y gantry 106 may be a mechanical gantry movable along the Y axis. The precision X gantry 107 may be a mechanical gantry movable along the X axis. Both the Y gantry 106 and the precision X gantry 107 may connect the arm 110 to the tattoo shuttle 104 to allow movement of the arm 110 along the X and Y axes.

The arm 110 may be further configured to hold actuators, such as, for example, a needle motor 111, an actuator 112 (e.g., zero stepper actuator), and an arm solenoid actuator 113. In one embodiment, needle motor 111 may be an electric motor configured to generate the rotational movement of a cam 114. In other embodiments, needle motor 111 may comprise of any other type of motor or method for generating rotational movement of cam 114. The needle motor 111 may also be connected to motor gantry 115, which is a structure that holds the needle motor 111 that can be lowered or raised by the action of the arm solenoid actuator 113. In one embodiment, the actuator 112 may be a stepper motor connected to the arm 110 and configured to set a needle maximum extension. In one embodiment, the arm solenoid actuator 113, may be a solenoid connected to the arm 110 which controls a position of the motor gantry 115. The arm 110 may be configured to be movable in the X, Y, and Z axes. In one embodiment, the arm 110 may also hold the needle structure 140.

In one embodiment, the contactor 120 may be a disposable component in contact with the skin and monobloc with the tattoo shuttle 104. The contactor 120 may comprise of a variety of shapes and sizes and may be configured to flatten the skin and keep excess ink and other fluid(s) from spreading. For example, in one embodiment the contactor 120 is generally rectangular and/or flat with a rectangular window configured to flatten and expose a portion of the skin to the needle structure 140. In other embodiments, however, the contactor can be shaped and/or sized in accordance with a contour of the area to be tattooed. In one embodiment, the contactor 120 is in contact with the skin and can move along the X axis. While in contact with the skin, the contactor 120 may apply a nominal force on the skin in the N axis direction, as referenced in FIG. 1B. The amount of force can vary, but in one example, the force may be between 1 lb and 10 lb. In some embodiments, the applied force can be less than about 1 lb, 2 lb, 3 lb, 4 lb, 5 lb, 6 lb, 7 lb, 8 lb, 9 lb, or 10 lb. The contactor 120 may contain a window that exposes a flattened area of skin. The window may comprise of a width and a length that varies in direction and magnitude. For example, the window length may be in the Y axis direction while the window width may be between 0.5 mm and 5 mm. In another embodiment, the window may span from one end of the tattoo frame 103 to the other end of the tattoo frame 103 in the Y axis direction.

The machine vision device 130 can be part of the shuttle 104 or a separate component of the apparatus 100. The machine vision device 130 can include an imaging device 131 and a lens 132 and be configured to obtain one or more images of a portion of skin. The imaging device 131 may be, for example, one or more sensors, cameras, or image capture elements connected to the lens 132. In other embodiments, the imaging device 131 may be a plurality of sensors or a digital camera. In one embodiment, the lens 132 may be a telecentric lens, such as a set of optical elements normal to the XY plane and focused on the window of contactor 120. The orientation of the telecentric lens 132 and its field of vision for the machine vision device 130 may vary, however. For example, the field of vision may span the entirety of a tattoo field. In another example, the machine vision device 130 may be kept at a fixed distance from the contactor 120 to keep the skin in the depth of field of the telecentric lens 132. Additionally, in another embodiment, the lens 132 may be fixed with respect to the contactor 120 and the tattoo shuttle 104. In some embodiments, the machine vision device 130 may additionally include an illumination system such as a light source (not shown). The illumination system may be positioned such as to minimize specular reflection toward the machine vision device 130.

In some embodiments, the needle structure 140 can include a needle cartridge 141, needle 142, needle piston 143, needle spring 144, plunger 145, and cam 114. The needle cartridge 141 may be a disposable component holding a tattoo needle and composed of the needle spring 144, needle piston 143, and needle 142. The needle cartridge 141 may be connected to the tattoo shuttle 104, but alternatively, may be configured to be removably coupled with the tattoo shuttle 104. The needle 142 may be a stainless-steel needle composed of a plurality of tapered and sharpened rods brazed together. The configuration of the needle 142 and cartridge 141 can be selected based on the tattoo to be applied, characteristics of the subject's tissue, or the like.

The needle piston 143 may be a plastic rod holding the tattoo needle 142. The needle spring 144 may be a plastic membrane connected to the needle piston 143. The plunger 145 may be a metal rod joined to the cam 114 and the needle piston 143. The cam 114 may be a metal cam with a fixed eccentricity transforming, together with the plunger 145, the rotational movement of the needle motor 111 to a linear movement of the needle piston 143, and subsequently the needle 142, along the Z axis. Alternatively, the components of the needle structure 140 may be of any suitable material aside from those mentioned for the embodiment described. In other embodiments, the components such as the needle motor 111 and cam 114 may be replaced by any other method suitable for generating movement (e.g., linear movement) of the needle piston 143.

Methods for Applying Tattoos

Figure 3A:
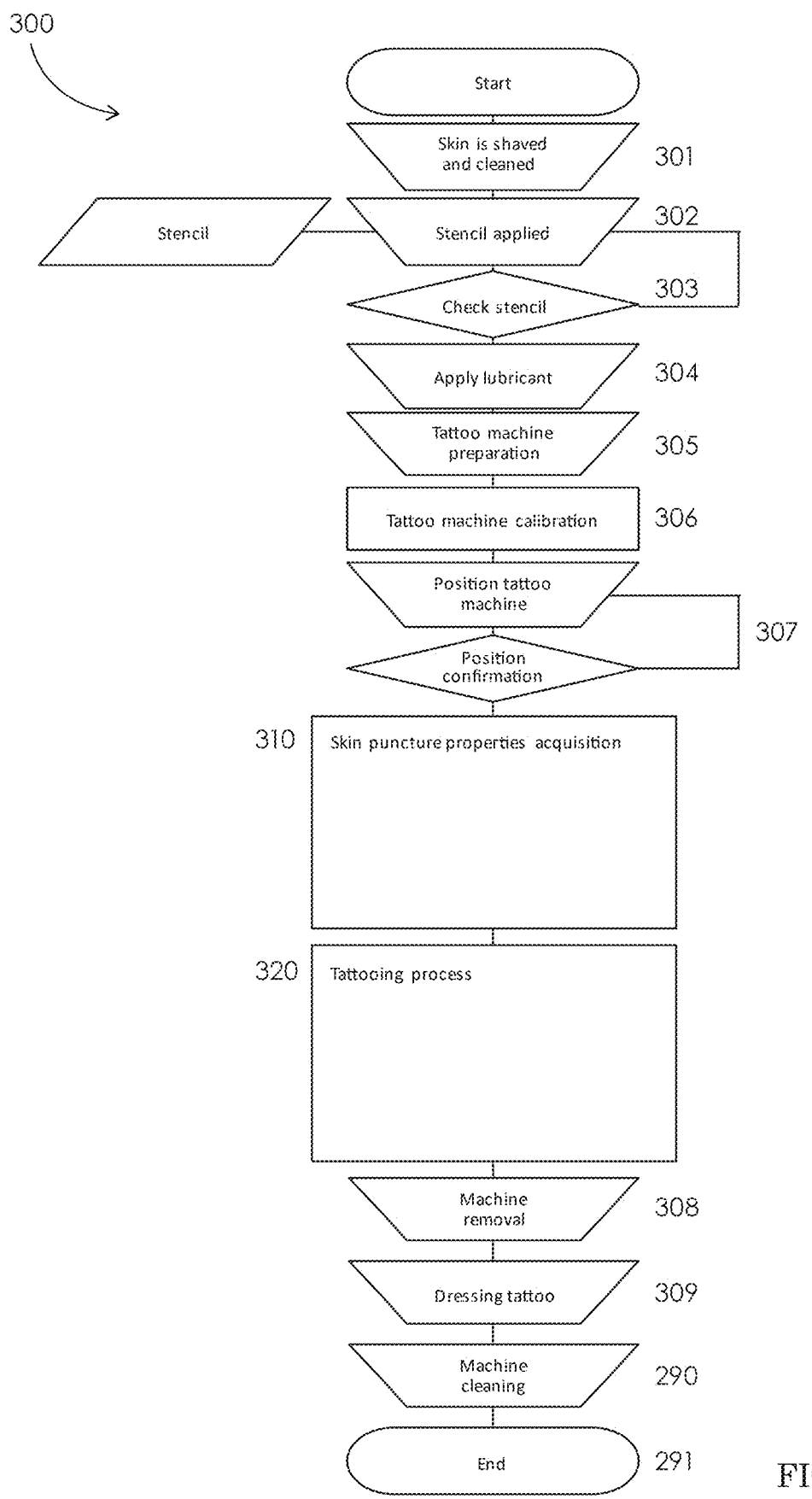
FIG. 3A is a block diagram of a tattooing process in accordance with an embodiment of the disclosure.

FIG. 3A is a block diagram of a tattooing process 300 in accordance with an embodiment of the disclosure. The tattooing process 300 can be used to apply tattoos (e.g., micro tattoos, dotwork, blackwork tattoos, realism tattoos, fine-line tattoos, etc.) and other permanent or temporary artwork. Although certain features of the method 300 are described with respect to embodiments of FIGS. 1A-2, it will be appreciated that the process 300 can be performed using any of the systems, devices, and technology discussed with respect to FIGS. 5A-19.

In step 301, a portion of skin that will receive the tattoo can be shaved and cleaned. For example, an operator (e.g., operator 72 of FIG. 1A) can manually clean and shave the site. The preparation protocol can be selected based on the subject's health, characteristics of the target tattoo site (e.g., amount of hair, skin condition, size of target site, appearance of skin, etc.), characteristics of tattoo site (e.g., a flat region, a curved region, etc.), or the like.

In step 302, a stencil can be applied to the portion of skin. The stencil may be a set of dots printed on transfer paper that serves as a positional fiduciary to identify the deformation of the skin during the tattooing process. Techniques for identifying deformation of the skin are discussed in connection with FIG. 7. In one embodiment, the stencil may also contain an outline or contours of the design for the subject to preview the placement of the tattoo. An algorithm may be used to generate the contour from a design. Generation of contours or outlines of a tattoo design is discussed in connection with FIG. 19. The stencil may also comprise of a subset of dots with variable shapes or patterns to encode dot positions. The size, shape, color, and density of the dots of the stencil may vary. In one embodiment, the dots may correspond to dot positions on a dot parameter table. The stenciling can be applied by an operator or the tattoo apparatus. In some embodiments, a stenciling protocol can be generated based on the tattoo design. The stenciling protocol can include, without limitation, generating a pattern of reference features (e.g., temporary dots) generated to assist with machine vision-based positioning of a tattoo device. For example, spacing between reference features can be reduced to apply micro tattoos. In some embodiments, automated and manual procedures are used to prepare the treatment site. For example, the stencil can be manually applied to the treatment site, and the tattoo apparatus can then apply a pattern-encoded set of reference features to the target site. In some embodiments, the stencil may be transferred to the skin by the intermediary of a flat substrate, such as paper, onto which the stencil design may have been printed using an appropriate dye to temporarily stain the skin. These stencil and reference features can be used to determine where to puncture the skin to produce the desired tattoo. The manual and automated steps of a stenciling protocol can be selected based on the functionality of the tattooing apparatus. In some embodiments, the natural features of the skin may be used as a reference fiducial instead of a stencil.

After application of the stencil 302, the subject and tattooing apparatus operator may check the stencil 303. The subject may review the stencil application and either approve or disapprove of the design placement. The operator may review the stencil for quality of application. In some embodiments, for example, a stencil deposition should be such that a transfer of fiducial marks is adequate to perform a machine vision algorithm and the pattern formed by the fiducial marks should not be substantially deformed when the skin is relaxed. If the stencil appears misplaced or the application is not accepted by the client, the stencil application step may be repeated until accepted. In one embodiment, the tattooing apparatus 100 may review the stencil for placement and/or application, automatically using, for example, one or more machine learning models trained to review stencil results for quality (e.g., could use past accepted and rejected stencil applications as training data).

Following approval of the stencil application, lubricant is applied in step 304. A variety of suitable lubricants with different viscosities and hydrophobic properties may be suitable for use. For example, a lubricant with a viscosity between 10 cps and 500 cps with hydrophobic properties to increase the contact angle between ink droplets and skin may be used. The lubricant can be chosen such that the type and viscosity of the lubricant may allow it to protect the epidermis top surface from being stained by ink and/or increase ease of removal of the ink and/or lubricant by suction via suction system (e.g., suction systems 150, 450). In some embodiments, the lubricant may be applied automatically by the machine 100 when and where it is suitable by an intermediary of a fluidic system.

Tattoo machine preparation 305 can occur after the lubricant is applied in step 304. Some steps of the machine preparation 305 may be performed before the arrival of the client and/or after selection of the tattoo to be applied. The tattoo machine preparation step 305 may comprise of a variety of activities and may differ between tattooing processes 300. Referring now to FIGS. 1B and 3A, in one embodiment, the operator may begin by mounting an appropriate tattoo frame 103 (FIG. 1B), which corresponds to the area of the body to be tattooed, such that the tattoo frame 103 is in contact with the skin to isolate the area where the tattoo is to be applied. In one embodiment, the tattoo frame 103 may be configured such that an operator may mount one or more sterile electrodes 117 (two illustrated in FIG. 1B) to the tattoo frame 103. The electrodes 117 may comprise of the same or different electrodes capable of making at least one type of measurement. For example, the one or more electrodes 117 may be a plurality of electrodes for measuring galvanic response. In one particular embodiment, the one or more electrodes 117 may already have been mounted on the tattoo frame 103 prior to preparation. The number, type, and positioning of electrodes 117 may vary depending on the desired measurements and configuration. In one embodiment, for example, one electrode 117 may be mounted at a location more proximate to the contactor 120 than another electrode 117. In other embodiments, electrodes 117 may be placed or located on other parts of the tattooing apparatus 100 and/or on the subject's body. Following mounting the tattoo frame 103, the operator may then proceed to isolate the tattooing area from the rest of the body and tattooing apparatus 100 by mounting, for example, a sterile membrane and/or bag system.

Referring again to FIG. 2, the operator may then mount a sterilized needle cartridge 141 and an ink cartridge (not shown) to the tattooing apparatus 100. In one particular embodiment, the needle cartridge and/or ink cartridge can be coupled to the needle structure 140. Example needle cartridges are discussed in connection with FIGS. 10A and 10B.

With continued reference to FIGS. 1A-3A, after mounting the needle cartridge 141 (FIG. 2) and ink cartridge, the operator may then mount additional components of the machine vision device 130 (FIG. 2) to the machine. In one embodiment, the additional components of the machine vision device 130 may be a sterile imaging device 131 and vision viewport. The vision viewport may be a sterilizable viewport suitable for camera vision. Other embodiments may comprise fewer or more components. In one particular embodiment, the machine vision device 130 may already contain all necessary parts and preparation may comprise only of sterilizing the parts.

Additionally, the operator may mount a suction system 150 (FIG. 2) to the tattooing apparatus 100. The suction system 150 may comprise of one or more conduits, lines, pumps, valves, nozzles, containers, filters, and/or other components. In one embodiment, the suction system 150 may be, for example, a sterile, single usage suction line comprising of a nozzle, tubing, a microperforated air filter, and a liquid trap. In other embodiments, the suction system 150 may be reusable and/or comprise more or fewer parts. In one particular embodiment, the suction system 150 may already be mounted to the machine and preparation may comprise only of sterilizing the suction system 150.

Following preparation 305 of FIG. 3A, the tattooing apparatus 100 may calibrate itself, or may be calibrated by the operator, in tattoo machine calibration step 306. Tattoo machine calibration 306 may comprise of running all or some of the actuation systems and sensors to evaluate nominal functioning. Referring now to FIGS. 2 and 3A, the tattooing apparatus 100 may perform zero reference calibration by measuring its range. In one embodiment, range can be measured through using a plurality of end range sensors, encoder sensors, etc. to calibrate the position of the needle 142 in space. Running all sensors may also comprise of running components of the machine vision device 130 such as the imaging device 131. In one embodiment, calibration may comprise of using an algorithm to run a diagnostic of the sensors and imaging device 131. Additionally, a conductivity test may be performed to confirm connection of one or more electrodes to the machine and/or to the skin. The calibration step 306 may also comprise of using a reference pattern in the tattoo frame 103 to confirm camera vision and illumination. In various embodiments, the calibration step 306 may comprise more or fewer than the preceding steps as well as other steps suitable for appropriate calibration of the machine for the tattooing process. In some embodiments, the calibration step 306 can be omitted. In some implementations, parts of the calibration process can be performed at other times, such as when the tattooing apparatus 100 is powered on, prior to the stencil application, prior to the tattoo machine preparation step 305, or other suitable time.

Following calibration step 306 of FIG. 3A, the operator may then proceed to positioning step 307, which may comprise of positioning the tattooing apparatus 100 appropriately relative to the area to be tattooed and confirming a proper positioning. Referring now to FIGS. 1A-3A, positioning the tattooing apparatus may comprise of selecting the appropriate size of tattoo frame 103, orienting the subject and area to be tattooed relative to the rest surface 102 and tattoo frame 103, and aligning a machine tattoo zone with the area to be tattooed by rotating and/or repositioning the tattooing apparatus 100 and/or subject to match a location of the tattoo. An operator, or the machine itself, may then confirm appropriate positioning by using the machine vision device 130, e.g., to determine that identified skin features and/or stenciling are positioned to allow the tattooing apparatus 100 to apply the selected design with the previously determined position and orientation characteristics. In one embodiment, the machine vision device 130 may use a machine vision algorithm to identify each dot position in a stencil and compare it to a vector-based stencil design. The position of the stencil with respect to the tattoo frame 103 may be validated as well as whether there is a correct transfer of dots for calculating skin stretch and/or deformation. If the stencil deposition is such that the transfer of fiducial marks is inadequate to perform the machine vision algorithm and/or if the tattoo frame 103 is not properly positioned, an operator error is generated suggesting either reapplication of the stencil or realignment of the tattoo frame 103. In one embodiment, for example, an error may be generated if a sufficient number of dots corresponding to an aspect of the design (e.g., design contour) do not match. The machine vision device 130 may include one or more controllers storing the machine vision algorithms. Alternatively, separate controllers (e.g., controllers 108, 109) can perform the machine vision algorithms.

Figure 3B:
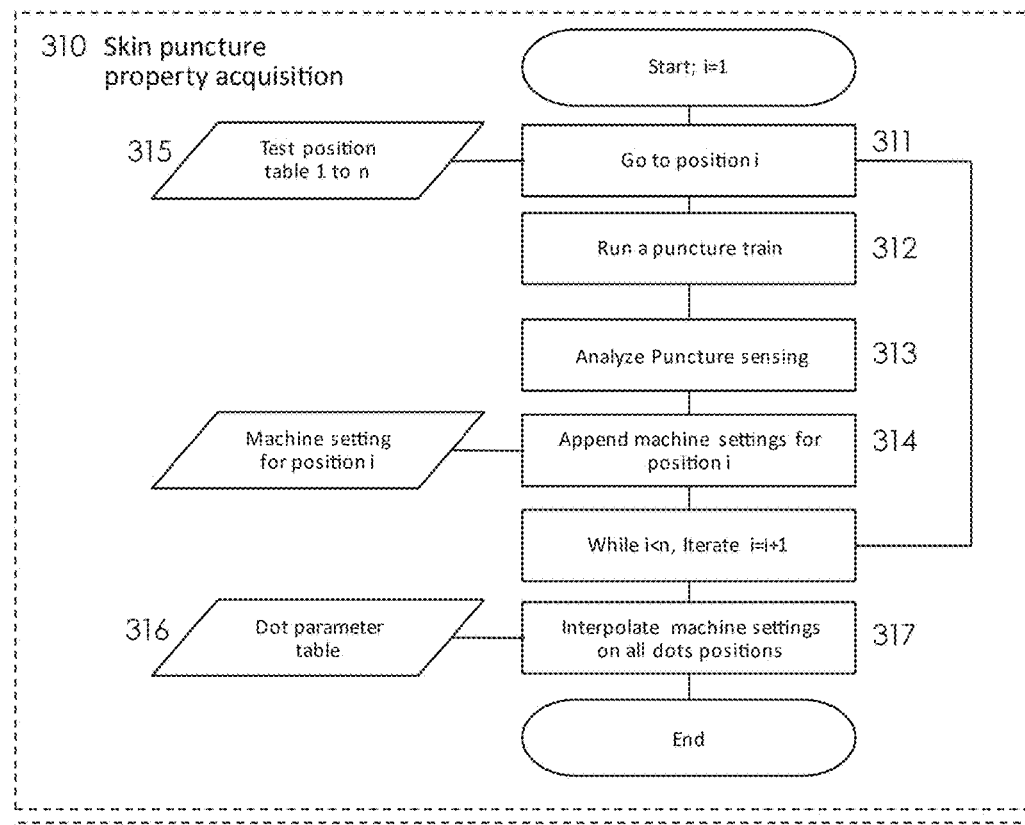
FIG. 3B is a block diagram of a skin puncture property acquisition step of the tattooing process in accordance with the embodiment of FIG. 3A.

After confirming that the machine is properly positioned, skin puncture property acquisition step 310 may then be performed by the machine itself, or the operator. FIG. 3B illustrates an expanded block diagram of an embodiment of the skin puncture property acquisition step 310. For example, the skin puncture property acquisition step 310 may comprise of performing a series of punctures distributed around the area to be tattooed with no ink. In some embodiments, multiple punctures may be performed for each position. The machine may be set to a safe depth setting such that the epidermis and dermis are punctured in the process. For each of the positions, information about the puncture operation is recorded with one or more sensors, which may be redundant for reliability. In one embodiment, the one or more sensors may include, but are not limited to, a load cell sensor, an accelerometer, an encoder, a set of galvanic electrodes, and a vibration sensor. The load cell sensor may be located on the needle plunger 145 of FIG. 2 and may be configured to measure a load applied to the plunger 145 during tattooing. The accelerometer may be on the plunger 145 and may be configured to measure an acceleration of the needle 142. The encoder may be located on the needle motor 111 and may be configured to measure an angular position of the needle structure 140. The set of galvanic electrodes may be configured to measure an impedance of the needle 142 to skin contact relative to an impedance of the skin alone. The vibration sensor may be configured to measure a vibration of the contactor 120. The locations, quantities, and types of sensors may vary depending on the particular embodiment and process.

Referring now to FIGS. 2 and 3A, the sensors can measure properties of the needle/skin system and precisely identify when skin puncture events occur during one rotation of the needle motor 111 (FIG. 2). Certain factors related to the needle/skin system may influence the complex behavior of the skin in terms of deformation and failure. For example, needle sharpness, number of needles, needle gauge, and speed may all be influencing factors. Additionally, certain skin characteristics such as elasticity, impedance, thickness, etc. may also be influencing factors. By measuring when the different layers of the skin fail (colloquially, when puncture occurs), the configuration of the machine can be varied by varying needle 142 (FIG. 2) extension out of the cartridge 141 and needle motor 111 speed such that a force applied to the skin is minimized and a maximum extension of the needle 142 can be insured. One rational is that an ultimate position of a tip of the needle 142 should be in the papillary zone of the dermis for optimal tattooing (e.g., to prevent or limit scattering, subdermal diffusion, etc.).

Referring again to FIG. 2, one or more of the exact elastic property of the skin, thickness of the skin, sharpness of the needle 142, and/or exact force transfer from the needle 142 to the skin may be unknown. Puncture tests can be performed on the skin to determine one or more machine settings. The puncture events can integrate some or all the parameters needed to pilot the needle 142 without having to measure skin characteristics, needle characteristics, and/or machine characteristics. In particular, the skin may be susceptible to deflection and compression, which are the primary determinates of the layer of tissue in which the needle reached. The deflection of the skin can be proportional to the distance traveled by the needle 142 between first skin contact and epidermis puncture. The measurement of skin contact, initial puncture, needle displacement and/or needle extension (e.g., maximum needle extension) can be used to pilot the height of the motor gantry 115 compared to the needle cartridge 141, which in turn can set the ultimate extension of the needle 142 and control the depth of piercing of the tissue (i.e., the puncture depth). The puncture depth can be the depth of a single needle or an average depth of a plurality of pins (e.g., a bundle of pins) of a tattoo needle. In some embodiments, the ultimate extension can be the maximum depth of a bundle of pins of a tattoo needle. For reliability, each position may be subjected to a train of punctures ranging from 1 to 50 punctures and the measured metrics may be averaged over multiple punctures. In some embodiments, the sensing strategy may be configured to detect a depth of the needle during a puncture event based at least in part on a relationship between a force applied to the skin and the depth of the tissue layer interface. Another embodiment of the current sensing strategy may be configured to detect the depth of the needle during a puncture event based at least in part on the contact conductivity (including changes in contact conductivity) of the needle against the skin, relative to the conductivity of the skin alone. The detected puncture event may be, for example, the failure initiation of the epidermis during the needle transition from surface of the epidermis to the epidermis to dermis layer interface. In some embodiments, determination of a proper height setting, needle extension, puncture event depth, and/or predicted depth of ink deposition may be based at least in part on the force applied to the skin. In other embodiments, determination of a proper height setting, needle extension, puncture event depth, and/or predicted depth of ink deposition may be based at least in part on the contact conductivity, such as the variation of the contact conductivity of the needle against the skin, relative to the conductivity of the skin alone as exemplified and discussed in connection with FIGS. 12A and 12B. The puncture events can be identified by analyzing the conductivity data. For example, puncture events can be determined based on, for example, extrema of the conductivity curve obtained by the galvanic sensor, as well as the extrema of its first derivative with respect to time, as exemplified and discussed in connection with FIG. 12B.

For each location on the skin tested, the target needle 142 extension parameter (e.g., maximum displacement) for the execution of a dot of acceptable quality may be calculated using one or more algorithms based on collected data associated with initial or first contact, skin puncture, and maximum depth as exemplified and discussed in connection with FIGS. 12A and 12B. The data for each of the test positions can be stored. In one embodiment, for example, calculating the correct ultimate needle extension (e.g., maximum displacement of the needle or puncture depth) may be based at least in part on: a relative impedance of the skin/needle contact compared to the skin impedance as measured by the galvanic electrodes, a force magnitude, needle speed, needle acceleration, an angular position correlating to a needle 142 position at a certain time, or an algorithm that uses measured puncture events such as contact with skin, initial epidermis failure, additional layer failure, or ultimate needle 142 position to evaluate the maximum needle 142 position that results in a correctly applied tattoo dot. The collected data and metrics collected for each position tested can be stored, aggregated, analyzed, etc.

In one embodiment, an algorithm for predicting the ultimate needle depth in relaxed skin can be based on the sum of a weighted polynomial or any other set of relevant basis functions of the sensor measurements. Experimental calibration can be used to obtain the coefficients associated with each polynomial term. The depth prediction is then compared to the desired depth on relaxed skin to issue a change of height of the needle 142. An algorithm can be used to predict the depth of ink deposition based on the needle position at contact, the needle position at initial puncture, the needle position at max extension, the needle position when exiting the skin, and/or the angle of attack of the needle. Illustrative diagrams of example puncture events, for reference are discussed in connection with FIG. 12A. The extrema of the output of the galvanic sensor can be correlated to each example of the puncture events as discussed in connection with FIG. 12B.

Puncture events can be used to calibrate for variation of needle lengths due to, for example, variation in needle manufacturing. During one oscillation, the needle starts from its uppermost position. Then the needle contacts the skin. Following this, the needle punctures various skin layers until the needle reaches its lowermost position, the maximum extension. Longer needles will touch the skin earlier while shorter needles will touch the skin later in the cycle. Similarly, the skin height may vary within the contactor window by forming a bulge. By varying the needle extension, the tattooing system can compensate for various needle lengths and skin positions/heights by, for example, raising the needle (e.g., raising with respect to skin surface) to compensate for longer needles and/or higher skin height or lowering the needle to compensate for shorter needles and/or lower skin height. In some procedures, needle extension may be varied to maintain a consistent distance measured between skin contact and needle at maximum extension, and thus maintain a consistent depth of ink deposition. Measuring the distance between the tattooing head and the skin surface, for example using distance sensors (e.g. based on time of flight, light projection, haptic sensors, etc.) does not account for variations in needle length, or other geometric variations of needle cartridges.

Referring again to FIG. 3A, the skin puncture property acquisition 310 can include determining an initial deflection to puncture, which is the distance traveled by the needle from the time of first skin contact to the time of initial skin puncture. A distance traveled to puncture corresponding to the difference between a position of initial skin puncture and a position at skin contact can be derived. This distance is the initial deflection. Similarly, a distance traveled in the skin to max extension, which is the max extension, is the difference between a position at a predetermined or maximum extension and the position at contact. Because the skin deforms during puncture, the predetermined or maximum extension is not directly linked to the depth of ink deposition. Similarly, the initial deflection can relate only to the deflection until puncture, not the deflection at maximum depth, which is the total deflection. The total deflection may be assumed in the algorithm to have an affine relationship with the initial deflection. A more complex relationship between total and initial deflection may be devised based on weighted polynomials or any set of relevant basis functions. A prediction of the depth of ink may be obtained by deriving an affine relationship (or another appropriate mathematical fit) between the depth of ink and the difference of the max extension and the total deflection, accounting for the necessary trigonometric relations due to the needle angle with respect to an axis normal to the skin's surface. In some embodiments, the desired ink location for human skin may lay between 0.5 mm and 1.2 mm deep on relaxed skin. In some embodiments, the change in needle 142 height setting can be calculated to be the difference between the predicted depth and the desired ink location. From the calculations and measurements, a corresponding map of the tested positions on the skin containing the measured and/or calculated metrics such as, for example, a needle height, a needle extension, and/or a predicted depth of ink deposition may be generated and stored. The depth of the ink may be used as a non-visual metric to evaluate dot quality. A method for the analysis of puncture parameters and/or determination of puncture settings based on training data explicitly introducing dot aesthetic quality is discussed in connection with FIG. 13.

In one embodiment, each position on the skin may be identified by the machine vision device 130 (FIG. 2) to confirm an absolute skin location. In normal operation of the machine, the skin is stretched resulting in a planar elastic deformation. This in turn means that the position of the machine needle 142 does not necessarily match with the position on the skin due to skin stretch. The machine vision device 130 may be used to acquire at least one image of the skin and a digital image correlation or other image analysis method may be used to calculate a skin displacement field. An embodiment of this method is presented in connection to FIG. 7. This displacement field may be used to calculate the true location of the needle 142 on the skin such that the set of sensor data used for defining a proper needle extension for each skin location is in a relaxed skin frame of reference. An algorithm that calculates skin deformation may be used to identify the position of the needle 142 from processing of at least one acquired image of the skin. Additionally, information about skin puncture in a skin positional frame of reference may be recorded in a database. The database may also, for example, record the prescribed needle extension at the sensed puncture position in an undeformed positional frame of reference of the skin.

Once all the prescribed positions designated for testing of the skin have been punctured, the punctures analyzed, and the prescribed needle extension for these positions saved, an interpolation algorithm may be used to interpolate the needle extension for all the dot locations that are part of the tattoo design. This allows evaluation of the proper height setting of the machine. The interpolation algorithm may be, for example, an algorithm that interpolates the prescribed needle extension from the test puncture points to the dot positions corresponding to positions not tested. The interpolation can include determining a depth plane for all punctures that is a fit to the saved positions and applies a smoothing function between them.

FIG. 3B illustrates an embodiment of the skin puncture property acquisition suitable for the step 310 that is shown in FIG. 3A. The skin puncture property acquisition step 310 can begin, in step 311, at position i. A puncture train is then run at position i, which may consist of at least one puncture 312. Data measured from the punctures by at least one sensor may then be analyzed for each position i 313. Certain puncture metrics may be calculated and a machine setting for position i may be determined based on the measured data and appended/recorded for position i as in step 314. For example, the machine setting may be based at least in part on any of the calculations as described. In one embodiment, the machine setting may be at least a proper height setting, needle extension, and may include parameters based upon puncture events, tissue layer interface depth, or predicted depth of ink deposition. Steps 311-314 may be repeated for all testing positions 1 to n according to test position table 315. The appended and recorded machine settings may then be used to update dot parameters of a dot parameter table 316, which may be representative of the tattoo design. The updated dot parameter table 316 may comprise of one or more dot positions, wherein at least some of the dot positions may correspond to the tested positions of test position table 315. In one embodiment, there may be more dot positions than tested positions and machine settings may be interpolated for the dot positions that do not have a corresponding test position 317. For example, machine settings can be interpolated for dot positions that do not correspond to tested positions of the test positions table 315 based on the appended and recorded machine settings for tested positions. In another embodiment, there may be the same number of dot positions as tested positions, and the tested positions may correspond to all dot positions in the updated dot parameter table 316.

Figure 3C:
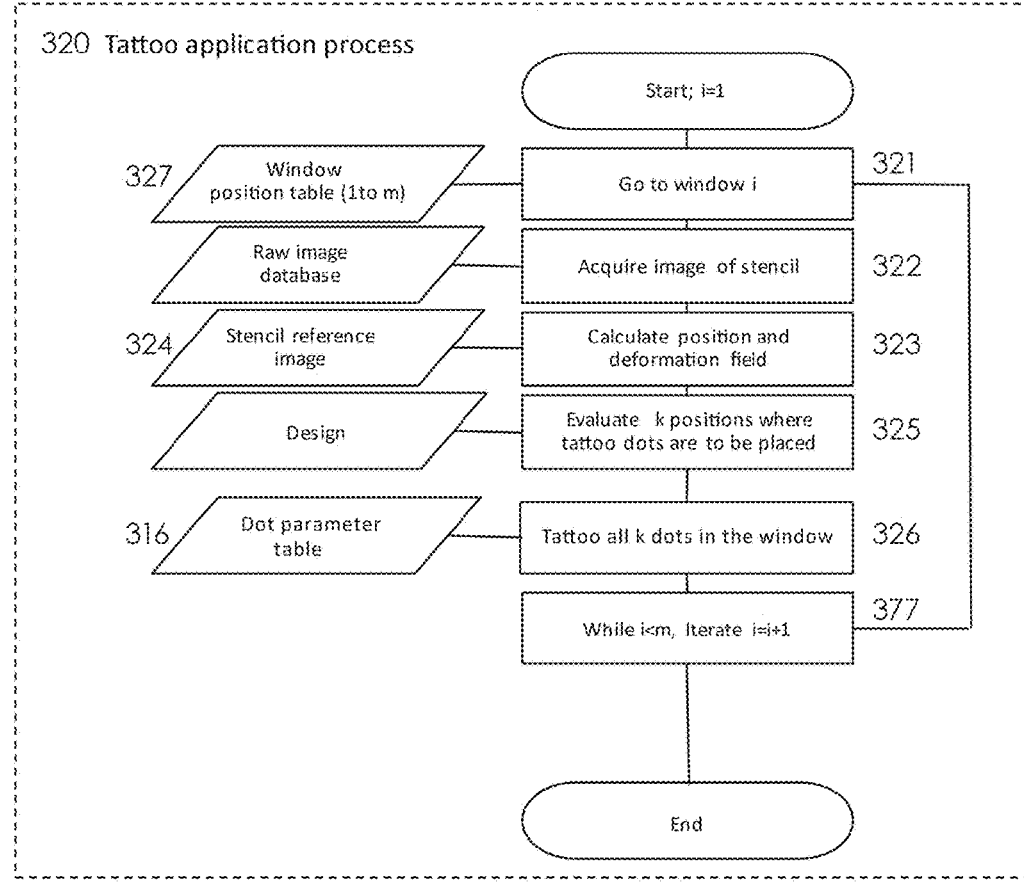
FIG. 3C is a block diagram of a tattoo application process step (tattooing process step) of the tattooing process in accordance with the embodiment of FIG. 3A.

Referring now to FIGS. 3A and 3C, the tattoo application process step 320 follows completion of skin puncture property acquisition step 310. FIG. 3C shows an expanded block diagram of an embodiment of the tattoo application process step 320. In one embodiment, tattoo application process step 320 may be based at least in part on the updated dot parameter table 316 (FIG. 3B) with corresponding appended and recorded machine settings. In one example, a map of prescribed needle depths may be defined based at least in part on the updated dot parameter table 316. Once the map of prescribed depths is defined, the tattoo machine repositions itself at the beginning of the tattoo field. Referring now to FIG. 2, the imaging device 131 (FIG. 2) may be used to scan a tattoo window i. In some embodiments, tattoo window i may correspond to a window of the contactor 120. The suction system 150 may be turned on. A machine vision deformation algorithm and a position algorithm may be used to evaluate the deformation of the skin as well as the position of the contactor 120, respectively. Algorithms for detecting the skin deformation and contactor position are discussed in connection with FIGS. 6A, 6B, and 7.

The deformation of the skin may be used to identify the positions of the tattoo dot prescribed in the reference undeformed vector-based graphics (one or more vector graphics) in the frame of reference of the contactor 120. The gantry movement of the tattoo shuttle 104 (FIG. 1B) is prescribed for realizing the tattooing of all dots that are within a central subset of the tattoo window i from one side to the opposite side in the Y direction. Ink may be added to the needle cartridge 141 and/or ink cartridge by an ink recharging process. This ink recharging process may be repeated mid tattooing of the window i if the level of ink in the needle cartridge 141 and/or ink cartridge is insufficient to tattoo all the dots present in the tattoo window i.

With reference to FIGS. 1B, 2, and 3B, the needle motor 111 is started to reach expected tattoo speed and to wet the needle 142 tip with ink. The zero-stepper actuator 112 is set for the needle extension of a first tattoo dot in the window i. The X gantry 105 and Y gantry 106 are actuated to position the needle 142 tip over the first dot location. The arm solenoid actuator 113 is energized to drop the motor gantry 115 down such that the needle piston 143 is compressed by the needle plunger 145 and that needle oscillation occurs at the Z reference set by the zero-stepper actuator 112. A reason for the arm solenoid actuator 113 is to rapidly engage the needle 142 with the skin without the needle motor 111 starting inertia. The needle 142 oscillates between a high position and a low position defined by the maximum needle extension controlled by the zero-stepper actuator 112. A number of punctures for a single dot may be set by a design file and may vary the dot size and color density. For example, the number of punctures for a single dot may be between 1 puncture and 50 punctures. An encoder sensor system and a galvanic sensor system may count the number of punctures and trigger the arm solenoid actuator 113 to raise the arm 110 when the prescribed number of punctures for that dot is reached (or calculated to be reached by taking into account transient effects related to actuation time).

The machine vision device 130 (FIG. 2) can be used to confirm correct dot application at that time. Once the arm 110 is confirmed to be raised by the sensor and algorithm, the needle 142 is not in contact with the skin and the gantry actuation is engaged to position the machine to the appropriate X and Y location and the calculated Z reference of the next dot to be tattooed. This tattoo process is repeated for all positions to be tattooed identified by the machine vision algorithm within the tattoo window i. The suction system 150 may be on throughout the process and may collect superficial drops of ink to improve the visibility for the machine vision device 130, or may be turned on when suction is necessary to remove fluids . . . .

Once a selected number (e.g., all the dots in the tattoo window i) are tattooed, a drainage system, which may comprise part of the suction system 150, may be triggered to remove the chance of ink dropping from the cartridge because such ink drops compromise the imaging of the skin by machine vision device 130. The needle motor 111 may then be turned off. The contactor 120 may be actuated forward in the X direction by a fraction of the window width, such that each new window of tattooing i+1 may overlap with at least a portion of a preceding window i. The forward direction is decided based on the natural growth direction of the tissue, which is generally from a base to extremities of the limbs, or for trunk tattoos, in the direction of gravity. The tattooing of the contactor 120 window in the new position i+1 repeats the same steps from the preceding tattoo window i and is reiterated until the end of the tattoo field is reached m. Once this is the case, the tattooing apparatus 100 may be put in a safe position and all actuators may be turned off.

FIG. 3C illustrates an embodiment of the tattoo application process suitable for step 320 shown in FIG. 3A. Referring now to FIG. 3C, the tattoo application process step 320 may begin at window position i as in step 321. The machine vision device 130 may then acquire at least one image of the stencil and store it in a raw image database as in step 322. A position algorithm may be used to calculate a position of the contactor 120 (see FIG. 2) and window i. Similarly, a deformation algorithm may be used to calculate a deformation of the skin at window i to identify the positions of the tattoo dot prescribed in the reference undeformed vectoral graphics in the frame of reference of the contactor 120. Both the position algorithm and the deformation algorithm may take into account at least a stencil reference image 324 when calculating the position and skin deformation in step 323. Algorithms for calculating the position and skin deformation are discussed in connection with FIGS. 6A, 6B, and 7. Based at least in part on a tattoo design and the calculated position and skin deformation of step 323, the tattoo application process step 320 may continue by evaluating one or more positions k where tattoo dots are to be placed 325. The tattooing apparatus 100 may then tattoo all one or more positions k in the window i as in step 326 based at least in part on the updated dot parameter table 316. At step 327, if km, the process returns to step 312. Steps 321-326 may be repeated for all window positions 1 to m within window position table 327.

Referring again to FIG. 3A, after tattoo application process step 320 is completed, the tattooing apparatus may be removed as in step 308. The operator may remove the tattoo frame (e.g., frame 103 of FIG. 2) from the tattoo zone such that the subject may be freed from the tattooing apparatus 100 (FIG. 1). Any disposable components may then be removed and disposed of. As used herein, the term "disposable" when applied to a system or component (or combination of components), such as a needle, a tool, or stencil, is a broad term and generally means, without limitation, that the system or component in question is used a finite number of times and is then discarded. Some disposable components are used only once and are then discarded. In other embodiments, the components and instruments are non-disposable and can be used any number of times. In some kits, all of the components can be disposable to prevent cross-contamination. In some other kits, components (e.g., all or some of the components) can be reusable. Following machine removal step 308 of FIG. 3A, the tattoo area may be cleaned and dressed with a protection layer in dressing tattoo step 309. Additionally, a variety of aftercare treatments may be provided. Finally, the surface of the tattooing apparatus 100 of FIGS. 1A and 1B may be cleaned at step 290 with a cleaning solution so as to be suitable for a next use. At step 291, the process 300 is completed.

Figure 4:
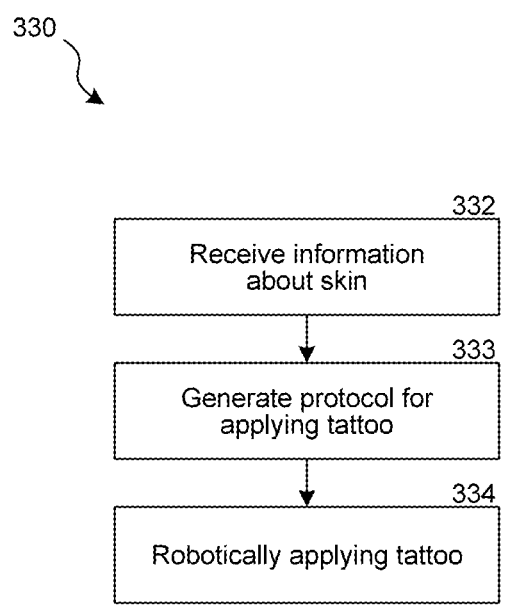
FIG. 4 is a block diagram of a tattooing process in accordance with an embodiment of the disclosure.

FIG. 4 is a block diagram of a tattooing process 330 in accordance with an embodiment of the disclosure. In step 332, a tattoo system can obtain information from the target site analyzer, such as a machine vision device, sensor, or the like. The information can include, without limitation, one or more images of a portion of the skin, and/or at least one characteristic of the portion of a subject's skin, skin puncture properties (step 310 of FIG. 3A), or the like. In step 333, a protocol for applying a tattoo can be generated based on the received information and a tattoo design. The protocol can include identifying changes associated with the skin capable of impacting a visual appearance of the tattoo to be applied. The protocol can include a plan or map of dots or individual punctures for applying the tattoo, together with application parameters for each. The tattoo system can compensate for the one or more changes (e.g., skin stretch, skin displacement, skin layer(s) thickness changes, etc.) associated with the skin to robotically apply at least a portion of the tattoo. For example, the spacing of the dots can be adjusted to match skin stretch at corresponding regions. If the system detects skin deflection increase, the system can increase the (e.g., puncture depth, maximum needle depth, depth ink is applied, etc.), needle displacement, or other applicator parameters for that region. A transformation can be applied to compensate for skin stretch, skin displacement, skin layers thickness changes, etc. For example, the spacing, pattern, and locations of puncture sites can be adjusted based on changes of the stenciling. A machine learning model can be trained to identify transformations to produce a tattoo on post-application that matches (e.g., geometrically congruent, visually identical to the naked eye, etc.) the tattoo design. For example, the applied tattoo can be placed with a deviation from the original design (e.g., average threshold deviation between dots and target dot of design less than 50 µm, 75 µm, or 100 µm) which may not affect the visual outcome of the tattoo. In some embodiments, a virtual tattoo design can be generated to match the variation of measurable characteristics of the skin. For example, if the skin is stretched, a stretched virtual tattoo design, stretched stencil, etc. can be configured to compensate for the stretching of the skin. New puncture points and tattooing parameters can be generated based on the virtual tattoo design. During the tattoo session, numerous virtual tattoo designs can be generated to determine how to apply a tattoo on skin such that, when the skin is in a natural state, the applied tattoo will match the original tattoo design. One or more machine learning model can be trained to generate virtual tattoo designs and/or stencils. For instance, a transformation of the tattoo characteristics such as dot parameter, dot placement, dot density and such can be generated such that it would compensate for certain measured characteristics of the skin, such as skin color, variation in coloration, features such as moles and birthmarks and tissue thickness, bone backing and so on. These skin characteristics can be measured by machine vision and other sensors deployed by the automated tattoo machine. A machine learning strategy can be obtained by first generating a validated training set. One method may include a professional tattoo artist evaluating the type of transformation he/she would perform to obtain a more congruent tattoo for a certain area of the skin. Another method includes applying random transformations to the tattoo and use humans to evaluate the esthetic quality of virtually projected tattoo on the body area using augmented reality. Another method is to use a genetical algorithm or other optimized search to generate guesses for tattoo transformation, for evaluation for aesthetic quality by humans on virtually projected tattoos. A scoring method may be used to automatically evaluate congruence of the tattoo design after transformation. This training set may then be used by a machine learning algorithm to determine an optimal tattoo design transformation and for a large set of conditions where some skin characteristics are measurable. Another characteristic of the skin is the shape of the body area, which is curved and may need a special projection of the flat design (for example using area-preserving mapping, distance-preserving mapping, conformal mapping, or other projection methods), such that the result looks harmonious on curved body surfaces, such as on shoulders, elbows, wrist, etc.

In step 334, the tattoo system can robotically apply at least the portion of the tattoo according to the protocol. The protocol can be used to reduce one or more differences between a selected tattoo design and the tattoo applied to the skin. The stenciling and techniques discussed in connection with FIGS. 5A-6B and 11A and 11D may be used to determine dot puncture locations. In some computer-implemented methods, the system can apply one or more reference features to the skin and analyze at least one of the reference features captured in one or more of the images to evaluate one or more characteristics of the skin to determine one or more changes in the skin. The tattoo system can compensate for the one or more changes in the skin to determine puncture sites for applying the pigment.

Figure 5A:
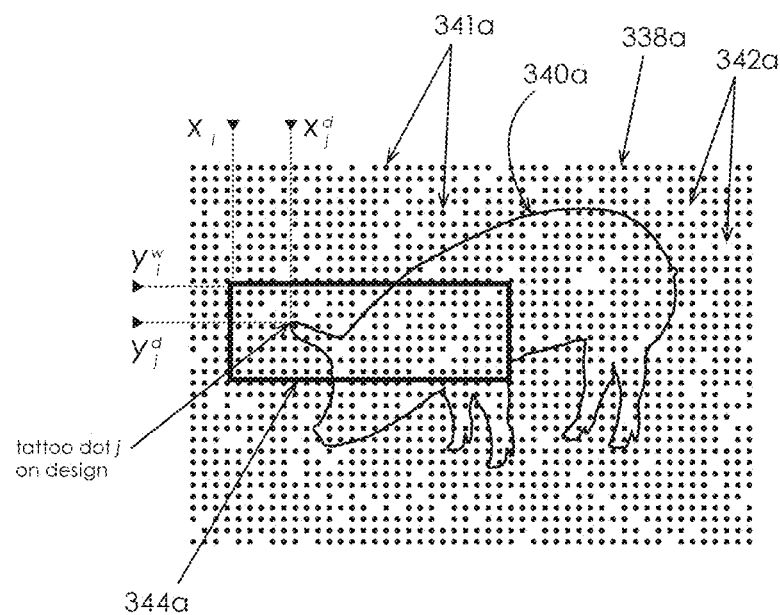
FIGS. 5A and 5B are illustrative diagrams of a stencil generation process in accordance with an embodiment of the disclosure.

Methods for Applying and Using Stencils, Image Analyses, and Machine Vision Technology FIG. 5A illustrates constituents of a stencil 338a and how it may be utilized by a machine vision algorithm, such as machine vision algorithm discussed in connection with step 323 of FIG. 3C. FIG. 5A shows one embodiment of a digital stencil reference that can be stored in memory (e.g., computing unit memory). The stencil reference can include at least (i) a tattoo design 340a, (ii) a reference stencil with fiducial markers 341a, and (iii) a pattern 342a encoded by fiducial markers which may be used to guide the machine vision process. The pattern 342a may be encoded by spatial variations of (a) size, (b) shape, (c) color and/or (d) presence/absence of fiducial markers. In one embodiment, the pattern 342a is encoded by (d) presence/absence of fiducial markers.

Figure 5B:
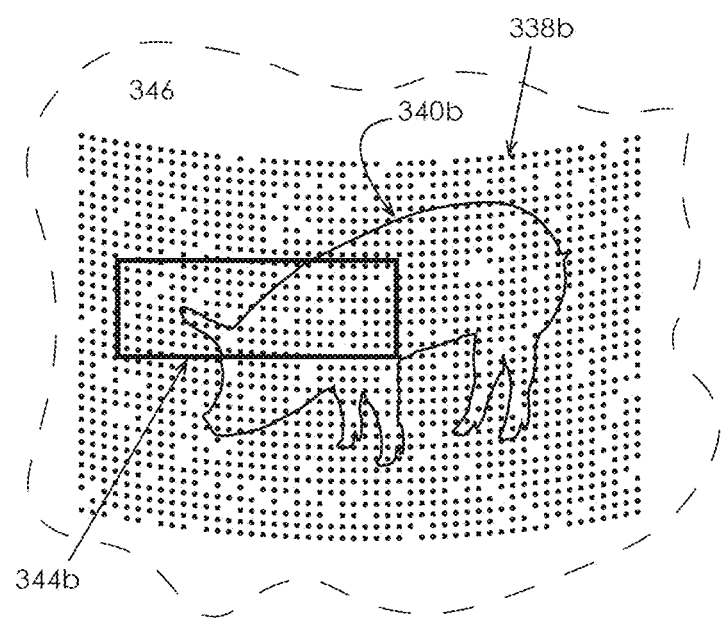

FIG. 5B depicts an embodiment of the stencil 338b transferred and viewed on the skin 346. In some procedures, the stencils 338a, 338b can be substantially identical in sizes and/or shapes. The tattoo design 340b on the applied stencil 338b may be utilized for previewing the tattoo placement, and may be (i) a complete representation of the tattoo design, (ii) a reduced form of the tattoo design, such as an outline or contours representing the tattoo design, or (iii) may not be placed on the applied stencil, at all. The transferred stencil 338b may stretch and rotate with the skin 346. During tattooing operation, a contactor (e.g., contactor 120 of FIGS. 1B and 2) can move across the skin as in step 321 of FIG. 3C. One possible position of an interrogation or contactor window 344b (e.g., detector portion of the interrogation or contactor window) is shown in FIG. 5B. The contactor window 344b can be moved to different locations to analyze and apply dots at different locations along the target site.

Figure 6A:
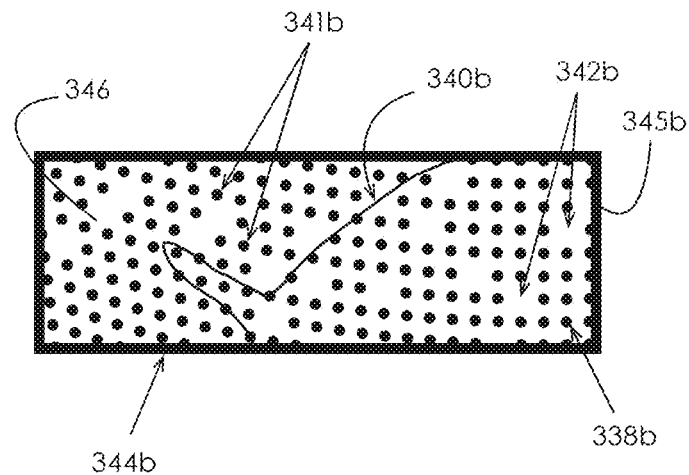
FIG. 6A illustrates an image captured by an image capture device in accordance with an embodiment of the disclosure.
Figure 6B:
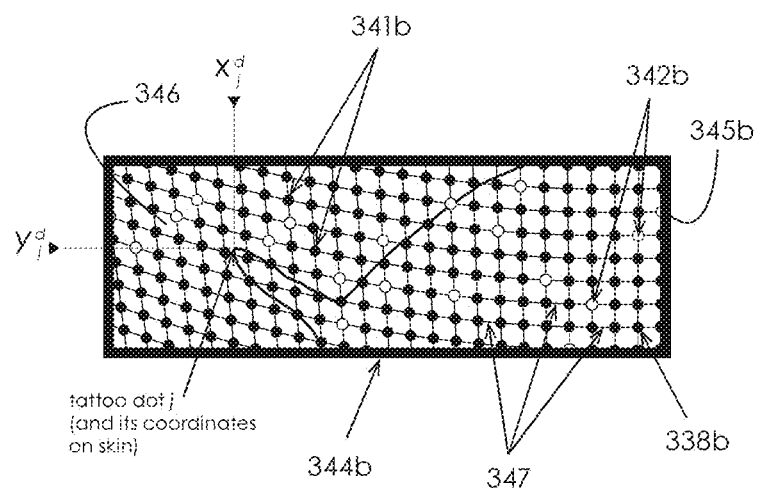
FIG. 6B illustrates an image analysis using one or more machine vision algorithms in accordance with an embodiment of the disclosure.

FIG. 6A shows one embodiment of an image captured by the machine vision device through the contactor window 344b of FIG. 5B. FIG. 6B illustrates features of FIG. 6A detectable using the machine vision algorithm. Referring now to FIG. 6A, the contactor window 344b exposes a portion of the skin 346, the applied stencil 338b, including the fiducial markers 341b and the encoded pattern 342b and the tattoo design on the applied stencil 340b. The viewable area 345b may also contain other features, such as, previously applied tattooed ink, residual ink, blood, moles, hair, hair roots, skin creases, light glare, etc. These are not shown in the figure for clarity, but may be addressed by the machine vision algorithm, as discussed in connection with FIG. 7.

Referring now to FIG. 6B, the detectable features can include, without limitation, fiducial markers 341b, the spatial variation of markers which constitute a pattern 342b, deformation field of the skin 347, and other features of the stencil 338b. The design and use of the stencil (338a in FIG. 5A, and 338b in FIGS. 5B and 6A) enables the machine vision algorithm (FIG. 7) to identify the position of the contactor window 344b on the skin 346, map the coordinates of the tattoo dots of the design 340a to their corresponding coordinates on the skin 346 where ink shall be deposited, evaluate the skin changes (e.g., stretching during the tattooing process), and analyze the target tattoo site. A machine vision device (e.g., machine vision device 130 of FIG. 2, machine vision device 1600 of FIG. 21, etc.) can utilize a machine vision algorithm to compare the detected reference features and/or tattoo dot locations with a vectoral stencil drawing. In other embodiments the machine vision algorithm may be performed by a controller such as a controller (e.g., controller 109 of FIG. 1B or controller 1400 of FIG. 20).

Figure 7:
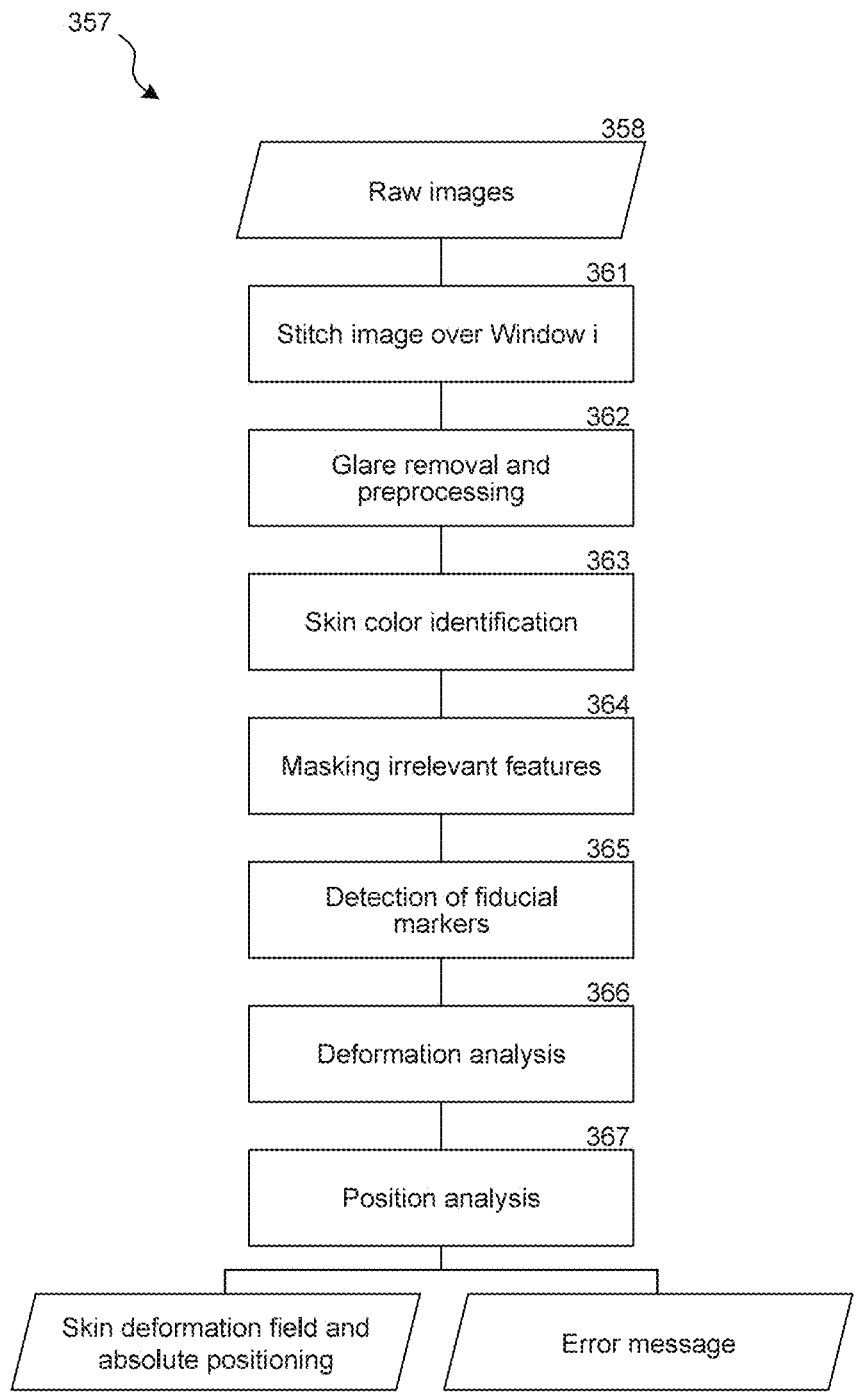
FIG. 7 is a block diagram of machine vision process in accordance with an embodiment of the disclosure.

FIG. 7 is a flow chart of a method 357 for calculating position and/or deformation field in accordance with an embodiment of the disclosure. For example, the method 357 can be used in step 323 of FIG. 3C and techniques discussed in connection with FIGS. 4-6B. In step 358, the system can obtain raw images from an image capture device, machine vision device, or other device configured to capture images. The resolution of the images can be selected based on the resolution of the stencil or other criteria.

In step 361, for a given position of the contactor, images acquired by the image capture device or machine vision device may be processed (e.g., combined, stitched together, etc.) to form an image of a portion or the entire area exposed through the contactor window (e.g., window 344b of FIG. 6A).

In step 362, the image may be preprocessed to remove, for example, light glare, reflection, shadows, and/or any variation of illumination on the skin. In one embodiment this step may be performed by color normalization.

In step 363, the preprocessed image may be analyzed to identify the colors of (i) the skin and (ii) the stencil fiducial marks as they appear on the skin. In one embodiment, color identification in step 363 may be achieved by principal component analysis (PCA) in the color space of the preprocessed image. In step 364, any features that are not relevant to the deformation and position detection steps (for example, previously applied tattoo ink, residual ink on the skin, blood, moles, hair, hair roots) may be identified on the image and masked to improve the accuracy of these algorithms downstream (steps 365-367). In one embodiment, the identification may be based on comparing the color of the image pixels to the colors of the mentioned features. In another embodiment, these features may be identified using an AI-based feature detection algorithm.

In step 365, stencil fiducial markers are detected 341b (FIG. 6B) and their size, shape and/or location on the image are determined. The contrast and accuracy of this detection may be improved based on, for example, the colors of (i) the skin and (ii) the stencil fiducial marks as they appear on the skin as identified earlier in step 363. In one embodiment, the location of the fiducial markers may be identified by filtering the image with a convolution matrix (kernel), followed by finding the peaks in the filtered image. The located fiducial markers on the image may then be further analyzed to identify their size and shape, for example, using other kernels to measure feature size and shape, or by performing pixel-level procedural analysis. In another embodiment an AI-based feature detection method may be used to identify and locate the fiducial markers on the image, based at least on their color, contrast, and/or shape. For example, a convolutional neural network (CNN) may be used for AI-based identification. The training dataset of the CNN may consist of a large number of synthetically-generated images, each showing a patch of skin with an applied stencil, as would be viewed by the machine vision device, in various states of deformation, light illumination, and skin conditions (color, creases, folds, presence of moles, hair roots etc.), wherein location, size and shape of the fiducial markers on the image are readily known by the image-generating algorithm. The CNN may then be trained by comparing its output to the known location, size and/or shape of the fiducial markers. In either method, confidence indices may be calculated for each marker detected on the image, to quantify the confidence in the detected location, size and shape.

In step 366, a deformation algorithm identifies the deformation of the skin 347 (FIG. 6B) within the contactor window 344b (FIG. 6B) by comparing the fiducial markers 341b detected on the deformed image (FIG. 6B) to the fiducial markers 341a on a reference (undeformed) stencil image 338a (FIG. 5A). In one embodiment, the deformation of the skin may be represented by a vector field (or by multiple vector fields for different regions) parameterized by a certain number of coefficients. An alignment score can be calculated for a given deformation field produced by a given set of coefficients, which may be based on the numbers of successfully-aligned and failed-to-align markers between the reference image (FIG. 5A) and deformed images (FIGS. 5B-6B), and/or the overall degree of overlap of markers between the reference and the deformed image. In this embodiment, the algorithm can identify the correct deformation field by finding the coefficients which produce the highest alignment score. The values of the deformation field coefficients may be restricted to a physically reasonable range to facilitate the search. If the lattice consists of an ordered arrangement (grid) of fiducial markers, the search may be informed by a periodicity analysis of the deformed image, for example, using Fourier analysis. In another embodiment of the deformation algorithm, a deformation field may be sequentially or locally constructed based on finding pairs of neighboring markers on the deformed image and analyzing their relative positioning with respect to each other, to quantify the local deformation and rotation of their neighborhood. This sequential analysis may begin from the fiducial marker with the highest confidence index. Different regions of the image may be analyzed separately and stitched or bridged together by making use of parameterized deformation vector fields (as in the previous method) to represent the deformation of each region. The result may further be processed by using a minimization method fitted to a physically acceptable deformation/displacement field. As a result, the output of step 366 is a deformation field, which describes the displacement of each marker on the deformed image with respect to the reference image (e.g., image in window 344a of FIG. 5A), and may be used, along with the detected contactor position (step 367), to map the coordinates of tattoo dots on the reference image to their target coordinates on the skin measured with respect to the contactor window.

In step 367, the collection of identified fiducial marks are individually analyzed to detect the portion of the encoded pattern exposed through the window 344b (FIGS. 6A and 6B). The detected pattern 342b (FIG. 6B) is compared and matched to a similar pattern in the complete reference stencil 338a (FIG. 5A), wherein the best match may indicate the most likely position 344a (FIG. 5A) of the contactor window with respect to the tattoo design 340a (FIG. 5A). A confidence index of the identified position may be determined, in one embodiment, by comparing the quality of the best match to the second-best match on the reference stencil or by other methods related to uncertainty quantification. If the confidence index is found under a critical threshold, the machine may attempt to first improve image acquisition by repeating the cleaning operation of the tattoo process. If the confidence index is still found lacking, the machine may be stopped by generating an operator error. The stopping procedure is detailed below. The above features and techniques can be incorporated or be used with features and techniques discussed in connection with FIGS. 11A-11D.

The machine vision technology discussed herein and in connection with FIGS. 6 and 7 may be used to achieve high-precision tattooing using, for example, robotic tattoo arms. Machine vision systems may be used to detecting surface topology of the body part where the tattoo is to be performed, in order to guide a tattooing robotic arm (with rotational and translational degrees of freedom) on the tattoo zone. A digital 3D representation of the surface of the body part (or the local vicinity of the tattoo area) may be constructed, such that relative location and orientation of the skin surface may be calculated with respect to the location and orientation of the tattooing head on the robotic arm. This 3D representation may be constructed by comparing images from multiple cameras (e.g., passive stereo vision), by projecting fiducial light or laser on the surface with a known pattern and detecting the correspondence of the pattern on the camera image to extract the depth information (active stereo vision), or by a combination of multiple cameras and pattern-projection in a hybrid approach. The machine vision device (or other optical analysis and machine vision systems disclosed herein) can include such multiple cameras, as discussed in connection with FIG. 21.

A 3D surface representation may also be constructed using point-wise distance measurement and mapping systems, such as LiDAR. The 3D point cloud collected from such systems is then used to construct a continuous model of the skin surface. The digital 3D representation of the skin surface may help actuating the automated machine to position the machine tattoo head in the vicinity of the tattoo zone and approach it with the proper angle (both the angle of the head and angle of approach), that is, close to normal or with an appropriate angle to the normal to the skin surface in the vicinity of the dot to be tattooed. This may be of interest when the body part is not held in a plane or displays a complex geometry in which the tattoo area may not be generally flat or cannot be flattened. A contactor may not be used for the flattening of the skin if such 3D model of the body part is generated that clearly identifies the normal to the skin in the vicinity of all the positions to be tattooed. However, our preferred embodiment may include a contactor in order to increase the stability of the skin where the tattoo is to be performed and to increase the positioning resolution. A ranging mechanism, which may be contact-less or involves contact, such as laser, ultrasound or feeler rangefinders may further be used to identify the skin to needle tip distance with high accuracy (less than 50 μm, 75 μm, 100 μm). The measured tattoo-head-to-skin distance may be used in combination with the puncture setting from the dot parameter table (i.e., needle extension measured beyond surface of the skin), to calculate the total extension of the needle that will deposit ink at the correct depth in the skin. The machine vision device disclosed herein (or other optical analysis and machine vision systems disclosed herein) can include LiDAR sensors, multiple cameras, light emitter (e.g., lasers), scanners, projectors, etc.

A mapping method, such as the stencil-based machine vision technology explained in FIGS. 5A-6B and 11A-11D, can be used (i) to map dots on the reference tattoo design to points on the skin surface and (ii) to account for any deformation of the skin if the skin is not tattooed in its relaxed configuration, and (iii) to achieve a high tattooing resolution and relative spatial accuracy in the order of ~50 um. High-accuracy mapping may be also be achieved based on other embodiments of the machine vision methodology, for example, rather than a stencil, based on the detection of (i) skin natural fiducials (such as moles, creases, folds, hair roots, etc.) and other naturally present dermal features or other sub-dermal features such as blood vessel networks which may be visible in some parts of the electromagnetic (EM) spectrum, or (ii) other synthetic fiducials transferred to the skin or projecting a pattern of light or laser on the skin to serve as fiducials. In the same manner as in FIGS. 5A-6B and 11A-11D, these fiducials may be used by the machine vision algorithm to identify the target locations (e.g., target puncture locations) on the skin while compensating for skin deformation. The reference state of the skin fiducials which is used in the deformation algorithm may be collected by an initial scan of the body part in a relaxed state, performed before the tattooing operation begins. The machine vision technology can be used to determine relationships between changes to the skin and used to select one or more puncture sites based on the determined relationships to reduce dot placement deviation when the skin is in a natural state.

The 3D model of the skin surface (the global geometry of the body part) may also be used for this mapping in certain cases, however, it may not provide high positional accuracy, especially on nearly-flat or smooth surfaces unless used in combination with skin fiducials as described above. One embodiment of a hybrid localization and mapping of the tattoo area may be performed using other depth finding or 3D topology/surface reconstruction methods such as lidar, laser, ultrasound ranging or any other technique that may grossly identify the location of the body part as well as generate a three-dimensional, dynamically updating model of the skin surface. For instance, a single camera may be used to map the body part in three dimensions by adding a projected grid on the body part using a projection apparatus. The movement of the dynamically updating model of the skin and body part may be used to provide an additional layer of safety by identifying when the tattoo area is shifted away from the needle tip. The needle may then be retracted and the machine may reposition itself to realign the tattoo mechanism with the tattoo area to resume tattooing. The skin may also be flattened locally, such in the use of a contactor, and the local vicinity of the tattoo area only evaluated on a flattened area. Accordingly, 3D modeling of the skin surface can be used to compensate for skin changes.

The stencil-based machine vision technology described in FIGS. 5, 6, 7 may be used within an augmented reality (AR) framework, which allows the customer to view, dynamically-modify and confirm the placement of the tattoo design on their body. In some embodiments, the outline of the tattoo design (e.g., design 340a in FIG. 5A) is not included in the transferred stencil, and instead AR will be used to virtually overlay the tattoo design on the body part where the stencil is applied. In one embodiment of this AR framework, a high-resolution camera is used to view the body part and its video stream is processed by a computer (or other processing device) where the digital tattoo file is loaded. The computer or controller performs the machine vision algorithm (e.g., algorithm described in FIG. 7), and upon detection of the stencil in the image(s), it is able to map the dots in the tattoo design onto the streaming camera image(s), while accounting for any deformation or curvature of the body part. A high-resolution, realistic render (simulation) of the tattoo design, which may represent the different colors in the tattoo design, account for the appearance of diffusion and fading of ink over time, etc. is generated and overlaid on the camera image using this mapping. The processed stream of image(s) can be displayed on a large screen or display for viewing by the client, where the images may be mirrored (flipped horizontally) to mimic the feel of a mirror. The client may be provided with a controller (for example, a touch-screen interface, mouse, or other inputs discussed in connection with FIG. 20) which feeds into the machine vision (MV) software to dynamically-manipulate the placement of the tattoo design with respect to its original location on the reference stencil. The modifications made by the client are processed by the MV algorithm during the render, and reflected on the screen in real-time. This manipulation may allow for rotation and translation, and in some cases scaling of the tattoo design, with the requirement that the entire design remains within the bounding box of the stencil fiducials (341a in FIG. 5A). After the client decides on a placement of the tattoo design, they may confirm their choice on the interface, which may be time-stamped, digitally saved and may constitute a digital signature. Parameters of transformation that represents the updated position (translational and rotational displacement and scaling with respect to the original position) are appended to the digital tattoo file, or transferred into the automatic tattoo machine by other means. During the tattooing operation, the transformation parameters are used to update the coordinates of all tattoo dots in the tattoo file, resulting in the desired placement of the tattoo on the skin. The above methodology of previewing, dynamically-modifying and confirming the placement of a tattoo has the following advantages over static stencil-based previewing methods: (i) the client is able to modify the placement of the tattoo design to their preference, (ii) the AR-based method potentially saves time by avoiding repeated stencil applications, (iii) it minimizes risk of future disputes and maximizes client satisfaction related to the overall aesthetic look of the tattoo on the body part, as it provides realistic simulation of the final tattoo design on the client's skin, (iv) it provides a multi-color preview of the tattoo design which is not possible with conventional stencils used in tattooing, and (v) because there is no obstructing tattoo outline (340a in FIG. 5A) on the stencil, the information content of the encoding-pattern (342a in FIG. 5A) is maximized, which increases the accuracy, precision and operating confidence of the MV algorithm, and reduces the risk of error.

Another embodiment of the AR framework may use AR googles worn by the client. The googles may be utilize a built-in camera, whose video stream is processed using MV algorithms, as described herein, and the design is rendered on the body part based on the dynamically-chosen parameters of placement. In this embodiment, the processed images with the rendered design can be fed into the googles for an AR experience, which displays the tattoo on the client's body. In some embodiments, simulated images of the tattoo design viewed by the client. The simulated images of the tattoo design can be overlaid on the identified target site in images of a site. Simulated images of the target site showing the tattoo design on the subject's body part can be viewed by the subject via a display, AR googles, display mechanism, computer, mobile device, or another viewing device. In some embodiments, a rendering of a tattoo design is mapped and projected (e.g., via a light-based projector) on the skin. This can provide pre-visualization of the design with or without application of any stencil. If a stencil is applied, the simulated images can be keyed and positioned with the applied stencil. The system can receive user input via a user interface and generate operations to modify a tattoo design based on the user input, and the system can modify the appearance of the tattoo design based on the simulated images of the target site. The modification of the tattoo design can include translating, resizing, rotating, stretching, cropping, adjusting the color, etc. The pre-visualization can be performed prior to visiting a studio or retail location and/or at the studio or retail location using, for example, a mirror-LCD, AR googles, an LCD monitor, a mobile device, a light-projection-based system, etc. Visualization can also be performed during the tattoo process to visualize section(s) of the tattoo to be applied.

Another embodiment of the AR framework may use projection of light to simulate the tattoo design directly on the client's skin, rather than displaying the render on a screen. In this embodiment, the camera is used to collect images of the body part and the MV algorithm maps the design with the appropriate deformation to comply with the body part, as explained before. A render of the design is fed into a light-projecting device, which is placed very close to the camera, and facing the same direction. The focal length of the projector could be automatically adjusted by the MV algorithm, by comparing the detected size of the stencil on the camera image to the reference stencil, and calculating an approximate distance to the body part based on this comparison. Any differences in the axes of view of the camera and the projector, may be accounted for when constructing the rendered image, to project the design with the right direction, orientation and scaling on the client's body. In some embodiments, multiple AR frameworks can be used. For example, the machine vision system can analyze a body part or target site and determine which air framework may provide the optimal client experience. The AR output can be compared to reference AR output to confirm visual accuracy. AR components can communicate with controllers disclosed herein via one or more wireless connections (e.g., via a Bluetooth connection, local Wi-Fi connection, local area network, etc.), wire connections, or the like. In some embodiments, simulated images of the tattoo design can be generated. The simulated images of the tattoo design can be overlaid on the identified target site in images of a site. Simulated images of the target site showing the tattoo design on the subject's body part be viewed by the subject via a display, AR googles, display mechanism, computer, mobile device, or another viewing device. This can provide previsualization of the design with or without application of any stencil. If a stencil is applied, the simulated images can be keyed and positioned with the applied stencil. The system can receive user input via a user interface and generating operations to modify a tattoo design based on the user input and can modifying the appearance of the tattoo design on the simulated images of the target site. The modification of the tattoo design can include translating, resizing, rotating, stretching, cropping, adjusting the color, etc.

Tattooing Apparatus with Frame and Contactor

Figure 8:
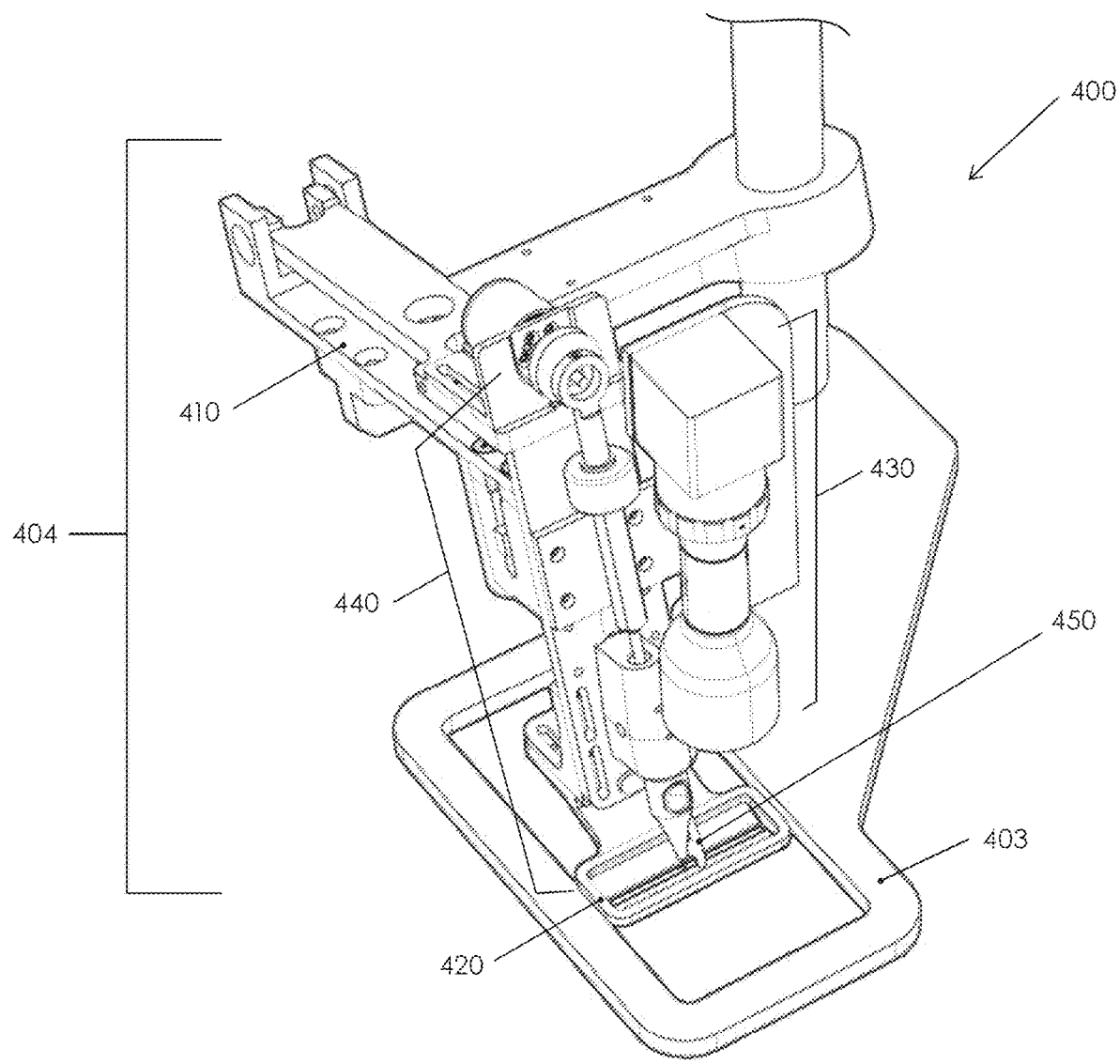
FIG. 8 is a schematic isometric view of a tattooing system in accordance with an embodiment of the disclosure.

FIG. 8 is an isometric view of another embodiment of a tattooing apparatus 400. The description regarding tattoo apparatus 100 can generally apply to tattooing apparatus 400 as well. For example, in one embodiment, tattooing apparatus 400 may comprise of a tattoo frame 403, a tattoo shuttle 404, an arm 410, a contactor 420, a machine vision device 430, a needle structure 440, and a suction system 450. Additionally, tattooing apparatus 400 may comprise more or fewer other components including but not limited to one or more motors, one or more actuators, one or more controllers, one or more gantries, a rest surface, a cantilevered tattoo machine, a needle cartridge, a needle, a plunger, a spring, a piston, a cam, an imaging device, a lens, etc. In some embodiments, the tattooing apparatus 400 can include one or more controllers, motors (e.g., drive motors, stepper motors, etc.), gantry devices, linear slides, rails, sensors (e.g., position sensors, accelerometers, etc.), or the like. In some embodiments, tattooing apparatus 400 can work with one or more separate controllers to form a tattooing system. Tattooing apparatus 400 can be configured based on desired characteristics for a particular tattooing process and may utilize any and all methods and/or components consistent with the present disclosure.

Marketplaces, Tattoo Selection, and Application

Figure 9:
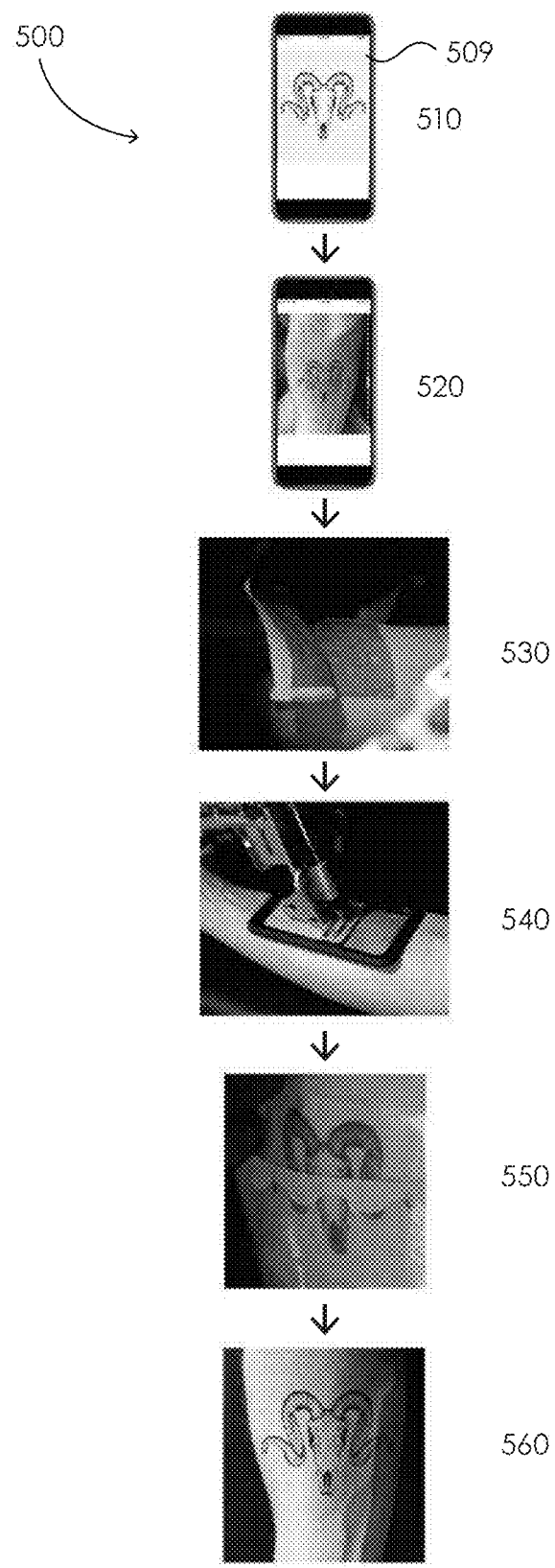
FIG. 9 is a block diagram of an embodiment of a tattoo selection and application process in accordance with an embodiment of the disclosure.

FIG. 9 is a block diagram of an embodiment of a simplified tattoo selection and application process 500. A subject may browse and/or select a design 510 from an online tattoo marketplace. In one embodiment, the subject may browse and/or select a design 510 from the online tattoo marketplace using a device 509 (or controller 108 of FIG. 1B), which may be, for example, a personal handheld device, smartphone, or a computer. The browsing and selection 510 may be done via a mobile app and/or website that allows access to the online tattoo marketplace, through which subjects may perform actions including, but not limited to, browsing, selecting, saving, rating designs, uploading, creating a profile, booking appointments, participating in auctions, or buying. In one embodiment, the online tattoo marketplace may be a global online tattoo marketplace where artists or users may upload, license, and/or sell their designs irrespective of their physical location. Artists may be paid a royalty based on selection and/or licensing of their designs by subjects through the app and/or website. Browsing, selection, and payment process may vary by location, as well as, by individual artist.

After browsing and selection 510, the subject may preview the selected design via augmented reality. In one embodiment, the subject may preview the selected design 520 via the device 509 using augmented reality to visualize how the design may look on a desired area to be tattooed. Augmented reality is a form of reality that has been adjusted in some manner before presentation to a user, which may include, e.g., virtual reality (VR), passthrough augmented reality (AR), mixed reality (MR), hybrid reality, or some combination and/or derivatives thereof. Augmented reality content may include completely generated content or generated content combined with captured content (e.g., realworld photographs). The augmented reality system that provides the augmented reality content may be implemented on various platforms, including a head-mounted display (HMD) connected to a host computer system, a standalone HMD, a mobile device or computing system, a projection system, or any other hardware platform capable of providing artificial reality content to one or more viewers. For example, a tablet or mobile phone with a camera on the back can capture images of the real world and then display the images on the screen on the opposite side of the device from the camera. The device can process and adjust or "augment" the images as they pass through the system, such as by adding tattoo designs. In some implementations, a similar process can be performed using a virtual reality or mixed reality headset, which allows light from the real world to pass through a waveguide that simultaneously emits light from a projector in the mixed reality headset, allowing the mixed reality headset to present virtual objects intermixed with the real objects the user can see. Previewing 520 may be available, for example, prior to and/or after selection of the design. Following previewing step 520, a subject may apply the design to the desired area using any of the systems or methods described. In one embodiment, a subject may undergo the tattooing process 300 using tattoo apparatus 100 or tattooing apparatus 400. In other embodiments, other embodiments of the systems and methods consistent with this disclosure may be contemplated to apply the tattoo. Application may involve utilizing a stencil 530, which may be any stencil compatible with the systems and methods described herein. Stencil application is discussed in connection FIGS. 5A-6B and stencil rejection and approval are discussed in connection with FIGS. 11A and 11B.

With continued reference to FIG. 9, the precision tattooing may be performed 540 using any system or method disclosed or consistent with this disclosure. In one embodiment, the tattooing may utilize machine vision. Following tattooing step 540, an aftercare treatment may be applied 550. In one embodiment, aftercare treatment 550 may promote, for example, healing, coloring, and/or fixation. Following the aftercare treatment 550, the tattoo may be revealed in step 560. The tattoo can be, for example, a micro tattoo, blackwork tattoo, color tattoo, realism tattoo, fine-line tattoo, or the like.

In some embodiments, a tattoo system receives a user's selection of a tattoo design and sends authorization data for the user's selection. The automatic tattooing apparatus can use the authorization data to determine whether to robotically apply a tattoo. The authorization data is sent to the user's device 509, the automatic tattooing apparatus, or both. The authorization data can include a token or credit for applying the selected tattoo design. The mobile application can manage an online tattoo marketplace that allows browsing of tattoo designs and selecting of the tattoo design. The application process 500 can include other features, steps, and processes disclosed herein.

Needle Cartridges

Figures 10A, 10B:
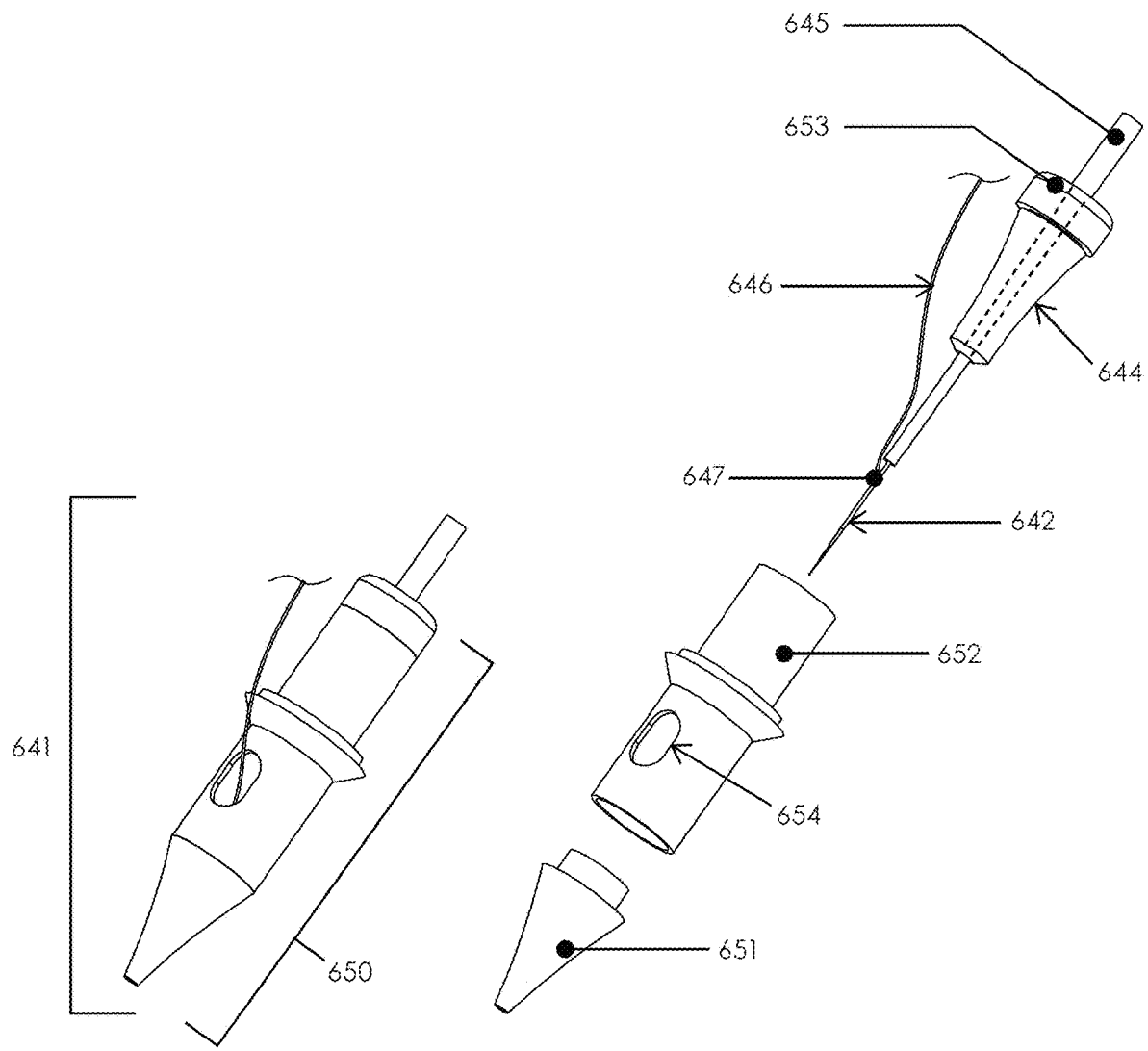
FIG. 10A is an isometric view of an embodiment of a needle cartridge in accordance with an embodiment of the disclosure.
FIG. 10B is an exploded view of the needle cartridge of FIG. 10A in accordance with an embodiment of the disclosure.

Different types of components can be incorporated into tattooing systems. FIG. 10A is an isometric view of an embodiment of a needle cartridge 641 suitable for system 76 of FIG. 1A, system 90 of FIG. 1B and system 400 of FIG. 8. FIG. 10B is an exploded view of the needle cartridge 641 of FIG. 10A in accordance with an embodiment of the disclosure. Referring to FIGS. 10A and 10B, the needle cartridge 641 may be removably coupled to the tattooing apparatus (e.g., apparatus 100 of FIG. 1B) such that switching between needle cartridges 641 may occur easily. The needle cartridge 641 may be a disposable component holding a tattoo needle and composed of the needle spring 644, plunger 645, and one or more needles 642. In other embodiments, however, the needle cartridge 641 may be suitable for refill, reuse, or limited use, and may comprise more or fewer than the parts mentioned. The needle cartridge 641 may contain at least one sensor 646 such as, for example, an electrical wire for galvanic sensing. In one embodiment, the needle cartridge 641 can comprise of a wire coupled to a non-puncturing end 647 of the needle 642 and is configured to act as a galvanic electrode that can begin measuring or exciting the skin as soon as the needle 642 contacts the skin of the subject. The sensor 646 does not need to be a wire, however, and can be any type of sensor suitable for the desired configuration.

The needle cartridge 641 may also comprise of a housing 650, which may contain, for example, a cartridge tip 651, cartridge body 652, and cartridge cap 653. The housing 650 may vary in components, size, shape, design, color, and material depending on the desired configuration of the needle cartridge 641 to be used for tattooing. In some embodiments, the sensor 646 may extend through an ink inspection hole 654 in the cartridge body 652 for coupling to the tattooing apparatus 100. The ink inspection hole 654 may, for example, facilitate inspection of proper ink quality and distribution. In other embodiments, the sensor 646 does not extend through the ink inspection hole 654 and/or from other components of the housing 650 and may be located or coupled elsewhere. The ink inspection hole 654 may be sealed or opened to ambient air and may be connected to a fluidics system for the delivery of ink or other fluids to the cartridge 641.

The needle cartridge 641 can vary in the number, size, shape, type, sharpness, and arrangement of needles 642. In one embodiment, for example, needle cartridge 641 may utilize 3RL type needles in a slightly staggered arrangement. In other embodiments, the size, grouping, number of needles in the grouping, and arrangement may vary depending on the desired configuration and design. For example, any size greater than or less than 3 (e.g., size 2, 5, 7, 10, 12, etc.) needles can be used. In another example, any grouping type, needle gauge or taper may be used (e.g., RL, RLXT, RLXP, RS*T, F, M1, M2, M1C, etc.) along with any number of needles in the grouping. The needle type, shape, number, size, grouping, number in grouping, arrangement, etc. can be selected based on the use with the systems and methods of the present disclosure. The needle cartridge 641 may be any of a variety of types of cartridges, including but not limited to, custom cartridges, third party cartridges, generally available cartridges, or any other cartridge capable of operation with the systems and methods of the present disclosure.

The ink cartridge (not shown) may be installed as a removable component to the tattooing apparatus and/or needle cartridge 641 such that switching between ink cartridges may occur easily. The ink cartridge can be configured to allocate ink via capillary action, tubing, and/or pumps at prescribed intervals from an anti-cross-contamination ink supply. In one embodiment, the ink cartridge may be a single use, disposable sterile ink cartridge with sufficient ink for a tattoo. The ink cartridges may contain different amounts and/or colors (e.g., black, red, blue, green, skin tone brown, etc.) and/or types of ink. The operator may choose one or more suitable ink cartridges depending on the tattoo. In some tattooing processes, one or more of the same or different ink cartridges may be used. In some embodiments, the ink cartridge may be suitable for refill or reuse. In one embodiment, the tattooing apparatus 100 and/or needle cartridge 641 may be configured to couple with multiple ink cartridges simultaneously. The ink cartridge type, shape, number, size, color, arrangement, etc. may vary so long as the ink cartridge is capable of use with the systems and methods of the present disclosure. The ink cartridge may be any of a variety of types of cartridges, including but not limited to, custom cartridges, third party cartridges, generally available cartridges, or any other cartridge capable of operation with the systems and methods of the disclosure. In some embodiments, the ink cartridge may be a component of the needle cartridge 641 or may be a separate component that may be coupled to the needle cartridge 641 and/or tattooing apparatus 100. The arrangement and configuration of the ink cartridge may vary depending on the desired configuration of the needle cartridge 641 and/or tattooing apparatus. The ink cartridge may be anything capable of holding and distributing ink such as, for example, an ink reservoir, ink pack, or the like.

Stenciling, Skin Analysis, and Related Technologies

FIGS. 11A and 11B are illustrative diagrams of an example rejection and example approval of stencil positioning, respectively, in accordance with another embodiment of the disclosure. In one embodiment, machine vision device (e.g., machine vision device 130 of FIG. 2) may assess stencil 710 positioning via an interrogation window 720. In one embodiment, interrogation window 720 may span a portion of the area to be tattooed. For example, in one embodiment, the interrogation window 720 can correspond to dimensions of the window of the contactor, such as contactor 120 of FIG. 2. With continued reference to FIG. 7A, interrogation window 720 may coincide with a field of vision of the machine vision device and may be configured to span the entirety of the tattoo field. In one embodiment, the interrogation window 720 may transition between multiple positions 722 of a scan zone 721 to assess positioning of the stencil 710. For example, the interrogation window 720 may be configured to detect a presence and/or absence of one or more reference features 730 and/or one or more tattoo dot locations 740. Approval of the positioning of the stencil 710 may then be based at least in part on the detected presence and/or absence of reference features 730 and/or tattoo dot locations 740. In one embodiment, the machine vision device 130 can utilize a machine vision algorithm to compare the detected reference features 730 and/or tattoo dot locations 740 with a vector-based stencil drawing. In other embodiments the machine vision algorithm may be performed by a controller such as controller 109.

FIG. 11A is an illustration of an example rejection of stencil positioning in accordance with one embodiment. For example, stencil 710 can be rejected as a result an absence of reference features 730 of the stencil 710 anticipated at particular locations within the interrogation window 720. Alternatively, stencil 710 can be rejected as a result an absence of a sufficient number of references features 730 near the targeted tattoo dot locations 740 anticipated at particular locations within the interrogation window 720. An absence of particular reference features 730 within the interrogation window 720 may be determined based at least on a comparison with reference data, such as a reference drawing, a vector-based stencil drawing, or the like. Rejection may occur when there is insufficient context within the interrogation window 720, suggesting reapplication of the stencil 710 may be required.

FIG. 11B is an illustration of an example approval of stencil positioning in accordance with one embodiment. The applied stencil 710 positioning may be approved based at least in part on a presence of reference features 730 within the interrogation window 720. In one embodiment, a presence of particular reference features 730 within the interrogation window 720 may be determined based at least on a comparison with a vector-based stencil drawing. In one embodiment, reference features 731 may be added to and/or removed from the stencil 710 to promote approval of the stencil 710 positioning. In another embodiment, stencil 710 repositioning and/or reapplication may be enough to promote approval of the stencil 710 positioning. Approval may occur when there is sufficient context within the interrogation window 720, suggesting stencil 710 may be properly positioned and tattooing may proceed. Once approved, ink can be deposited at the tattoo dot locations 740 using reference feature-based positioning in which the reference features 730 can be used as landmarks.

FIGS. 11C and 11D are simplified illustrative diagrams of an example rejected stencil and an example approved stencil, respectively, in accordance with one embodiment. FIG. 11C depicts in a simplified manner, an absence of reference features within a contour of the design (e.g., a virtually applied design) sufficient for approval. FIG. 11D depicts in a simplified manner, approval despite a limited absence of some reference features suitable for generating targeted tattoo dot locations. For example, approval may still occur if the absence of reference features and/or tattoo dot locations is sufficiently limited and/or in a non-critical region such that the tattooing process may proceed. The methods or steps discussed in connection with FIG. 11A-11D can be used for skin tracking, skin analysis, deformation compensation, and other techniques disclosed herein, such as the techniques discussed in connection with FIGS. 24A-24C.

Figure 12A:
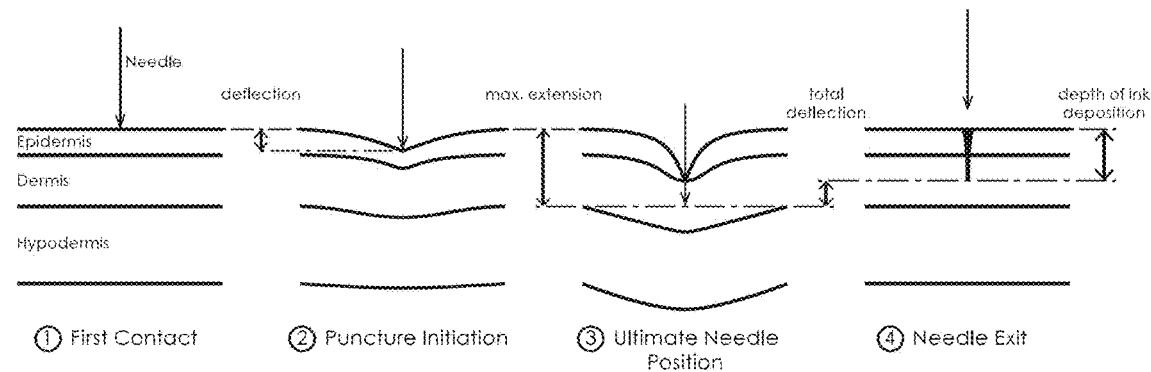
FIG. 12A is an illustrative diagram of an example puncture event in accordance with an embodiment of the disclosure.

FIG. 12A is an illustrative diagram of an example of puncture events in accordance with an embodiment of the disclosure. The needle contacts the exposed skin surface and begins to puncture the epidermis. The maximum extension corresponds to the needle being located at the ink deposit position. After depositing ink, the needle is pulled out of the skin. The depth of ink deposition can be determined based on the position at contact, the position at initial puncture, the position at maximum extension, and/or the angle of attack of the needle, as discussed in connection with step 310 of FIGS. 3A and 3B.

Figure 12B:
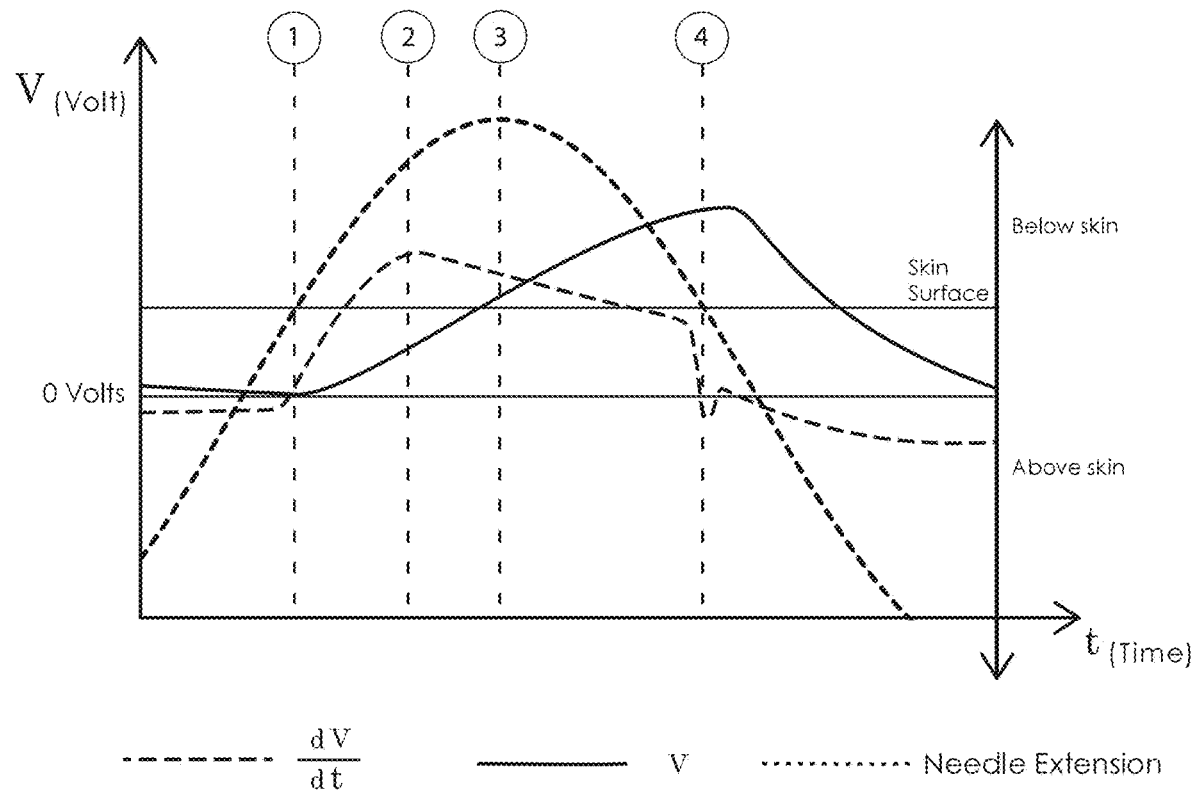
FIG. 12B illustrates a conductivity curve as detected by a galvanic sensor and data curves in accordance with an embodiment of the disclosure.

FIG. 12B is an illustrative conductivity signal of one embodiment utilizing a galvanic sensor and its first derivative with respect to time for a single puncture. Additionally, the needle extension may be obtained using the measurement from an angular encoder (e.g., an angular encoder on the needle motor 111 of FIG. 2) or other sensor. In general, the puncture events 1-4 are detectable by determining the extrema of these three illustrated curves. Puncture event 1 corresponds to initial contact. Puncture event 2 corresponds to puncture initiation. Puncture event 3 corresponds to ultimate or maximum depth needle position. Post puncture area 4 corresponds to post puncture needle exit. Example puncture events are described in detail below.

The puncture events in accordance with an embodiment are identified using an algorithm identifying the local extrema in the conductivity signal during puncture and the local extrema in the first temporal derivative of the conductivity signal during puncture. The initial contact is identified when conductivity becomes non-zero and the first temporal derivative of the conductivity signal becomes non-zero. This is because the needle closes the electrical circuit formed by the skin and the electrodes when the needle is in contact with the skin. The position at initial puncture is identified by a trend artifact in the first temporal derivative of the conductivity signal following initial puncture. This change in trend is observed in the first temporal derivative of the conductivity signal because of the shift from surface conductance to subdermal conductance.

When puncture of the epidermis finally occurs, the needle becomes in contact with the inner tissue which is more conductive than the outer layer of the epidermis, while the surface of the skin may be conductive, which results in an increase of bulk conductivity and a decrease of surface conductivity.

The position at maximum extension is identified by the analysis of the position of the needle using the needle motor 111 of FIG. 2 angular encoder with a known alignment when the needle is at its deepest setting. The signal from this encoder can be superimposed with the signal from the galvanic response to synchronize the temporal and positional signals. The position of the needle may be calculated using the equation for an eccentric cam. The post puncture event is identified when the conductivity signal and the first temporal derivative of the conductivity signal suddenly reduce. This is because the needle is losing contact with the tissue.

The conductivity signal output can be analyzed to determine additional information, including the tissue characteristics (e.g., mechanical properties of the tissue, electrical properties of the tissue, or thickness of tissue layers), performance of the tattoo system, or the like. The number and pattern of locations at a targeted area that are analyzed can be selected based on the characteristics of the tattoo to be applied at the target area. For example, the number of locations can be increased or decreased based on how the tissue characteristics vary across the target area.

The techniques discussed in connection with FIGS. 12A and 12 B can be used to determine first contact, puncture initiation, needle position, needle exit, and other puncture events based on data from other sensors disclosed herein. The puncture force used to drive a needle through each layer of skin can be monitored to identify such events. This is because each layer has different mechanical characteristics that can be identified using analytics and AI based algorithms disclosed herein. Puncture force versus displacement curves can be generated to identify the events of interest. Optical sensors, pressure sensors, logical sensors, or combinations thereof can be used with the puncture force data to identify the events. In other embodiments, sensors can noninvasively analyze sites along the skin to detect skin characteristics. The sensors can be ultrasound sensors, optical sensors (e.g., near infrared sensors, infrared sensors, etc.), acoustic sensors, or the like. In some embodiments, both noninvasive and invasive techniques are used to analyze the skin. Results from both techniques can be compared and used to generate predictive skin thicknesses at various locations along the site.

Figure 13:
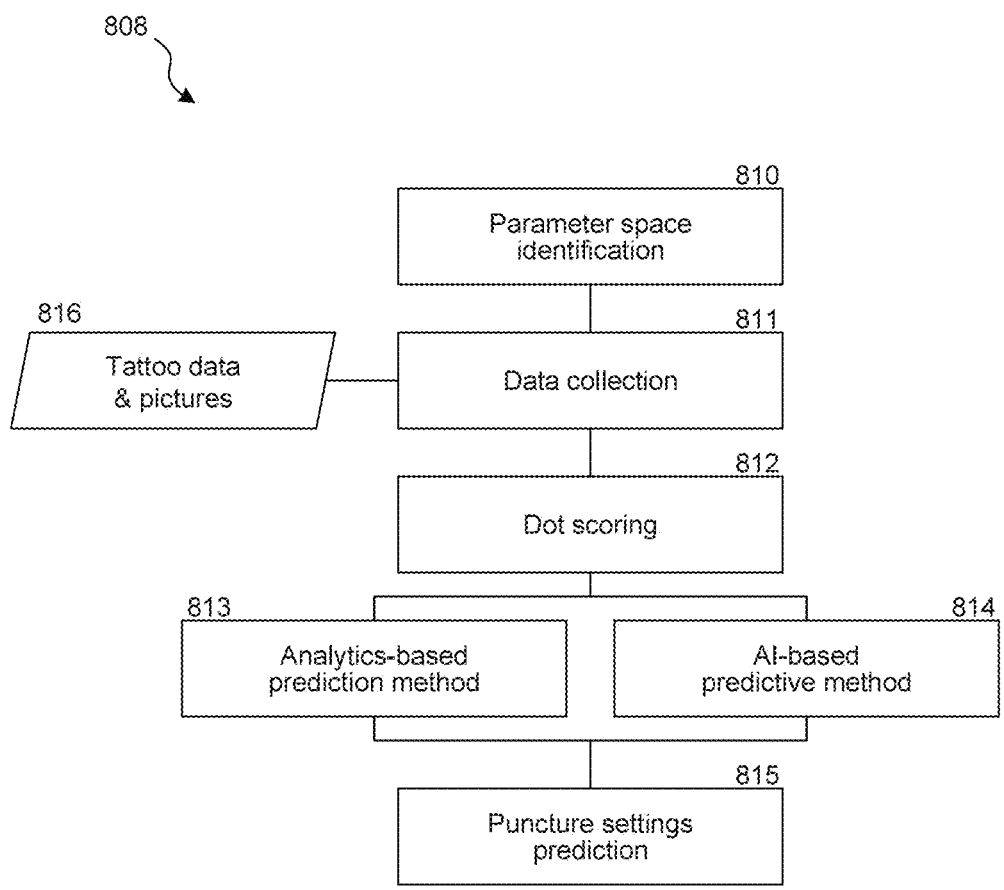
FIG. 13 is a block diagram of steps of a puncture setting prediction procedure in accordance with an embodiment of the disclosure.

FIG. 13 is a flow chart of a method 808 for acquisition and usage of a training set for the development, experimental calibration, and/or operation of a method for sensor-based control of needle extension during tattoo ink deposition. In step 810, parameter space is identified by, for example, identifying internal and external variables or properties which may influence the visual outcome of a tattoo dot. The internal variables can include: (i) needle extension, (ii) number of punctures per location, (iii) type and geometry of the needle, and/or (iv) type of the ink. Among these, (i) and (ii), are the puncture settings, which may be controlled by an algorithm based on sensor data during tattooing operation. The external variables or properties can include: geometric properties of the skin, such as thickness of its various layers and physical properties of the skin, such as mass density, water content, presence and properties of the supporting (backing) tissue, such as bone or muscle, age, race and gender of the person, (viii) body mass index, and/or and body hydration. The variables for the parameter space can be selected based on the functionality of the tattooing system, tattoo to be applied, or the like.

In step 811, data 816 can be collected by, for example, performing one or more experiments on a set of participants to identify the internal and external variables that influence the puncture sensing and ink deposition processes, and to find the relations or correlations between these variables. The participants and internal puncture settings can be chosen to increase or maximize the range of internal and external variables. The experiments can involve administration of wet (inked) punctures on the skin as well as dry punctures in the vicinity of the wet punctures. The experiments are performed and the collected data can be organized in a dataset as: the puncture settings (i, ii), needle and ink type (iii, iv), meta information about the participants related to external variables (v-ix); sensor data from the dry puncture experiments (x), and high-definition pictures of the resulting inked dots (xi), and their numerical scores (xii) which can be calculated in Step 812. The images (e.g., pictures) of tattoo dots (xi) may be appended with additional images taken at subsequent stages of the skin's healing process. In Step 812, inked dots can be assigned numerical scores (xii) based on their aesthetic quality, which can then be used to train and validate the puncture control method. Aesthetic quality can be inputted by a user or determined using an automated scoring protocol. For example, scores may be manually (by human) or automatically (by image analysis) assigned, based on the following visual aspects: (i) diameter of the dot in comparison to the expected diameter, (ii) circularity of the dot, (iii) sharpness of the edges, or the degree of diffusion, and/or (iv) presence of blowout, or another undesirable outcome. Next, a model can be trained from the collected data to predict the dot outcome as a function of one or more puncture parameters and other internal/external variables. The model can be configured to determine or selecting needle extensions, number of punctures, needle tip configuration, and/or number of needles so as to affect tattoo dot size, aesthetic quality, color saturation, color gradient, and/or color tone.

Two alternative models are described in steps 813 and 814. In Step 813, a mechanistic model of the needle and the skin may be developed while accounting for the uncertainties in the data and input/output quantities. The input of the model may be based on data collected from one or more sensors, such as galvanic sensor data which correlates with the contact of the needle and the layers of the skin, load-cell data which correlates with the force on the needle or motor encoder data which correlates with the angular position or angular velocity of the needle. The times of individual puncture events, such as (i) first contact with skin (event 1 in FIGS. 12A-B), (ii) puncture events of individual skin layers (event 2 in FIGS. 12A-B), and (iii) needle exit from the skin (event 4 in FIGS. 12A-B), are detected from the galvanic sensor data as shown in FIG. 12B. The motor encoder data in combination with the detected times of puncture events (i) and (iii) may be used to calibrate a model of the oscillatory needle extension as a function of time. This model can be constructed by calculating the conversion of the eccentric rotation of the cam to the linear extension of the needle. This model may be used to predict the time of maximum needle extension (iv) (event 3 in FIGS. 12A-B), and the extension of the needle at the time of each puncture event (i-iii) into position of the needle tip. The distance traveled by the needle between individual events (i-iv) constitute intermediary output variables of the model, which may provide valuable information pertaining to the tattoo ink delivery. For example, distance traveled between first contact (i) and first puncture (ii) is (a) the initial deflection. The distance traveled between the times of puncture of individual layers (ii) may be correlated to the (b) thickness of these layers. The distance traveled between first contact (i) and maximum needle extension (iv) is (c) the max extension. The distance between max extension (iv) and needle exit from skin (iii) is (d) the posterior max extension. A combination of the intermediary output variables (a, b, c, d) may be statistically related to the penetration depth of the needle, the depth of ink deposition, or the tattoo dot quality (xii) in the experimental dataset. The statistical relation between the intermediary output variables (a, b, c, d) and the tattoo dot quality (xii) may be identified using a partial least-squares regression (PLS) method, or other regression methods such as standard or constrained least square approaches, regularized minimizations, principal component analysis or other. The goodness of fit, correlation coefficients, or other statistical measures of the model precision with respect to the predicted output, may be calculated from the dataset to provide a confidence index to the predictions during tattooing operation.

As an alternative to step 813, a machine-learning method, such as a neural network, could be trained in step 814 from the collected dataset, in order to predict the correct puncture settings to achieve a high-quality dot as a function of the sensor data and any available meta-information related to external variables (v-ix). In this approach, the dot score is used as the objective set and the sensors signals are the input and the puncture settings are the searched variables. The puncture events may or may not be defined as intermediary input and collected dataset may be enhanced until a statically representative dataset is obtained.

In step 815, the model developed in step 813 or 814 is used to predict the correct puncture settings which would create a high-quality tattoo dot, for each location where dry punctures are applied. The predicted puncture settings are appended to a parameter table 316 of FIGS. 3B and 3C.

Shading can be obtained by, for example, varying the needle extension, number of punctures (e.g., number of punctures at a certain position or area), amount of applied ink (e.g., volume of ink applied for each puncture event or set of puncture events), or combinations thereof. For example, shading can be achieved by varying the amount of ink that is delivered at a certain dot by depositing ink at a different depth within the skin, or by varying the number of punctures at the same position, etc. In some embodiments, a dot with more punctures will receive more ink than a dot with fewer punctures. Similarly, a dot created by shallow punctures will preserve less visible ink after healing than a dot created by deeper punctures, provided that the deeper punctures are not so deep as to result in a defective dot, for example in the case of a blowout, where ink is dispersed due to diffusion and immune response. In some instances, a deeper ink deposition can result in a more diffused dot of a lighter shade. These techniques can be used to create different shades of color. For example, an area with fewer punctures per dot can create a lighter shade than an area with more punctures per dot. Similarly, an area of the tattoo can be performed with shallower punctures to create a lighter shade than an area where deeper punctures were performed. In some procedures, both depth and puncture number per dot can be selected to achieve various shades or to compensate for other constraints in the tattooing process.

Another process for shading includes varying the spatial density of dots. For example, closely spaced dots can result in a darker shade than widely spaced dots. The pattern, pitch, and/or spacing of dots can be determined based on the desired shade of the tattoo. Dithering, ink deposition depth, and/or number of punctures per dot may be used together or individually to realize various shading in a tattoo. During tattooing operation, the puncture settings (e.g., needle extension, number of punctures, ink delivery rates, target depth, etc.) for a tattoo dot may be determined based on the target characteristic(s) (e.g., shade, color, etc.) of the dot in the artwork, which may be saved in a digital tattoo file (e.g., metadata 1217 in FIG. 19), and a method of predicting the puncture settings to achieve the desired shade, color or ink saturation, such as the method 808 of FIG. 13.

In some embodiments, predictions are generated using the analytics prediction methods of step 813 and AI-based predictive methods of step 814. The method 808 can include using output from both steps 813, 814 to determine predictions, e.g., by using confidence factors determined for one or both processes to weight a combination of the results or to select which output to use at any given time. For example, the output of the machine-learning method can include a value in a range for a puncture setting, where a difference between the value produced at the nearest of the range can be the confidence factor, and the results of the machine-learning method are only used when that confidence factor is above a threshold, otherwise the analytics-based method is used. Alternatively, the method 808 can select one of the outputs from step 813 or step 814 as the prediction. The selection can be based on analysis of the collected data and historical prediction accuracy for similar data. The model from steps 813 and/or 814 are used to predict the correct puncture settings.

A robotic tattooing system can include a portable automated handheld tattoo device. The handheld tattoo device can be conveniently carried by a user and applied to a subject. This allows tattoos to be applied at a wide range of settings, including at tattoo studios, spas, home settings, or the like. During a tattooing session, the handheld tattoo device can be manually repositioned (e.g., manually carried and placed) at desired locations.

Handheld Tattoo Device and Related Technology

Figure 14:
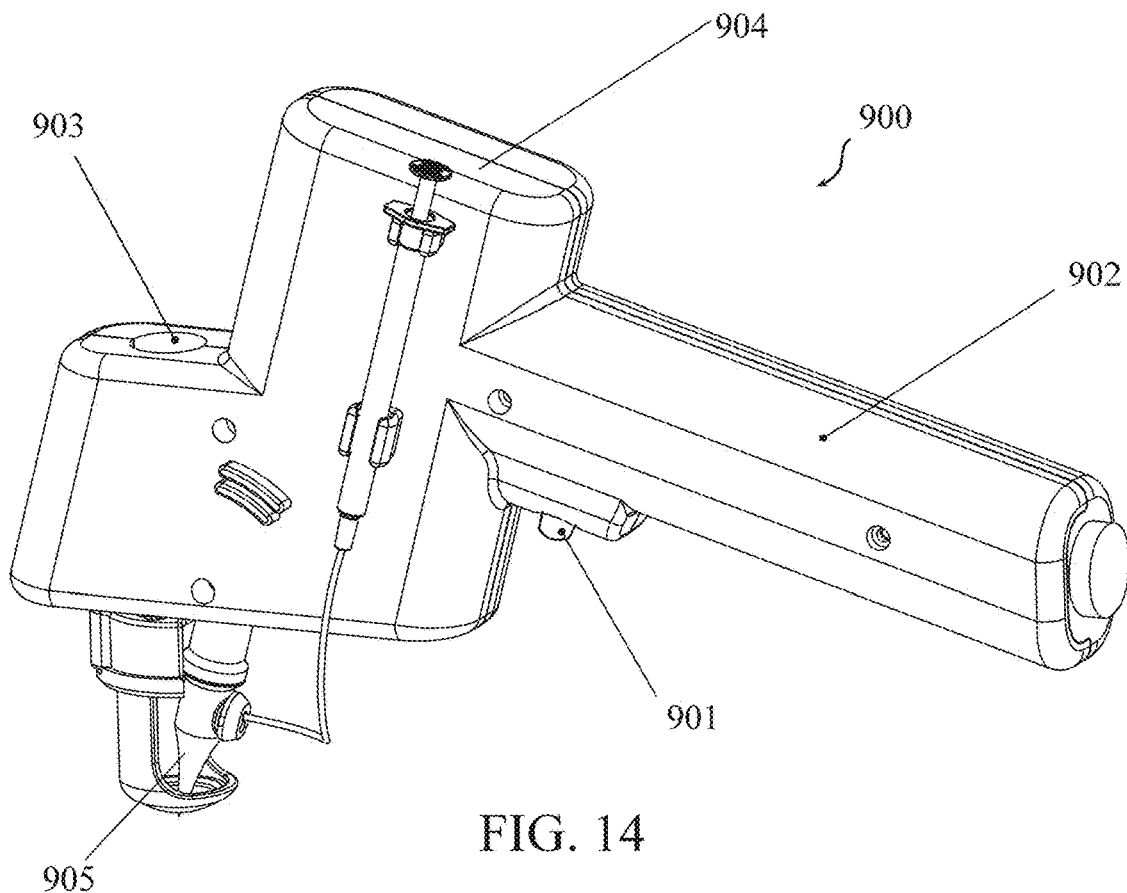
FIG. 14 is an isometric view of a handheld tattoo device in accordance with an embodiment of the disclosure.

FIG. 14 is an isometric view of a handheld tattoo device or unit 900 ("handheld tattoo device 900") in accordance with an embodiment of the technology. The handheld tattoo device 900 can include a grip or handle 902, a main body 904, and a needle assembly 905. A control element 901 can be used to control operation and can include a trigger, a push button, a switch, a finger interface, and/or an actuatable element. The control element 901 can be used to, for example, control operation of the needle assembly/actuator, start/stop a tattoo protocol, or the like. A sensor 903 can include one or more indicators, levels, accelerometers, gyroscopes, etc. In some embodiments, the sensor 903 is an indicator (e.g., one or more bubble levels) used to set or correct (1) relative positioning of the tattoo device 900 with respect to the skin surface, (2) the orientation (e.g., horizontal orientation or vertical orientation) of the tattoo device 900, or (3) the angular position of the tattoo device 900 relative to a reference plane.

Figure 15:
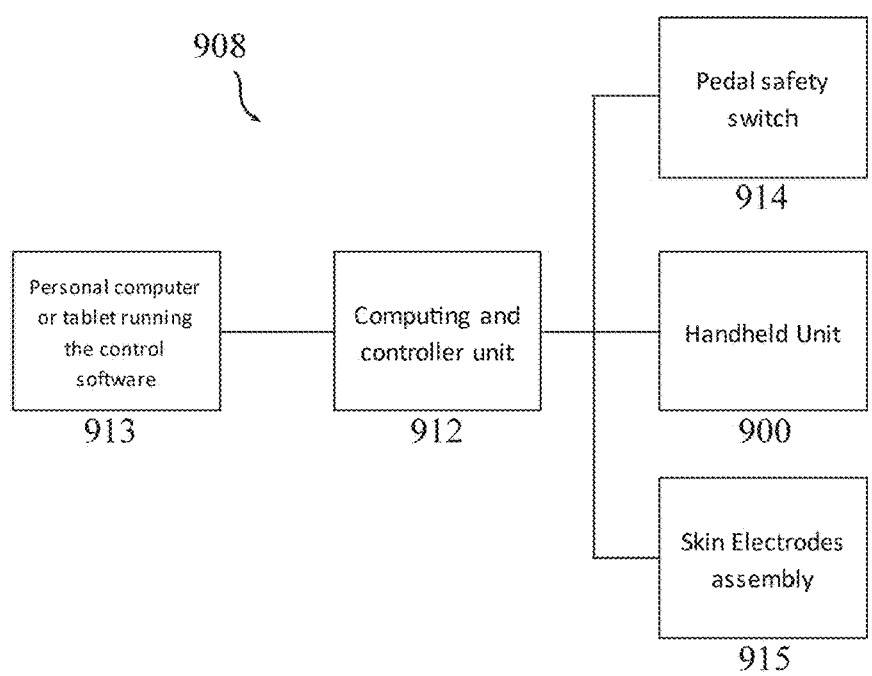
FIG. 15 illustrates a handheld automatic tattoo apparatus in accordance with an embodiment of the disclosure.

FIG. 15 illustrates a handheld tattooing system 908 in accordance with an embodiment of the technology. The handheld system 908 can include the handheld tattoo device 900, a computer and/or controller unit 913 (e.g., a PC/tablet running the control software), controller unit 912, a safety device 914 (e.g., pedal safety switch), and an electrode assembly 915 (e.g., skin electrodes). The components can be integrated into or coupled to the handheld tattoo device 900. For example, the components can be detachably coupled to the handheld tattoo device 900. The handheld tattoo device 900 can include one or more rechargeable power sources. In some embodiments, the handheld tattoo device can be powered via an external power source. The handheld tattooing system 908 can be incorporated into systems with features and functionality discussed in connection with FIGS. 1 and 21.

Figure 16:
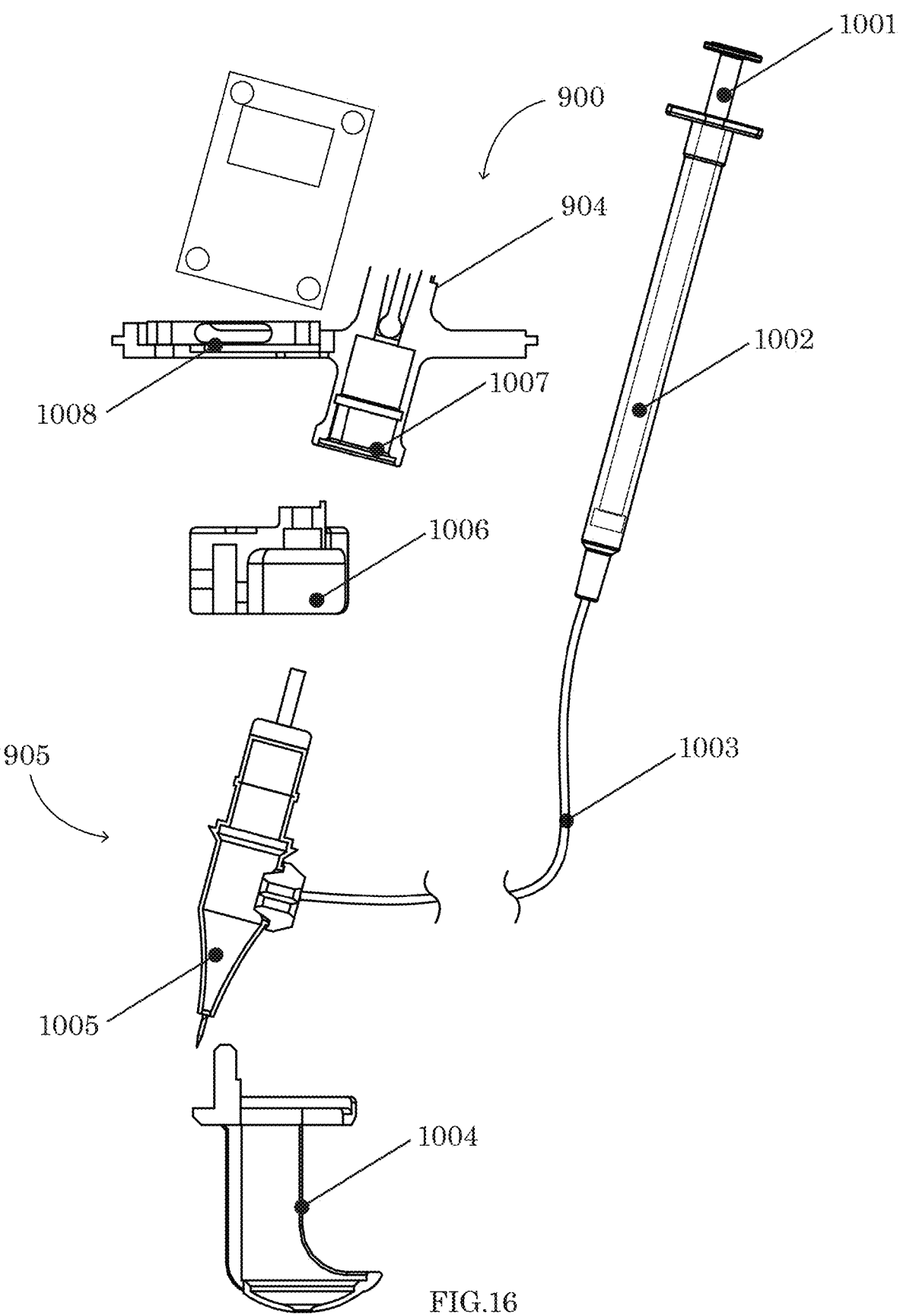
FIG. 16 is an exploded side view of a handheld device in accordance with an embodiment of the disclosure.

FIG. 16 is an exploded view of components of the handheld device 900 in accordance with an embodiment of the technology. The handheld device 900 can include a contactor 1004 (or contactor 1106 in FIG. 18C) with one or more windows or openings to facilitate visualization of the skin. The contactor 1004 can be configured to keep a region of the skin surface general flat. In some embodiments, the contactor 1004 has a generally circular shape, partially spherical shape, or cylindrical shape since only one dot or a limited number of dots may be applied at a time. In multi-needle assembly embodiments, the configuration and number of contactors and number of openings can be selected based on whether ink is applied simultaneously or sequentially by different needles assemblies.

Figure 18A:
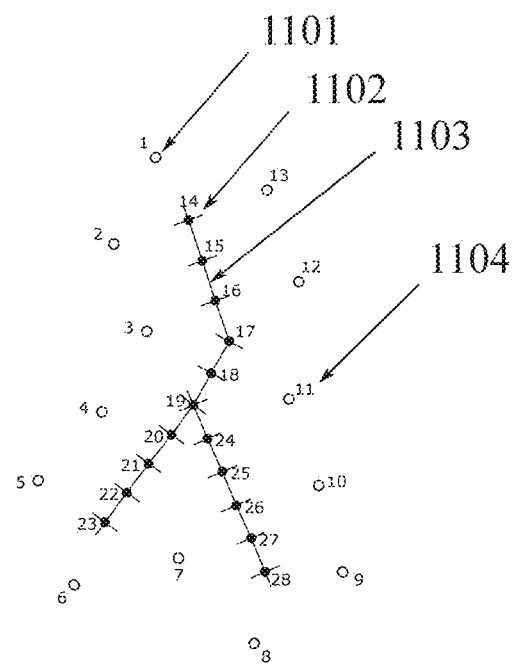
FIGS. 18A-18C illustrate a stenciling process for manual tattooing in accordance with an embodiment of the disclosure.
Figure 18B:
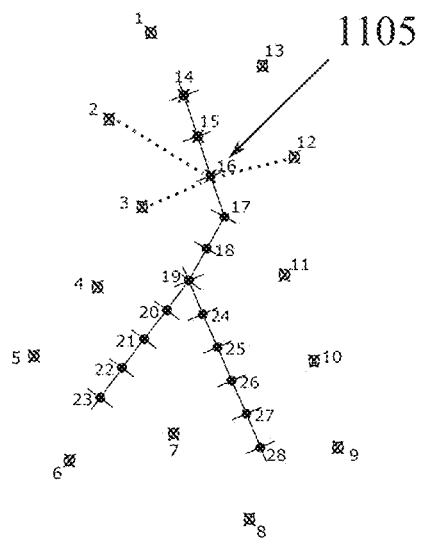
Figure 18C:
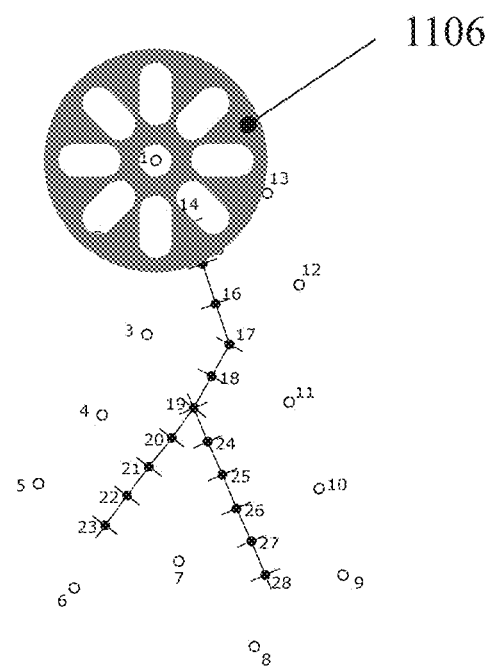

The device 900 can also include an integrated lighting system that outputs light to facilitate operator vision of the tattoo window and openings of the contactor. In FIG. 18C, the integrated lighting can be integrated in the contactor holder 1006. In some embodiments, the lighting system is installed as a removable component of the device 900 to allow repositioning of the lighting system. All or some of the components of the handheld device 900 can be encased or include a protective housing to protect the mechanism from being exposed to the patient and/or operator. A removable electrical assembly can include one or more wire harnesses used to couple the tattoo device to components, such as the control and sensing electronic box. In some embodiments, the device 900 has an integrated control and sensing electronic box, an internal power source, or the like. A pedal (e.g., a safety device 914 in FIG. 15) can be used to trigger off the actuator in case of malfunction.

Referring to FIG. 16, a load cell 1008 can be coupled to the contactor holder 1006 and to the body of the handheld tattoo device 900 in order to sense the applied pressure from the skin to the contactor 1004. The tattoo device 900 can also include one or more actuator mechanisms similar to or the same as the actuator mechanism described in connection with arm 110 and FIG. 2.

The needle assembly 905 can be inserted into an opening 1007 of the main body 904. One embodiment of the disposable needle cartridge is an integrated ink and needle disposable (or not disposable) cartridge. Such a system includes an ink reservoir 1002 holding ink that be injected in the needle well 1005 by pressing a piston 1001. A line or tube 1003 can be used to deliver the ink from the ink reservoir 1002 to the needle well 1005. Referring now to FIGS. 10A, 10B, 14, and 16, the needle cartridge of FIG. 16 and the needle cartridge 641 of FIGS. 10A and 10B can include one or more electrodes, electrode wires, sensors, or the like. For example, the cartridge 641 of FIGS. 10A and 10B can contain the electrode wire 646 that provides the needle electrode connection 647 to the rest of the system or device. With continued reference to FIGS. 10A and 10B, the needle cartridge 641 also contains a plastic piston 645 connected to the needle 642 to provide Z movement and an elastic skirt 644 that provides a seal to ink and air from the ink well as well as a spring like action on the plastic piston. When assembled, air and ink can only be released through the needle opening. The ink cartridge of FIG. 16 can include similar components and operate in a similar manner.

The ink and needle cartridges can integrate with the needle and the ink necessary to provide desired tattooing action. When inkless measurement with the needle is performed (e.g., dry puncture), the ink reservoir piston is not pressed and no ink is present in the ink well. The needle is therefore operated without ink on its surface, resulting in a puncture with no ink. When performing a tattoo with ink, the ink reservoir piston is pressed in initially until ink fills up the ink well. The ink in the ink well does not drain excessively from the needle aperture when the needle actuation is not performed due to the surface tension of the ink. In operation, the needle actuation moves ink from the ink well by coating the needle surface with ink, which allows ink to be transferred to the skin and in the skin. As the tattoo progresses, the piston of the ink reservoir is further pressed to compensate for the consumed ink as part of the tattooing process such that the ink well is always sufficiently full for tattooing. This can be realized by either sensing the ink well content or by adding a prescribed amount of ink for every, or some number of actuations of the needle. The piston of the ink reservoir can be, in one embodiment, pressed by an automated actuator, or, in another embodiment, by the operator in case of a manually operated machine.

The ink and needle cartridge system may, in some embodiments, not contain a piston to transfer ink from the reservoir to the ink well, but any other suitable mean of transferring ink from one to the other, such as a pump, capillary action, pressure differential, or piezoelectric action. The ink and needle cartridge may include multiple sub elements, each of which may or may not be disposable. The ink and needle cartridge may contain sensors and electronic components to detect ink level and to authenticate originality, quality or first usage of the ink and needle cartridge, to avoid reuse of components (e.g., ink cartridges/assemblies), quality of product and one status of product.

The handheld manually operated tattooing process can include one or more steps discussed in connection with FIG. 3A and there can be some optional differences in steps 302, 303, 304, 305, 306, 307, 310, 320, 308. The handheld manual operation can include one or more features discussed in connection with step 310 (FIG. 3B), step 320 (FIG. 3C), and processes discussed in connection with FIG. 17. Referring now to FIG. 3A, in a manually-operated embodiment of step 301, a portion of skin that will receive the tattoo is prepped by, for example, shaving (if required or desired), cleaning the skin surface, etc. In step 302, a stencil can be applied to the portion of skin. The stencil in step 302 can be similar or identical to the steps described in connection with FIGS. 18A-18C or other stenciling processes disclosed herein. The stencil can provide information about operation of the tattooing device. The stencil can include one or more markings indicating tattooing procedure information, specifying the order of operations for a manual operator to execute, post tattooing session information, or combinations thereof. In some embodiments, the stencil can provide a temporary indication of the final design that can be reviewed and accepted by the client. Artwork can be used to generate a stencil. An algorithm may be used to generate the stencil from the artwork. The artwork can be comprised of dots, lines, areas interpreted as dots, or the like. The algorithm can be selected based on the characteristics of the artwork, such as resolution of the artwork, colors of the artwork, or the like.

After applying the stencil 302 of FIG. 3A, the subject and/or operator may check the stencil 303. The subject may review the stencil application and either approve or reject the design placement. The operator may review the stencil for quality of application. In some embodiments, for example, a stencil deposition should be such that a transfer of fiducial marks is adequate to apply a tattoo using the handheld tattoo device without missing dots. If the stencil appears misplaced or the application is not accepted by client, the stencil application step may be repeated until accepted.

Following approval of the stencil application, lubricant can be applied in step 304. A variety of suitable lubricants with different viscosities and hydrophobic properties may be suitable for use. For example, a lubricant with a viscosity between, for example, 10 cps and 500 cps with hydrophobic properties to increase the contact angle between ink droplets and skin may be used. The lubricant can be chosen such that the type and viscosity of the lubricant may allow it to protect the epidermis top surface from being stained by ink and/or increase ease of removal of the ink.

Step 305 may be performed after step 304. In step 305, the handheld tattoo device can be prepared to position the disposable ink delivery system, contactor, needle cartridge and/or protective bagging on the handheld tattooing device. These accessories can be disposable for hygiene purposes. Electrodes (e.g., liquid electrodes) can be positioned on the skin by the operator within the vicinity of the tattooed skin area. The electrodes can be positioned side by side or in another pattern, with the test electrode positioned closer to the tattoo area than the reference electrode.

Following step 305, the tattoo device may perform a calibration routine. In step 306, the tattoo device can identify its internal zero reference and calibrate itself. The calibration routine can include actuating one or more actuators (e.g., actuator system) to assess correct operation in this step. In one embodiment, calibration may comprise of using an algorithm to run a diagnostic of the sensors. Additionally or alternatively, a conductivity test may be performed to confirm connection of one or more electrodes to the tattoo device and/or to the skin.

In the handheld operation, step 307 of FIG. 3A can be omitted, since positioning of the handheld tattoo device can be performed by the operator in steps 310 and 320 for each and every dot, or a subset of dots. In some embodiments, a tattoo process can include both step 307 of FIG. 3A and steps 310 and 320.

At step 310, a skin puncture property acquisition can be performed. For the manual embodiment of FIG. 3B, the operator can identify one or more markers associated with a dry puncture.

Figure 17:
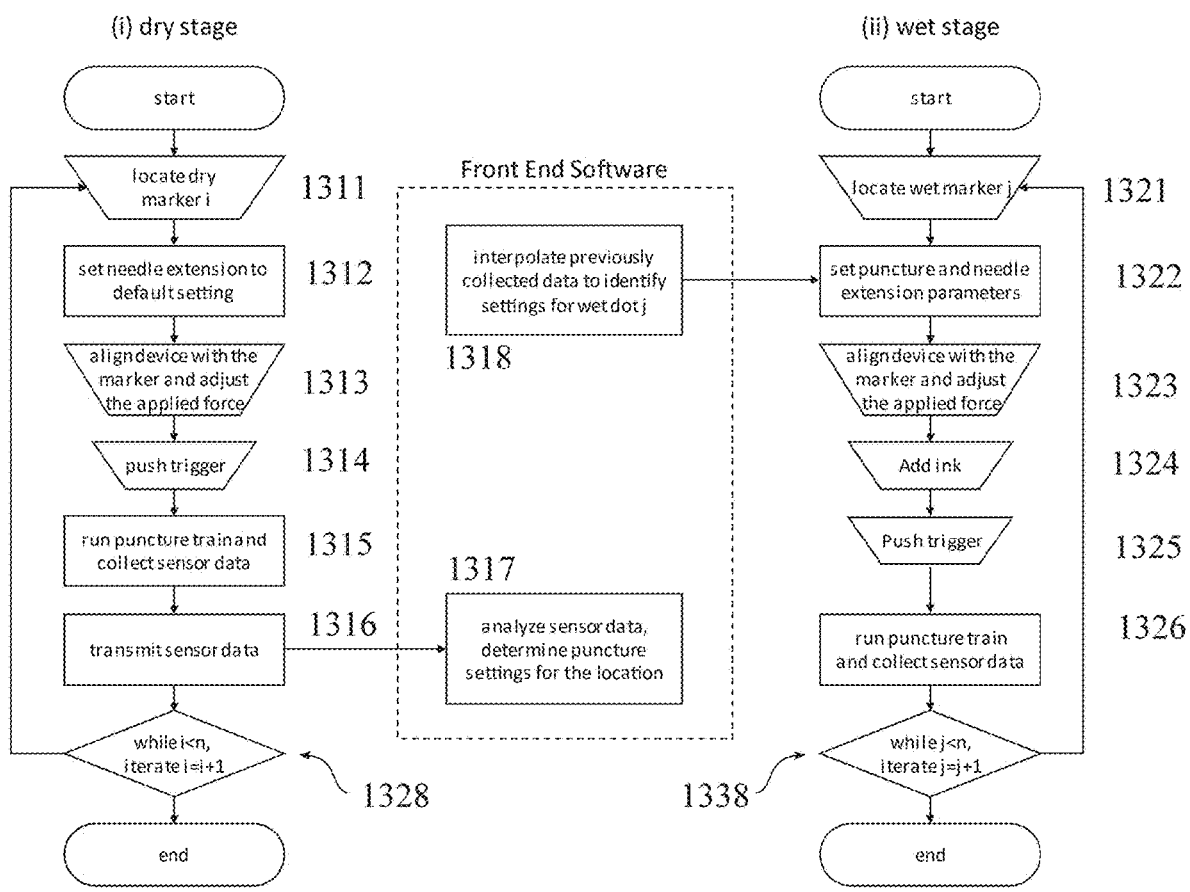
FIG. 17 is a block diagram of an embodiment of the procedure for applying a tattoo using a handheld automatic tattoo apparatus in accordance with an embodiment of the disclosure.

FIG. 17 is a block diagram of a dry stage with dry puncture and wet stage with wet puncture in a tattoo application process step in accordance with an embodiment of the disclosure. The robotic systems can perform the steps discussed in connection with FIG. 17 and discussed in connection with the embodiments of FIGS. 14-16. A dry puncture is a puncture that is formed without applying ink. For example, a needle can be inserted into the skin to form the puncture, and the needle can be removed from the skin. The locations designated to receive dry punctures are denoted by an unfilled feature 1101 in the example stencil illustration in FIGS. 18A to 18C. The unfilled feature configuration (e.g., shape, dimensions, diameter, etc.) can be an indicator for needle configuration. In one embodiment, small diameter circles indicate the use of a needle with 3 or less tips in a tight circular configuration, and large diameter circles indicate the use of a needle with 4 or more tips in a tight circular configuration. The position can either be identified by a numeral character (e.g., number 1104 as shown in FIG. 18A) applied as part of the stencil and/or through a digital representation of the tattoo displayed on the computer or tablet that runs the control software's graphical user interface. Other techniques can be used to apply the numeral character.

A control module can send a command to the computing unit of the tattoo system to configure (e.g., applying one or more settings) the tattoo device for the skin puncture acquisition in step 1312. After a setting is applied in step 1312, the operator can position the contactor window by centering the contactor with the marker in step 1313. FIG. 18C illustrates positioning of the contactor window 1106 with the stencil illustration. For example, contactor can be aligned with the dry marker numbered "1". In step 1313, the operator can also ensure that the tattoo device is properly oriented with respect to the skin surface with or without using a level element, such as the level element 903 in FIG. 14. If the skin surface is oriented horizontally, the level element can be an air bubble level element used to ensure that the contactor/skin surface are substantially parallel.

The operator can increase or decrease the pressure applied by the contactor to the skin by applying manual force. In some procedures, belts, straps, adhesive elements (e.g., double-sided adhesive tape) are used to couple the tattoo device to the subject. The tattoo device can apply a sufficient level of force to the skin to ensure sufficient contact between the contactor and the skin. The amount of force employed can be measured by one or more sensors (e.g., contact sensors, pressure sensors, load cell, etc.). The amount of force can be digitally reported by the graphical and/or sound interface of the control module. The amount of force or pressure allowed can be between two force/pressure values, a lower bound optimal force/pressure and a higher, upper bound optimal force/pressure. In some embodiments, the optimal forces are between 0 g and 10,000 g.

The control module can block the actuation of the handheld tattoo device if the force/pressure applied is not in the between the lower and upper optimal force/pressure. When the operator is ready to perform a puncture, the operator can press the trigger element, as discussed in step 1314 of FIG. 17. If the contact force/pressure is in the optimal range, the diagnostic system can report nominal operation and the handheld tattoo device can confirm applying the parameter settings from step 1312. The handheld tattoo device can proceed immediately to step 1315. In step 1315, the handheld tattoo device can perform a set of punctures (e.g., a puncture train). The depth, size, positioning, and/or pattern of the punctures can be specified in step 1312. In step 1312, the actuator(s) of the handheld tattoo device can be powered to puncture the skin. A galvanic sensor and/or other sensors in the handheld tattoo device can start measuring and recording signals related to the application of the set of punctures, the data can be buffered in the control unit and, after the puncture train (e.g., set of punctures) is partially or entirely completed, and the data can be formatted and transferred to the control module. The data can be analyzed and/or interpreted in step 1316. In some embodiments, the data is analyzed in step 1317. In step 1328, if i<n, the process returns to step 1311. The steps 1311 to 1316 are then repeated until a set or all the puncturing has been completed.

Signal detection and/or interpretation can be used to analyze data and leads to the detection of the puncture events as described in connection with FIGS. 3A, 12A, and 12B, and the device setting for performing a desired dot (e.g., a circular dot, round dot, a dot with a desired size, color, color saturation, darkness, geometric characteristics, shape, etc.) at that location marker is computed by an algorithm described herein. The device settings can be stored. The operator can then repeat the operation from steps 1311 to 1317 for each dry marker until a predetermined number or all dry punctures have been performed.

Once performed, an optimal setting obtained in step 1317 for all the dry markers of a specific dot size can be interpolated in step 1318 for all the positions associated with wet dots of the same or similar configuration (e.g., size, shape, diameter, etc.). This is exemplified for dot number 16 (dot 1105 in FIG. 18B), for which the settings can be interpolated as a combination of the information collected from one or more of dry punctures 2, 3, and 12. In one embodiment, this interpolation can be performed on different wet dot diameters than the dot diameters of the dry punctures by applying a setting conversion from one type of needle to another type of needle used to obtain different dot diameters. Wet dots are tattoo dots where a detectable amount of ink has been applied to the subject. This can conclude the step 310 (FIG. 3A) associated with the manual embodiment of the tattoo process.

In step 320 (FIG. 3A) associated with the manual embodiment of the tattoo process, the tattooing process can be performed. In the case of the manual embodiment of the tattoo process, wet dots can be applied. The operator can proceed to identify the marker associated with a wet puncture in step 1321 of FIG. 17. These dots can be marked by a filled circle in the stencil illustration in FIGS. 18A-18C. The diameter of the filled circle can indicate the diameter of the needle used. In one embodiment, small diameter circles are applied using a needle with 3 or less tips in a tight circular configuration and large diameter are applied using a needle with 4 or more tips in a tight circular configuration. The position can either be identified through a number applied as part of the stencil and/or through a digital representation of the tattoo displayed on the computer or tablet that runs the control software's graphical user interface. Settings of the tattoo device are applied in step 1322 (FIG. 17) by reading the interpolated parameters obtained in step 1318 (FIG. 17) and sending a command from the control software to the computing unit of the tattoo handheld unit. Once the settings are applied in step 1322 (FIG. 17), the operator can position the contactor window or opening by centering the contactor with the marker in step 1323. In this step 1323, the operator also ensures that the needle (or needle assembly) is properly oriented perpendicular to the skin surface (e.g., a longitudinal axis or line of action of the needle assembly can be generally perpendicular to the surface of the skin) with or without using a level indicator. The operator can increase or decrease the pressure applied by contactor to the skin by applying manual force. One of the operator's objectives can be to apply an optimal level of force to the skin to ensure sufficient contact between the contactor and the skin. The amount of force employed is measured by the load cell (e.g., load cell 1008 of FIG. 16) and the value of the load can be digitally reported by the graphical interface of the control software. The optimal force allowed is between two force values, a lower bound optimal force and a higher, upper bound optimal force. These forces can be between 0 g and 10,000 g. The control software can prevent actuation of the handheld unit if the force applied is not within a target range (e.g., between the lower and upper optimal forces).

When the operator is ready to perform a puncture, the operator triggers the ink delivery system to inject ink in the needle well in step 1324 of FIG. 17. For the initial wet dot, the needle well will be filled with ink for the first time. For additional wet dots, a sufficient amount of ink can be present in the needle well and adding more ink may be performed if necessary. When ready, the operator can press the trigger button in step 1325. If the contact force is in the optimal zone, the diagnostic system can report operation information and the handheld unit can be configured based on the parameter settings from step 1322. The handheld unit then proceeds immediately to step 1326. In step 1326, the handheld unit performs a set of punctures at the depth and number settings specified in step 1322. In this step, the handheld actuator can be powered, which results in the needle (or needle assembly) puncturing the skin. Data associated with the puncture event can be collected. This collected data is analyzed and used to confirm appropriate application of the tattoo settings. The stored interpolation settings for subsequent dots may be adjusted if new settings are desired or needed to produce desired dots. In step 1338, if i<n, the process returns to step 1321. The steps 1321 to 1326 are then repeated until all the wet dots have been applied. This concludes step 320 (FIG. 3A) for the manual tattooing process embodiment.

In the manual embodiment of the tattoo process, step 308 of FIG. 3A can be omitted as the handheld unit is not attached to the customer. The tattoo area may be cleaned and dressed with a protection layer in dressing tattoo step 309 (FIG. 3A). Additionally, a variety of aftercare treatments may be provided. Finally, the surface of the tattooing device may be cleaned with a cleaning solution so as to be suitable for subsequent use. Any disposable components may then be removed and disposed of. In some embodiments, the handheld robotic units can be attached to the customer.

As used herein, the term "disposable" when applied to a system or component (or combination of components), such as a needle, a tool, or stencil, is a broad term and generally means, without limitation, that the system or component in question is used a finite number of times and is then discarded. Some disposable components are used only once and are then discarded. In other embodiments, the components and instruments are reusable and can be used any number of times. In some systems, all of the components can be disposable to prevent cross-contamination. In some other systems, components (e.g., all or some of the components) can be reusable.

Embodiments of the stencil deposition can be designed for manual application of the tattoo. One embodiment is displayed in FIGS. 18A-18C. The stencil can facilitate tattoo application by the manual operator and to provide a proxy reference of the final design to the client. In such embodiments, the stencil can contain alignment markings 1101, 1102 and 1103 (FIG. 18A) for proper operator alignment. Numbers and text 1104 to help the operator proceed in the correct order of dots. Filled circles 1102 denote the locations designated for "wet" punctures. Unfilled circles 1101 denote the locations for "dry" punctures to be administered. Dry punctures are administered without ink, not part of the final tattoo, but used for gathering information about the skin puncture properties prior to performing wet dots. One embodiment of the stencil uses various diameters for the filled and unfilled circles to indicate the correct needle type and arrangement for the tattoo dot size by varying the dot diameter. Any other markings may be present to facilitate the operator application of the tattoo and customer validation of design and placements. Stenciling procedures can include steps discussed in connection with FIGS. 5A-6B, 11A-11D, and 18A-18C.

Digital Files, Computing Systems, and Controllers

Figure 19:
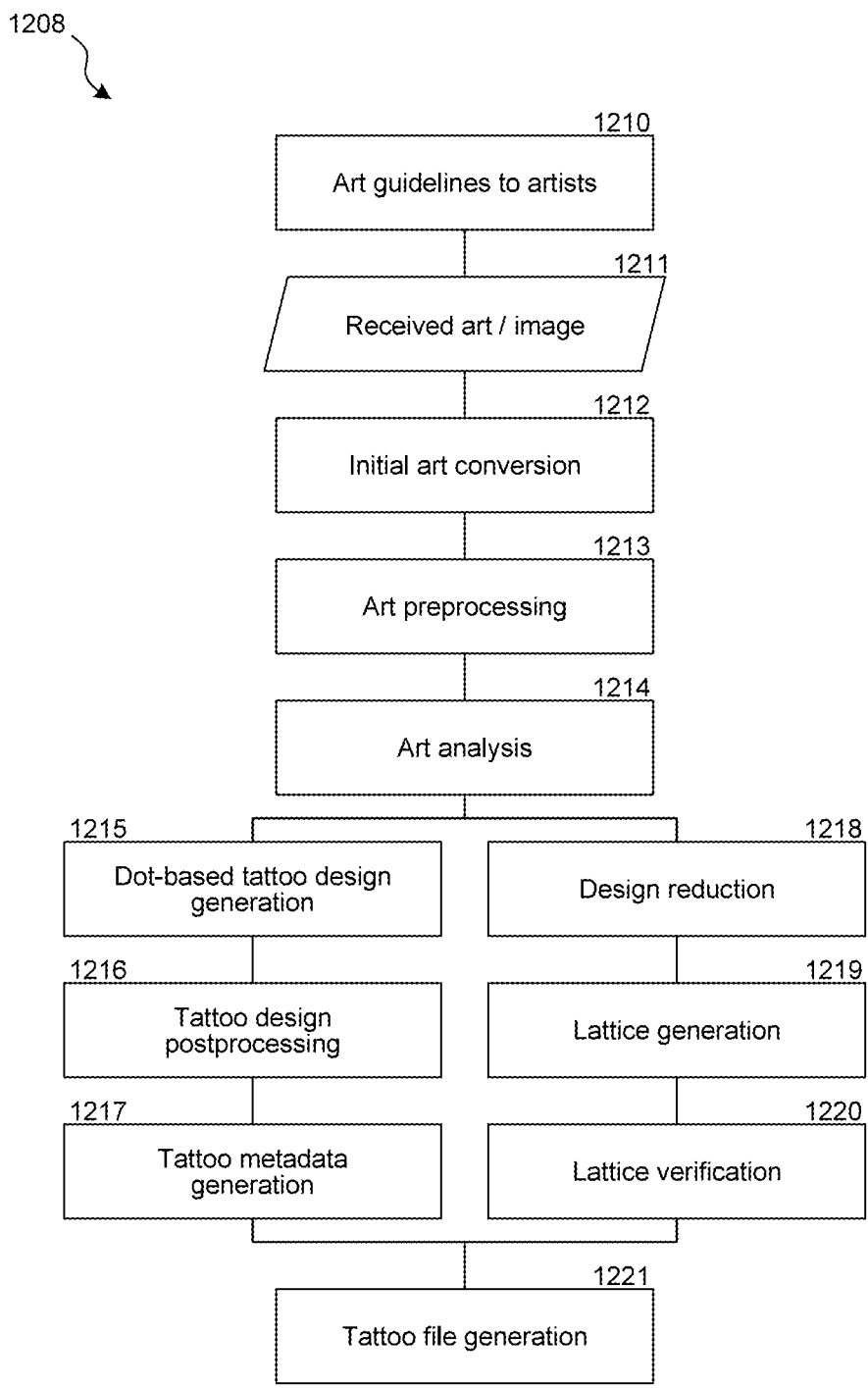
FIG. 19 is a block diagram of an embodiment of a digital tattoo file generation process optimized for automatic tattooing in accordance with an embodiment of the disclosure.

FIG. 19 is a flow chart of a method 1208 for generating tattoo digital files (or digital tattoos) that are optimized for automated tattooing and can be displayed as visual art or machine-read for the execution of the tattoo by the automated tattoo machine. These files are created by interpreting graphical artworks or images.

In step 1210, a set of optional guidelines and directions may be provided to the artist to facilitate the conversion of the artwork into a digital tattoo. In some implementations, this step may be omitted.

In step 1211, art is received either physically or by other means in digital media formats which may be vector-based, raster-based, or a combination of both. In some embodiments, the artwork is received via a wireless or wired connection. For example, the artwork can be received via a local area network or wide area network.

In step 1212, the artwork can be converted into a digital image with a standardized format. If artwork is received physically, it can be scanned at a desired resolution (e.g., a high resolution using a scanner, or other imaging device) suitable for being converted into a raster-based digital image. If artwork is received in digital media format, any vector-based components of the artwork may be rasterized at a certain high resolution. The technique for converting the artwork to a digital image can be selected based on the desired processing time, resolution, and/or conversion accuracy.

In step 1213, the digital image can be preprocessed. For example, the digital image can be preprocessed to adjust its brightness, contrast, light curves, dynamic range, color distribution, and/or enhance desired geometric features, such as edges. Separate preprocessing procedures may be applied to different parts of the image, and manual touch-ups could be performed to achieve desired aesthetic.

In step 1215, a dot-based tattoo design can be generated by, for example, using one or more conversion algorithms to convert the digital image into a collection of tattoo dots. This conversion may be performed in multiple stages, aimed to convert different aspects of the image, such as dots, lines and shades. The number of dots used to represent the tattoo design can be selected based on the resolution and capabilities of the tattoo apparatus.

In steps 1214 and 1215, different visual components of the artwork can be detected and analyzed, such as individual dots, lines, shaded areas and edges of shaded areas. The analysis may be performed in multiple stages and parts of the image may be masked off at each stage to avoid duplicate detection of features. Isolated dots on the image whose size are similar to the tattoo dot or needle size may be identified as individual tattoo dots and assigned a representative color or shade. Lines and edges of shaded or solid areas may be detected as lines with a representative color, shade and thickness, each of which may be varied. Line tracing techniques may be used to identify continuous lines or edges, and to construct a series of tattoo dots with varying spacing and dot size to represent the line with varying contrast, thickness or shade. The rest of the image, such as areas of varying color or shade, or continuous areas of a solid color may be covered with a collection of tattoo dots using space-filling methods, where the spatial density and/or size of dots is varied to represent the variations of color or shade on the image. Space-filling may be performed based on an underlying ordered grid, probabilistic dot placement, half-toning or dithering techniques. Computational stippling methods, such as one utilizing weighted Voronoi cells, may be used to spatially rearrange the locations of tattoo dots based on the gradients of color or shade on the image. This operation may improve the visual representation of image gradients by the spatial distribution of tattoo dots. The resulting collection of tattoo dots constitutes a candidate tattoo design, and it is rendered on a screen in step 1216 for visual inspection by a human operator.

In step 1216, the tattoo design can be postprocessed. The candidate tattoo design may be compared with the original artwork on the screen to facilitate the inspection. The tattoo design may also be digitally overlaid on pictures of body parts with different skin colors, to assess its aesthetic outcome. At this step, the operator may add, remove, and/or relocate dots manually to improve the aesthetic outcome of the tattoo design. Based on the outcome, the operator may also choose to modify the image preprocessing settings of step 1213, and repeat steps 1213-1216 to improve the design. As a result, the output of step 1216 can be the final tattoo design, which visually represents the original artwork received in step 1211.

In step 1217, metadata may be assigned to the tattoo dots to modify their puncture settings, such as the needle extension and number of punctures or ink delivery flowrate in the needle reservoir, around their nominal values, in order to achieve a particular aesthetic aspect. For example, to better represent a light-shaded area of the artwork, the number of punctures or needle extension may be decreased for the collection of tattoo dots in that area. Or, these settings could be increased for very dark or color-saturated areas, to increase the deposited ink per puncture and consequently reduce the time needed to tattoo such areas.

In step 1218, a simplified design outline is generated from the art, which may be placed on the stencil to allow the customer to review the design's positioning on the skin before starting the tattooing operation. A subset of the features detected in step 1214, such as the most distinct lines and edges, may be used to create the design outline. Positioning of the design may also be reviewed using augmented reality, wherein the final tattoo design (step 1216) is overlaid on a camera image or live video, based on the positioning and deformation of the applied stencil on the image detected by machine vision. If augmented reality is used, including the design outline on the stencil may not be necessary.

One or more of the steps 1218-1220 can be performed in parallel with steps 1215-1217. For example, the lattice generation 1219 can be performed concurrently with the step 1216. Each step can incorporate data from other steps. For example, the tattoo metadata generation at step 1217 can be based on the design reduction at step 1218. The order and timing of the steps can be selected based on the tattoo file to be generated.

In step 1219, a spatial arrangement of fiducial markers (lattice) is generated and placed on the stencil. The lattice of fiducial markers is employed by machine vision to track the deformation of the skin and detect its spatial coordinates (see FIGS. 5A-6B). This lattice is constituted of fiducial markers of a certain diameter (e.g. 50-500 um) and spacing (e.g. 100-1000 um). This lattice may be spatially arranged as a square grid, as shown in FIG. 5A, although other arrangements are possible, such as a hexagonal grid, or unordered spatial distributions. Information-encoding variations (pattern) of these fiducial markers such as location, size, omission, shape or color, (see FIG. 5A for a spatial variation encoding example) may be used to create a pattern which allows identification of the local spatial coordinates by the machine vision. The pattern may be probabilistically (randomly) or deterministically (rule-based) generated.

In step 1220 of FIG. 19, the local-uniqueness and robustness of the pattern is checked. The requirement of local-uniqueness means: different parts of the pattern, as exposed through the contactor window, must be distinct for every potential position of the contactor. The robustness of the pattern means that the local-uniqueness persists when parts of the pattern are concealed or when random noise is introduced to the pattern (these conditions may occur during tattooing operation or when the stencil is first applied to the skin). Deterministic or probabilistic modifications may be made to the pattern, manually or automatically, to improve the likelihood of either requirement being satisfied. Steps 1219-1220 can be repeated until a locally-unique and robust pattern is generated. In some embodiments, step 1219 and 1220 can be performed in advance and the same lattice may be reused for various stencils for tattoos of the same size.

In Step 1221, the digital tattoo data or file can be generated, which contains at least (i) the coordinates of the dots in the tattoo design (step 1216), and (ii) the coordinates of the fiducial markers (steps 1219, 1220), (iii) a digital image of the stencil which (a) at least contains the fiducial markers and (b) may also contain the design outline from step 1218. The tattoo file may also contain: (iii) a digital image of the original artwork (step 1212), (iv) artwork ownership and licensing information, (v) the settings used in image preprocessing (step 1213), (vi) the metadata for tattoo dots (step 1217), (vii) simplified outline of the art (step 1218) in vector form, (viii) a pre-computed data table to facilitate finding the tattoo dots in a particular region. Each component in the digital tattoo file may be stored using the appropriate data structures for that component, such as, a data table for the dot coordinates, a vector-based graphics format for the stencil, a raster-based graphics format for the artwork image, etc. As described in FIG. 3C the information in the tattoo file, such as the components (i, ii, vi, vii), and the machine vision analysis (FIGS. 5A-6B) are used in combination to create the machine instructions for each tattoo dot, controlling (i) spatial positioning of the needle on skin, (ii) needle extension, (iii) number of punctures, (iv) amount of ink injected on the needle.

The accuracy, repeatability, capability, and/or resolution of the robotic application of the tattoo, as compared to traditional manual tattooing, may be characterized, for example by one or more of the following. In one embodiment, the tattoo position (e.g., overall tattoo position, section of tattoo, etc.) relative to the absolute position on the skin may be ±0.5 mm, ±1 mm, ±2 mm, ±3 mm, or ±4 mm in a skin plane as compared to a stencil positioning. In other embodiments, the overall tattoo position relative to the absolute position on the skin may be ≤±5 mm, including but not limited to e.g. ±1 mm, ±2 mm, ±3 mm, ±4 mm, and all non-integer values e.g. ±0.6 mm, ±0.7 mm, ±1.2 mm, ±1.3 mm, etc. The relative tattoo position can be selected based on the size, intricacy, resolution, or other features of the stencil, tattoo, or the like.

The optical detection (e.g., machine vision accuracy) may be ~4 μm per pixel. In other embodiments, the optical detection or machine vision accuracy may be ≥~4 um per pixel, or ≤~4 um per pixel. In one embodiment, the extracted position error of a fiducial marker may be ≤±50 um in the skin plane, including but not limited to for example, ±40 μm, ±35 μm, ±30 μm, ±20 μm, and all other non-integer values e.g. ±25.7 μm, ±25.6 μm, ±25.5 μm, etc. The detection capabilities of the optical detection can be selected based on the characteristics of the tattoo and may be better than detection via the naked eye.

The accuracy of the needle in the z plane may be ≤±100 μm from the prescribed needle elongation setting due to skin deformation, including but not limited to for example, ±90 μm, ±85 μm, ±80 μm, ±70 μm, and all other non-integer values e.g. ±65.7 μm, ±65.6 μm, ±65.5 μm, etc. In one embodiment, the position accuracy of each tattoo dot compared to its neighbors may be ≤±50 um, including but not limited to for example, ±40 μm, ±35 μm, ±30 μm, ±20 μm, and all other non-integer values e.g. ±25.7 μm, ±25.6 μm, ±25.5 μm, etc.

The expected resolution of tattooing in dots per inch (dpi) may be 72 to 2540 dpi, but is variable based on design dot density. For example, the expected resolution of tattooing may be, but is not limited to being, between 72 to 2540 dpi, or larger than 72 to 2540 dpi, e.g. between 50-3000 dpi, etc.

In one embodiment, the expected dot size may be, but is not limited to, between 100 um to 5000 um based on the needle size. In one embodiment, the expected tattooing speed may be ≤0.15 s per dot, for example including but not limited to 0.1 s per dot, 0.8 s per dot, 0.5 s per dot, etc. In one embodiment, the expected time of completion of a 3.5×2 in, 15000 dots tattoo, including dry dots may be for example ≤40 min.

Figure 20:
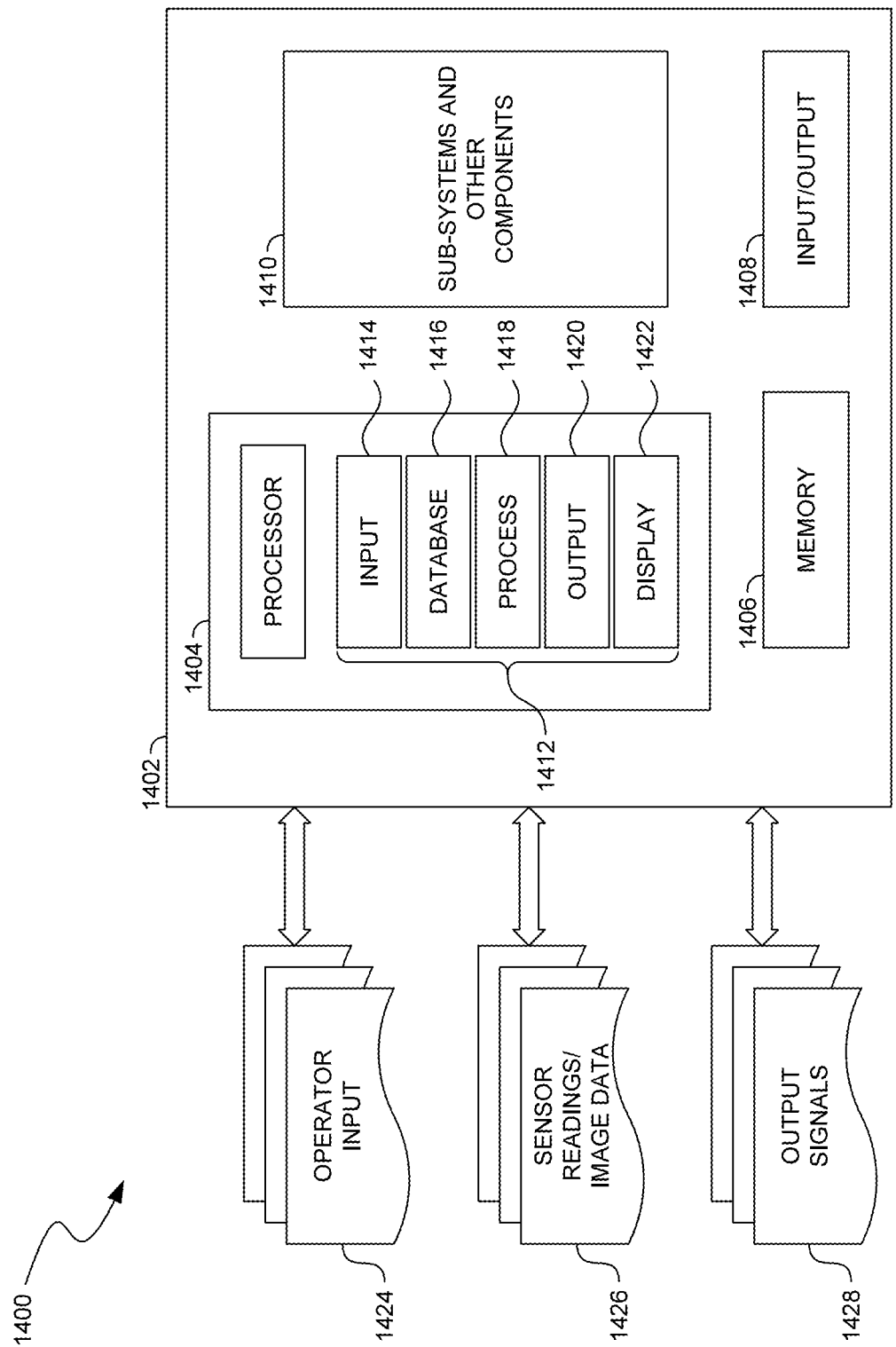
FIG. 20 is a schematic block diagram illustrating subcomponents of a controller in accordance with an embodiment of the disclosure.

FIG. 20 is a schematic block diagram illustrating subcomponents of a controller 1400 in accordance with an embodiment of the disclosure. The controller can be part of a control unit (e.g., controller 108 or 109 of FIG. 1B) and/or can be incorporated into other tattoo device or components disclosed herein. The controller 1400 can include a computing device 1402 having one or more of each of processors 1404, memory 1406, input/output devices 1408, and/or subsystems and other components 1410. The computing device 1402 can perform any of a wide variety of computing processing, storage, sensing, imaging, and/or other functions. Components of the computing device 1402 may be housed in a single unit or distributed over multiple, interconnected units (e.g., through a communications network). The components of the computing device 1402 can accordingly include local and/or remote memory storage devices and any of a wide variety of computer-readable media.

As illustrated in FIG. 20, the processor 1404 can include a plurality of functional modules 1412, such as software modules, for execution by the processor 1404. The various implementations of source code (i.e., in a conventional programming language) can be stored on a computer-readable storage medium or can be embodied on a transmission medium in a carrier wave. The modules 1412 of the processor can include an input module 1414, a database module 1416, a process module 1418, an output module 1420, and, optionally, a display module 1422.

In operation, the input module 1414 accepts an operator input 1424 via the one or more input devices, and communicates the accepted information or selections to other components for further processing. The operator input 1424 can include, for example, stencil information, tattoo design information, subject preferences (e.g., preferences for tattoo, length of session, tattoo resolution, tattoo style, etc.), or the like. The information can be displayed via the display 1422. The display 1422 can be a touchscreen or other output device capable of displaying and/or receiving input.

The database module 1416 organizes records, including internal and external variables, settings (e.g., machine settings, puncture settings, etc.), puncture parameters, scores (e.g., dot scores), subject data sets, experimental data, tattoo graphic data, stenciling data, artwork, tattoo designs, and operating records and other operator activities, and facilitates storing and retrieving of these records to and from a data storage device (e.g., memory 1406, an external database, etc.). Any type of database organization can be utilized, including a flat file system, hierarchical database, relational database, distributed database, etc.

In the illustrated example, the process module 1418 can generate control variables based on sensor readings and/or image data 1426 from sensors, machine vision systems, and/or other data sources. The sensors can include, without limitations, impedance sensors, accelerometers, gyroscopes, contact sensors, pressure sensors, sensors configured to output signals associated with needle depth or position, galvanic sensors, or other suitable sensors.

The output module 1420 can communicate operator input to external computing devices and control variables. The output module 1420 can include one or more communication elements, transmitters, receivers, antennas, ports (e.g., USB ports, LAN port(s), optical port(s), etc.), interfaces, etc. Example interfaces include USB port interfaces, a wired Local Area Network interface (e.g., Ethernet local area network (LAN) interface), a wireless network interface via a WiFi LAN access in accordance with, for example, I.E.E.E. 802.11b/g/n wireless or wireless network communications standard. The display module 1422 can be configured to convert and transmit processing parameters, sensor readings 1426, output signals 1428, via one or more connected display devices, such as a display screen, touchscreen, etc. the output signals 1428 can be sent to one or more components to control or command the components.

In various embodiments, the processor 1404 can be a standard central processing unit or a secure processor. Secure processors can be special-purpose processors (e.g., reduced instruction set processor) that can withstand sophisticated attacks that attempt to extract data or programming logic. The secure processors may not have debugging pins that enable an external debugger to monitor the secure processor's execution or registers. In other embodiments, the system may employ a secure field programmable gate array, a smartcard, or other secure devices.

The memory 1406 can be standard memory, secure memory, or a combination of both memory types. By employing a secure processor and/or secure memory, the system can ensure that data and instructions are both highly secure and sensitive operations such as decryption are shielded from observation. In various embodiments, the memory 1406 can be flash memory, secure serial EEPROM, secure field programmable gate array, or secure application-specific integrated circuit. The memory 1406 can store instructions performing any of the methods disclosed herein, including, without limitation processing images, obtain information about our work and or tattoo designs, acquiring information, analyzing target sites, dot scoring, data collection, determining puncture settings, digital stencil reference data, or the like. The memory 1406 can include non-transitory computer-readable medium, memory component, etc. carrying instructions, which when executed, causes actions. The actions can include steps disclosed herein.

The steps of the methods disclosed herein can employ one or more AI techniques. AI techniques can be used to develop computing systems capable of simulating aspects of human intelligence, e.g., learning, reasoning, planning, problem solving, decision making, etc. AI techniques can include, but are not limited to, case-based reasoning, rule-based systems, artificial neural networks, decision trees, support vector machines, regression analysis, Bayesian networks (e.g., naïve Bayes classifiers), genetic algorithms, cellular automata, fuzzy logic systems, multi-agent systems, swarm intelligence, data mining, machine learning (e.g., supervised learning, unsupervised learning, reinforcement learning), and hybrid systems.

In some embodiments, image processing, detection (feature detection, fiduciary marker detection, reference feature detection), skin puncture property acquisition and analysis, skin color identification, position analysis, dot scoring, art conversion, artwork preprocessing, artwork analysis, tattoo design generation, lattice generation, lattice verification, and other steps disclosed herein can use one or more trained machine learning models. Various types of machine learning models, algorithms, and techniques are suitable for use with the present technology. In some embodiments, the machine learning model is initially trained on a training data set, which is a set of examples used to fit the parameters (e.g., weights of connections between "neurons" in artificial neural networks) of the model. For example, the training data set can include any of the reference data stored in database 1416 (FIG. 20), such as a plurality of reference puncture data sets or a selected subset thereof.

In some embodiments, the machine learning model (e.g., a neural network or a naïve Bayes classifier) may be trained on the training data set using a supervised learning method (e.g., gradient descent or stochastic gradient descent). The training dataset can include pairs of generated "input vectors" with the associated corresponding "answer vector" (commonly denoted as the target). The current model is run with the training data set and produces a result, which is then compared with the target, for each input vector in the training data set. Based on the result of the comparison and the specific learning algorithm being used, the parameters of the model are adjusted. The model fitting can include both variable selection and parameter estimation. The fitted model can be used to predict the responses for the observations in a second data set called the validation data set. The validation data set can provide an unbiased evaluation of a model fit on the training data set while tuning the model parameters. Validation data sets can be used for regularization by early stopping, e.g., by stopping training when the error on the validation data set increases, as this may be a sign of overfitting to the training data set. In some embodiments, the error of the validation data set error can fluctuate during training, such that ad-hoc rules may be used to decide when overfitting has truly begun. Finally, a test data set can be used to provide an unbiased evaluation of a final model fit on the training data set.

To generate a tattoo plan or protocol, a data set can be input into the trained machine learning model(s). Additional data, such as the selected subset of reference patient data sets and/or similar patient data sets, and/or treatment data from the selected subset, can also be input into the trained machine learning model(s). The trained machine learning model(s) can then calculate whether various candidate treatment procedures and/or medical device designs are likely to produce a favorable outcome for the patient. Based on these calculations, the trained machine learning model(s) can select at least one treatment plan for the patient. In embodiments where multiple trained machine learning models are used, the models can be run sequentially or concurrently to compare outcomes and can be periodically updated using training data sets. The module 1420 can use one or more of the machine learning models based the model's predicted accuracy score.

The controller 1400 can include any processor, Programmable Logic Controller, Distributed Control System, secure processor, and the like. A secure processor can be implemented as an integrated circuit with access-controlled physical interfaces; tamper resistant containment; means of detecting and responding to physical tampering; secure storage; and shielded execution of computer-executable instructions. Some secure processors also provide cryptographic accelerator circuitry.

The input/output device 1408 can include, without limitation, a touchscreen, a keyboard, a mouse, a stylus, a push button, a switch, a potentiometer, a scanner, an audio component such as a microphone, or any other device suitable for accepting user input and can also include one or more video monitors, a medium reader, an audio device such as a speaker, any combination thereof, and any other device or devices suitable for providing user feedback. For example, if an applicator moves an undesirable amount during a tattoo session, the input/output device 1408 can alert the subject and/or operator via an audible alarm. The input/output device 1408 can be a touch screen that functions as both an input device and an output device.

The controller 1400 can detect events, such as adverse events. The adverse events can include interruptions during the tattoo execution, such as (1) temporarily pausing and resuming the tattooing process, 2) stopping and later reinitiating the tattooing process, and 3) stopping the tattooing process due to an emergency or critical event and later reinitiating the tattooing process. The operator can be notified via the input/output devices 1408 of a detected event. Sensor readings 1426 can be analyzed to automatically detect events based on sensor output. The tattooing system 90 of FIG. 1B, shuttle 104 of FIG. 2, tattooing apparatus 400 of FIG. 8, tattoo device 900 of FIG. 14, and tattooing system 908 of FIG. 15 can detect events and may perform recovery processes based on the detected event, as discussed below.

Example Tattooing Environment and Systems

Figure 21:
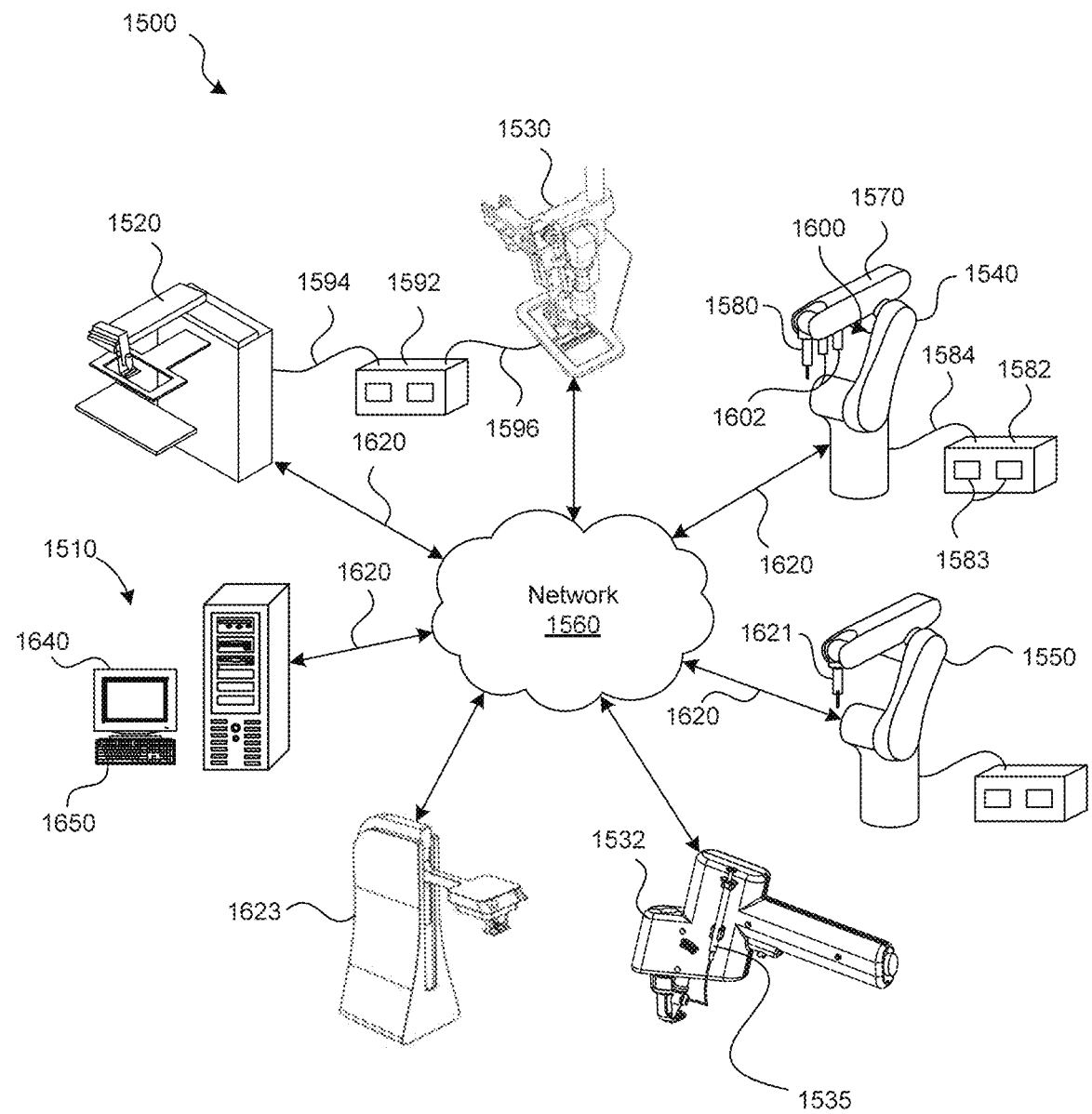
FIG. 21 is a network diagram of a tattooing environment and system in accordance with an embodiment of the disclosure.

FIG. 21 is a network diagram of a tattooing environment and system 1500 ("system 1500") in accordance with an embodiment of the disclosure. The description of the tattoo system 60 of FIG. 1A applies equally to the system 1500 unless indicated otherwise. The system 1500 includes a tattoo assistance system 1510 that can control tattoo apparatuses with different configurations and functionality to allow operator(s) to apply different types of tattoos to multiple clients. A network 1560 can provide communication between the various components of the system 1500 via one or more wireless connections, wired connections, optical connections, or the like. In one embodiment, some or all of the tattoo apparatuses are configured to be controlled by the tattoo assistance system 1510 and can be located at a single tattoo studio or separate tattoo studios.

FIG. 21 illustrates the system 1500 including a tattooing apparatus 1520 with features and functionality described in connection with FIGS. 1A, 1B, and 2, a tattoo apparatus 1530 with features and functionality described in connection with FIG. 8, a handheld tattoo apparatus 1532 with features and functionality described in connection with FIG. 14-16, and tattoo apparatuses 1540, 1550. The number, configuration, and functionality of the tattoo apparatuses and components can be selected based on the number of subjects to be tattooed at the same time, characteristics of the tattoos to be applied, desired length of tattoo session, preferences of the operator or subject, or the like. In some embodiments, different needle heads and/or needles can be utilized by the tattoo apparatuses 1520, 1530, 1532, 1540, 1550. Different types of end effectors, needle assemblies, tattoo needles, fluidic systems, controllers, or the like can be selected based on desired tattoo capabilities.

An ink delivery system can be used to provide ink to a single tattoo apparatus or to multiple tattoo apparatuses. Referring again to FIG. 21, the tattoo apparatus 1540 includes a robotic tattoo apparatus or multi-axis robotic arm 1570 (e.g., 3-axis robotic arm, 4-axis robotic arm, 5-axis robotic arm, 6-axis robotic arm, etc.), an end effector in the form of a needle head assembly 1580, and an ink delivery system 1582. The ink delivery system 1582 includes containers 1583 (e.g., ink bottles, ink cartridges, etc.), a fluidic system 1584 (including hoses, valves, pumps, etc.), and other fluidic components for fluidically coupling the ink delivery system 1582 and the needle head assembly 1580. The tattoo apparatus 1540 can include a machine vision device or system 1600 ("machine vision system 1600") with multiple image capture devices 1602 (e.g., spaced apart digital cameras) for imaging-based automatic inspection and analysis. In other embodiments, the devices 1602 are LiDAR sensors. The needle head assembly 1580 can also include one or more sensors for providing data to the tattoo assistance system 1510 via communication channel 1620.

The tattoo apparatus 1550 can include an end effector in the form of a needle head assembly 1621 with an integrated machine vision system, sensor(s) (e.g., contact sensors, optical sensors, mechanical sensors, chemical sensors, light detectors, galvanic sensors, pressure sensors, etc.), or other features disclosed herein. The integrated machine vision system can be protected by the housing of the needle head assembly 1621. The tattoo assistance system 1510 can concurrently support and provide functionality to different machine vision systems for each tattooing apparatus. This allows the tattoo studio to utilize various types of machine vision systems and apparatuses. The vision and/or sensor data can be used to control one or more tattoo steps.

An ink delivery system 1592 can be in fluid communication with the tattoo apparatuses 1520, 1530 and can include one or more pumps, lines, fittings, and other features (e.g. fluidic systems 1594, 1596) for independently delivering ink to the tattoo apparatuses 1520, 1530. In some embodiments, a single ink delivery system can deliver ink to all of robotic tattooing machines.

The handheld tattoo apparatus 1532 having ink delivery system 1535 including a fluid container or a cartridge (illustrated as a syringe compatible with a housing of the tattoo apparatus 1532), fluid line, and other fluidic components. Ink cartridges are discussed in connection with FIGS. 14 and 16. The handheld tattoo apparatus 1532 can be used to manually apply tattoos, touchup tattoos or dots applied robotically, and/or apply a portion of the tattoo while another portion of the tattoo is applied robotically. In some implementations, a single tattoo design can be applied by sequentially applying portions that tattoo using robotic tattoo apparatus (e.g., robotic tattoo apparatus 1520, 1530, 1570, or 1550) while the portions of the tattoo are applied concurrently or sequentially by the handheld apparatus 1532. The handheld tattoo apparatus 1532 (or tattoo apparatuses of FIG. 21) can include one or more output modules to communicate with and provide data to the tattooing environment and system 1510. The tattooing environment and system 1510 can adaptively control the tattoo apparatus applying the tattoo based on the received data from another tattoo apparatus. This allows for coordination between tattoo apparatus to produce a desired tattoo. In non-tattoo implementations, the robotic tattoo apparatus 1520, 1530, 1570, or 1550 and handheld apparatus 1532 can be used to perform aesthetic treatments.

The tattooing apparatus 1532 can include ink container 1535. For example, the ink container 1535 may include an ink delivery system described in connection with FIG. 16. The tattooing apparatus 1532 and other tattooing apparatuses disclosed herein can include a pump or refilling system for replenishing ink by, for example, replacing or refilling the ink container 1535. The tattooing apparatus 1532 can be refilled when the ink is at a low level or at a rate commensurate to the number of punctures performed. The tattooing apparatus 1532 can refill or replace multiple ink containers to avoid downtime.

With continued reference to FIG. 21, the tattoo assistance system 1510 can include one or more controllers, displays 1640, input devices 1650, etc. and can include features or functionality disclosed herein. In some embodiments, the tattooing environment and system 1500 has multiple tattoo assistance systems 1510 each incorporated into the tattooing apparatuses. The tattoo assistance system 1510 and controllers disclosed herein can be programmed to identify events, including low ink supplies, machine vision alerts, temporary pauses, stop events, emergency or critical events, adverse events, or the like. The tattoo assistance system 1510 and controllers disclosed herein and can also be programmed to monitor and provide information such as ink levels, tattoo apparatus data (e.g., status, maintenance history, operational history, settings, etc.), client data (e.g., preferences, profiles, payment, order histories, etc.), tattoo design data, or the like.

In operation, the tattoo assistance system 1510 can generate a tattoo protocol to apply a tattoo and can communicate with the tattoo apparatus to be used. The tattoo assistance system 1510 can store one or more control maps, command programs, instruction sets, and other data for controlling the tattoo apparatus to be used. For example, the control map for the tattoo apparatus 1540 can include angles for controlling each of the joints of the robotic arm. In 6-axis robotic arm embodiments, the control map can include angles for each of the 6 joints to position the needle device 1580. Additionally or alternatively, the control map can include target pose data for positioning an end effector a desired location. For example, the control map can include translation data, rotation data, or other data with reference to one or more reference frames. Based on a target location of the end effector to apply a dot, the tattoo assistance system 1510 can determine the translation and rotation data and commands for moving the end effector to the target location.

The tattoo assistance system 1510 can implement one or more programs for enforcement regarding authorization, authentication, and/or configuration of the tattoo apparatuses. In some embodiments, the technology disclosed herein can be incorporated into a commercially available robotic system. The tattoo assistance system 1510 can communicate with the robotic system and obtain control data for controlling the robotic system. The control data can include, without limitation, number of degrees of freedom, geometric parameters of components of the robotic apparatus, force settings, range of motion data, pose data, tolerance data, or the like. The tattoo assistance system 1510 can generate one or more machine settings (e.g., settings for selected poses), control maps, command programs, instruction sets, kinematic model data, and other data (e.g., position matrices, Jacobian matrices, transformation matrixes, joint vectors, rotational vectors, translational vectors, etc.) based on the received control data.

In non-tattoo setting, the robotic tattoo apparatus 1520, 1530, 1570, or 1550 and handheld apparatus 1532 can a apply botulinum toxin, anti-wrinkle agents, denervating agents, anti-acne agents, collagen, medicants, or the like. The system can optically analyze a site and identify wrinkles (using a trained computer vision system similar to that described above). Targeted wrinkles located along the subject face (e.g., along the forehead, surrounding the eyes, etc.) or any other location. The apparatus can determine one or more puncture sites based on characteristics (e.g., size, depth, location, etc.) of the wrinkles. The apparatus can inject one or more anti-wrinkle agents at puncture sites to reduce or limit the appearance of the targeted wrinkles. The system can perform both medical and aesthetic procedures. In another implementations, each robotic tattoo apparatus 1520, 1530, 1570, or 1550 and handheld apparatus 1532 can apply ink, dyes, or other substances to articles, such as purses, belts, and other articles of manufacture disclosed herein.

Figure 22:
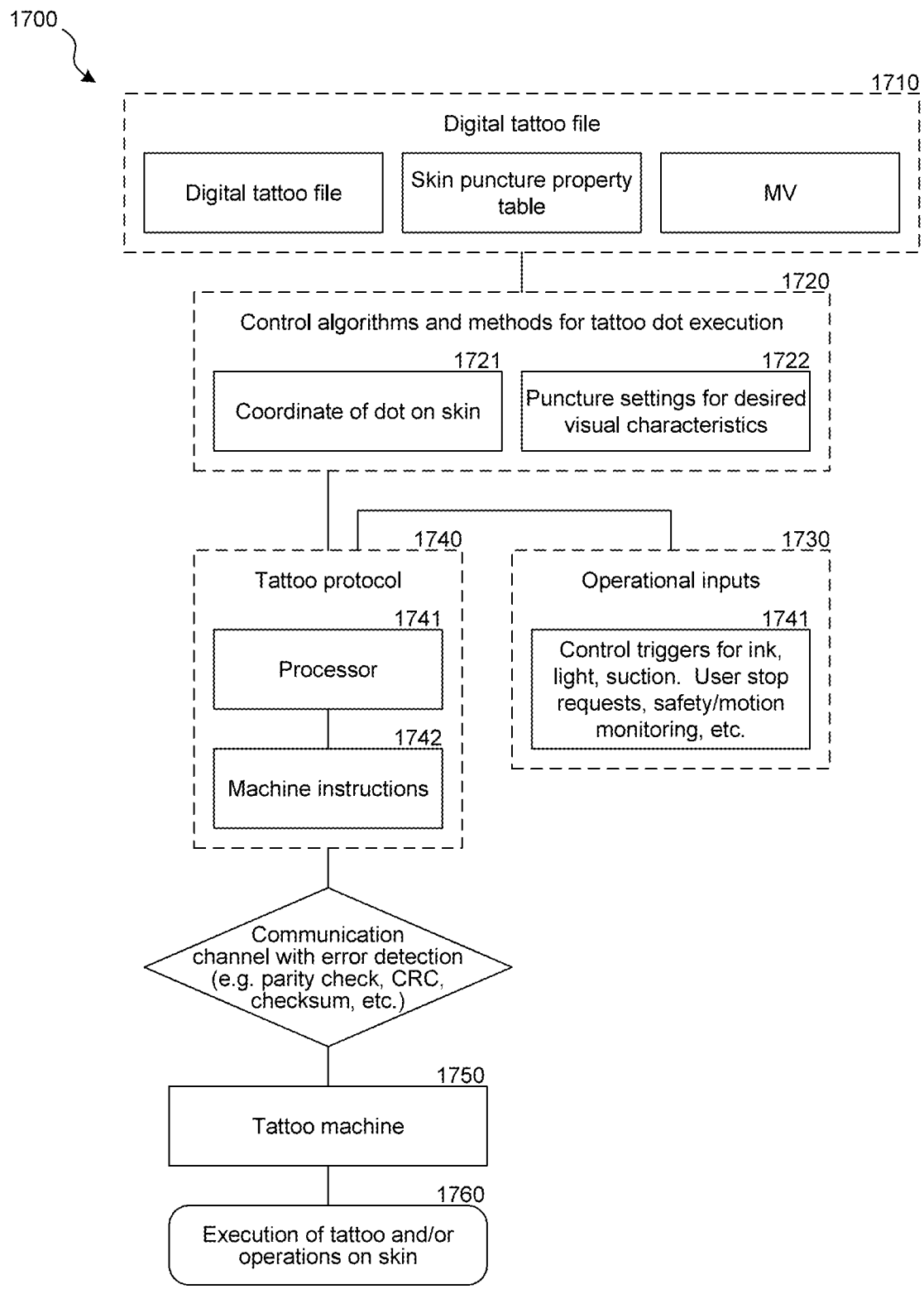
FIG. 22 is a block diagram of an embodiment of a tattooing protocol in accordance with an embodiment of the disclosure.

FIG. 22 is a block diagram of an embodiment of a tattooing method 1700 in accordance with an embodiment of the disclosure. In general, the tattooing method 1700 can be used to robotically apply a tattoo based on visual artwork. The tattooing protocol may (i) use a set of internal and external data as inputs 1710 related to tattoo execution, (ii) use a set of algorithms or methods 1720 which control tattoo execution based on these inputs, and/or (iii) generate machine instructions 1742 which upon execution by an embodiment of the tattoo system or machine 1750. At block 1760, a tattoo visually replicating the original artwork or design is applied. Details of the method 1700 are detailed below.

The inputs 1710 may include, for example, the digital tattoo file (e.g., output of method 1208 in FIG. 19), skin puncture property table (e.g., table 316 of FIG. 3C), and/or other skin puncture data collected by sensors, or data or output of machine vision-based methods (e.g., process 357 of FIG. 7). In some embodiments, all of the inputs are used to determine an execution control program. In other embodiments, the method can include selecting subsets of input or data. The skin puncture property table can include puncture property data for a relatively large area. Systems disclosed herein can identify and select a subset of the puncture property data corresponding to the site to which the tattoo will be applied. The selected subset of data can then be used to generate execution control data.

The control algorithms 1720 may include, for example, (i) methods and systems used to calculate the coordinates of tattoo dots on the skin 1721, such as those described in connection with FIGS. 5A,5B,6,7, and/or (ii) methods to identify or modify puncture settings 1722 (e.g., needle extension, number of punctures, etc.) to achieve desired visual characteristics for each tattoo dot, such as methods described in relation to FIGS. 12A,12B, and 13. The tattoo protocol may be executed by a controller, computer, or processor 1741, which uses the control algorithms 1720 as well as other operational inputs 1730 to generate machine instructions 1742 to perform tattooing. Example to operational inputs 1730 include: inputs to control the rate of ink injection, control lighting for the machine vision system, triggers to capture camera images, turn suction system on or off, any requests to stop or interrupt the operation from the user or from safety sensors (e.g., motion sensors, vibration sensors, accelerometers, contact sensors, gyroscopes, etc.), etc. The generated machine instructions 1742 are then transmitted to the tattoo system or machine 1750.

The instructions, upon execution by the tattoo machine 1750, causes the actuation of the components to perform the operations on the skin to apply the tattoo by, for example, moving the tattoo head and/or needle, applying tattoo dots, injecting of ink, cleaning the skin, flattening or moving the skin, interrupting operation, recovering from error events, etc. Error detection and error correction techniques may be used in the transmission of machine instructions, such as repetition codes, parity bits, checksum, cyclic redundancy check (CRC), Hamming codes, etc., to ensure the correct and intended instructions are executed on the skin.

Figure 23A:
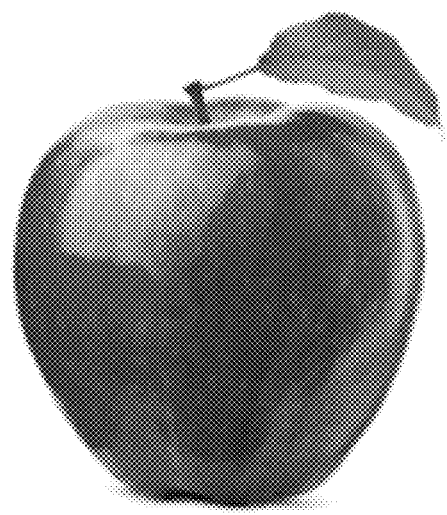
FIG. 23A shows an example of a visual art received from an artist.
Figure 23B:
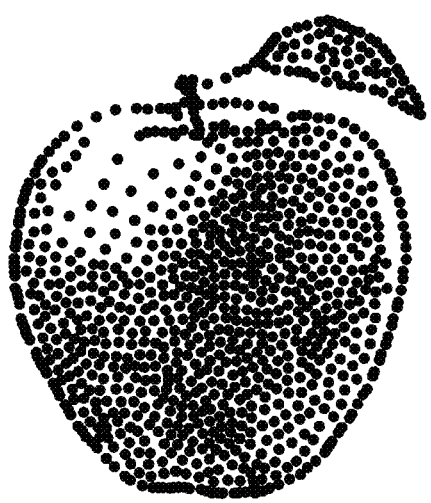
FIG. 23B shows a digital tattoo image or file generated based on the visual art of FIG. 23A.

FIG. 23A shows an example of a visual art received from an artist. As described in FIG. 19, a digital tattoo image or file can be generated based on the original artwork which contains at least a collection of tattoo dots to be placed on or formed in the skin, in addition to the other information for robotically executing the tattoo. An example of a generated collection of tattoo dots is shown in FIG. 23B, which may result from processing the artwork in FIG. 23A. The dots in the tattoo file may have uniform or varying dot-to-dot spacing, dot size, color, and/or ink saturation, in order to create an accurate visual representation of the original artwork. Referring to step 326 in FIG. 3C, in order to tattoo each dot in the window, machine actuation settings are determined, which includes of at least (i) the target coordinates of the dot on the skin within the window (see coordinates in FIG. 6B, calculated by method 357 of FIG. 7) and/or (ii) the puncture settings to achieve the desired dot characteristics (e.g., needle extension and number of punctures, read from the dot parameter table 316 of FIG. 3C, or based on the method 808 in FIG. 13). The machine actuation settings for the dot can be encoded as machine instructions to actuate the machine, for example: T, DOT, x, y, z, n may encode a machine task (T) to perform n number of punctures for a dot (DOT) at window coordinates x,y with a base needle extension z. The machine instructions may be encoded into a series of bytes or bits, appended with an appropriate error detection code, and then transmitted to the machine via a secure wireless channel, serial or parallel data cable, etc.

The machine can decode the received machine instructions, and performs an error check based on the method used. If no error is detected, the machine executes the actuation of the gantries and the needle as prescribed to apply the tattoo dot. If a communication error (for example a bit flip, bit omission or interference in the transmitted instruction) is detected, an error message is sent back to the processor to interrupt the operation or re-transmit the machine instructions. In addition to actuating the needle as explained above, other operational commands in the form of machine instructions may be transmitted to the machine, for example, instructions to (i) move the gantries (e.g., gantry 105, gantry 107, etc.), or the robotic arm, which houses the tattoo head, (ii) capture images from the machine vision camera (e.g., machine vision camera 131, 430, etc.), (iii) actuate the ink pump (e.g., pump of fluidic system 1584), and/or (iv) turn the suction system 150 on/off, etc. The executable instructions can be executed to coordinate operation between components of the systems and apparatuses disclosed herein.

The robotic tattooing systems can automatically form tattoo dots at levels of consistency, accuracy, and/or speed which cannot be achieved by human tattoo artists. Visual outcome of tattoo dots may be quantified by one or more of the following: (i) dot location, (ii) dot size, (iii) color intensity, (iv) total ink content of the dot, and/or (v) dot 2D and/or 3D geometry (e.g. including 2D imaged geometry and depth information). Needle actuation may be controlled by the puncture settings, including (i) number of punctures and/or (ii) needle extension. The needle actuation can be along a line of action that is generally perpendicular to the surface of the skin or at another desired orientation.

Figure 24A:
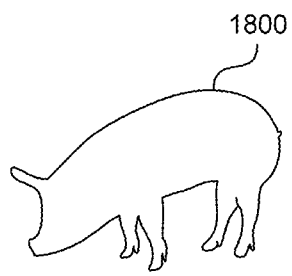
FIG. 24A shows a reference tattoo design in a target configuration when skin is relaxed.
Figure 24B:
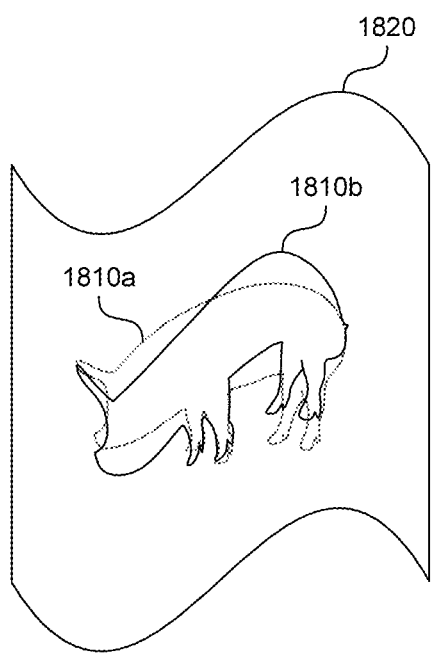
FIG. 24B shows the applied compensated and uncompensated designs when skin is deformed.
Figure 24C:
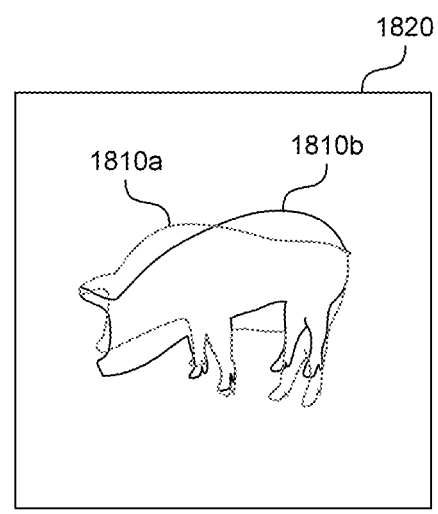
FIG. 24C shows the resulting tattoo designs of FIG. 24B on relaxed skin.

FIGS. 24A-24C illustrate an example of the effect of compensation of the deformation of a portion of the skin when tattooing. The tattooing system can compensate for changes of the skin to produce a desired tattoo design. The changes can be deformation of the skin caused by, for example, repositioning of the subject's body part, shear forces applied to the skin, pressure applied to the skin, etc. The system can identify the skin changes and select one or more algorithms to compensate for the identified changes. The deformation of the skin can be analyzed by comparing the position of fiducials taken in an undeformed, relaxed state to the current position of the fiducials.

FIG. 24A shows the reference tattoo design 1800 in a target configuration when skin is relaxed. The system can apply a tattoo that matches the reference tattoo design 1800 by modifying the tattooing protocol based on changes in position, deformation, and/or state of the body part. This allows tattooing to proceed when the body part moves, skin is stretched, or other unforeseen events occur. The tattooing systems disclosed herein can continuously or periodically monitor the skin and/or components of tattoo systems to modify the tattooing in real time. Compensation routines can be performed during a single tattoo session or between tattooing sessions and are discussed in connection with FIGS. 5A, 5B, 6A, 6B, and 7. Example outcomes of tattoo operations with and without skin deformation compensation are discussed in connection with FIGS. 24B and 24C.

FIG. 24B shows the stretched edge of the portion of the skin 1820 in a deformed state, whereas FIG. 24C shows the same area of skin 1820 in an undeformed or natural, at rest, state. The subject's body part may be deformed due to, for example, positioning the body part on a support surface, such as a tattooing pad. This may cause the tissue of the body part to be in a deformed or unnatural state. If skin deformation is not compensated for, the machine vision may track the position of the skin in the state in which the tattoo is performed.

FIG. 24B shows the compensated tattoo design 1810b on the deformed skin 1820 and an uncompensated tattoo design 1810a, which matches the reference design 1800 of FIG. 24A. The uncompensated tattoo design 1810a is applied without deformation compensation on the deformed skin 1820 and is an accurate rendition of the reference tattoo design 1800 of FIG. 24A. However, when the skin is returned in its undeformed state, shown in FIG. 24C, the uncompensated tattoo design 1810a is completely deformed and not an accurate representation of the reference design 1800 in FIG. 24A. The compensated design 1810b is applied to the skin as shown in FIG. 24B. The design 1810b appears deformed compared to the reference design of FIG. 24A. However, when the skin is returned to its relaxed, natural or undeformed state, in FIG. 24C, the design of the tattoo 1810b appears as an accurate rendition of the reference design of FIG. 24A. The systems and controllers disclosed herein can alter designs to match the deformation of skin such that the design has the desired configuration when the skin is relaxed or undeformed.

Figure 25:
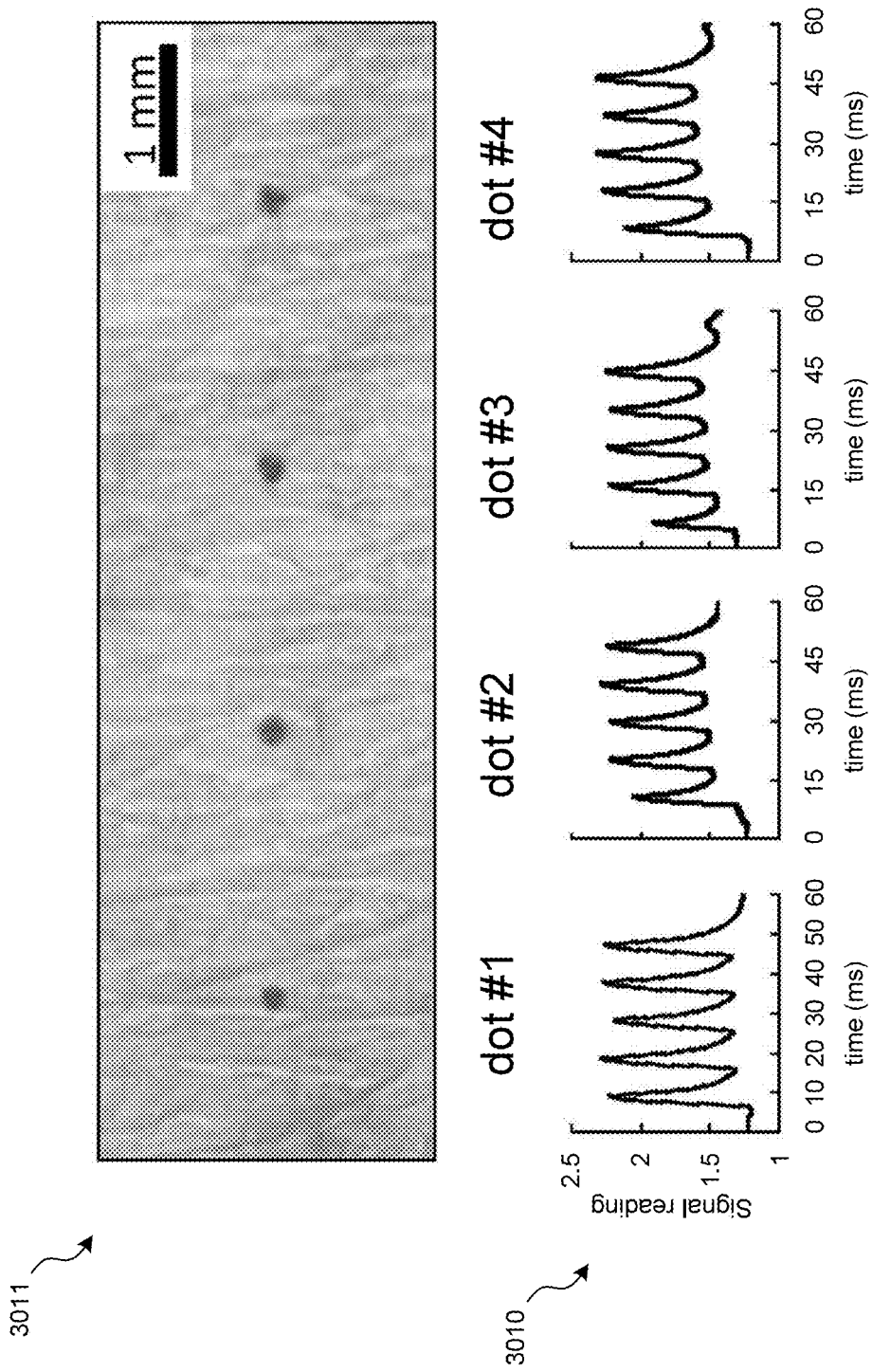
FIG. 25 shows a series of four tattoo dots robotically applied to human skin and sensor data collected when the tattoo dots were applied.

FIG. 25 shows a high-magnification photograph 3011 of a series of four tattoo dots robotically applied to human skin. In order to test consistency of the resulting tattoo dots, the same puncture settings were used for applying each dot. Bottom panel 3010 in FIG. 25 shows data collected from a galvanic sensor during the execution of each tattoo dot. The robotic system performed five punctures for each dot in less than 60 ms at a generally uniform rate of needle oscillation, detailed below.

The puncture settings included five punctures per dot and a needle extension of 350 μm beyond the exposed skin surface. Each rise in the signal readings corresponds to the needle coming into contact with the skin. The number of times the signal rises for each dot is equal to the number of punctures (5) prescribed to the machine, demonstrating the accuracy of the system in executing punctures. For example, dot #1 was formed by puncturing a location 5 times with the same needle. The tip of the needle was moved to a maximum depth 350 μm. As shown, the tattooing system was capable of consistently producing dots with a target size, for example, dot sizes with a ±10% deviation (±22 μm deviation) around a dot size of 225 μm. The dots are generally circular with well-defined peripheries. The puncture events were performed in less than 60 ms at a generally uniform rate of oscillation. The needle oscillation rate can be varied to, for example, compensate for changes at the puncture site, adjust for volumes of ink delivered for each puncture event, etc. The number of punctures for each location, needle extension (e.g., extension from a defined location), volume of ink delivery per puncture event, or other puncture settings can be selected based on the dots to be formed.

The tattooing system can achieve a positional accuracy with a target positional range. For example, the tattoo system applied the illustrated dots with a positional accuracy of 10-50 µm in the placement of tattoo dots on skin. To blend adjacent dots, for example, the positional accuracy could be increased. The positional accuracy can be increased to produce high-resolution micro tattoos. The positional accuracy can be selected based on the design of the tattoo. The puncture settings of the tattooing system can be inputted and/or modified by the user. In some embodiments, puncture settings are generated by the tattooing system. A combination of puncture settings from the user and generated puncture settings can be used. A user can review and modify the settings to customize the tattooing protocol based on user expertise. In other embodiments, the tattooing system generates a set of puncture settings that can be modified by a user after a checker confirms that the modifications conform to one or more criteria (e.g., tattoo quality criteria, safety criteria, pain management criteria, etc.). The puncture settings can be optimized puncture parameters determined by the tattooing system. The tattooing systems disclosed herein can be programmed to reduce or limit errors, such as location errors. The system can identify and correct for (i) error in robotic or gantry-based actuation (~0-10 µm) and (ii) measurement noise in machine vision system (~0-50 µm) which compensates for in-plane deformation of the skin. This allows dots to be accurately positioned throughout a portion of or an entire tattoo procedure. In comparison, positional accuracy of a human hand holding a tool tip may be on the order of 100-250 µm due to natural tremor, wander and jerk motions, according to experiments published in https://www.ncbi.nlm.nih.gov/pmc/articles/PMC359596/.

Figure 26:
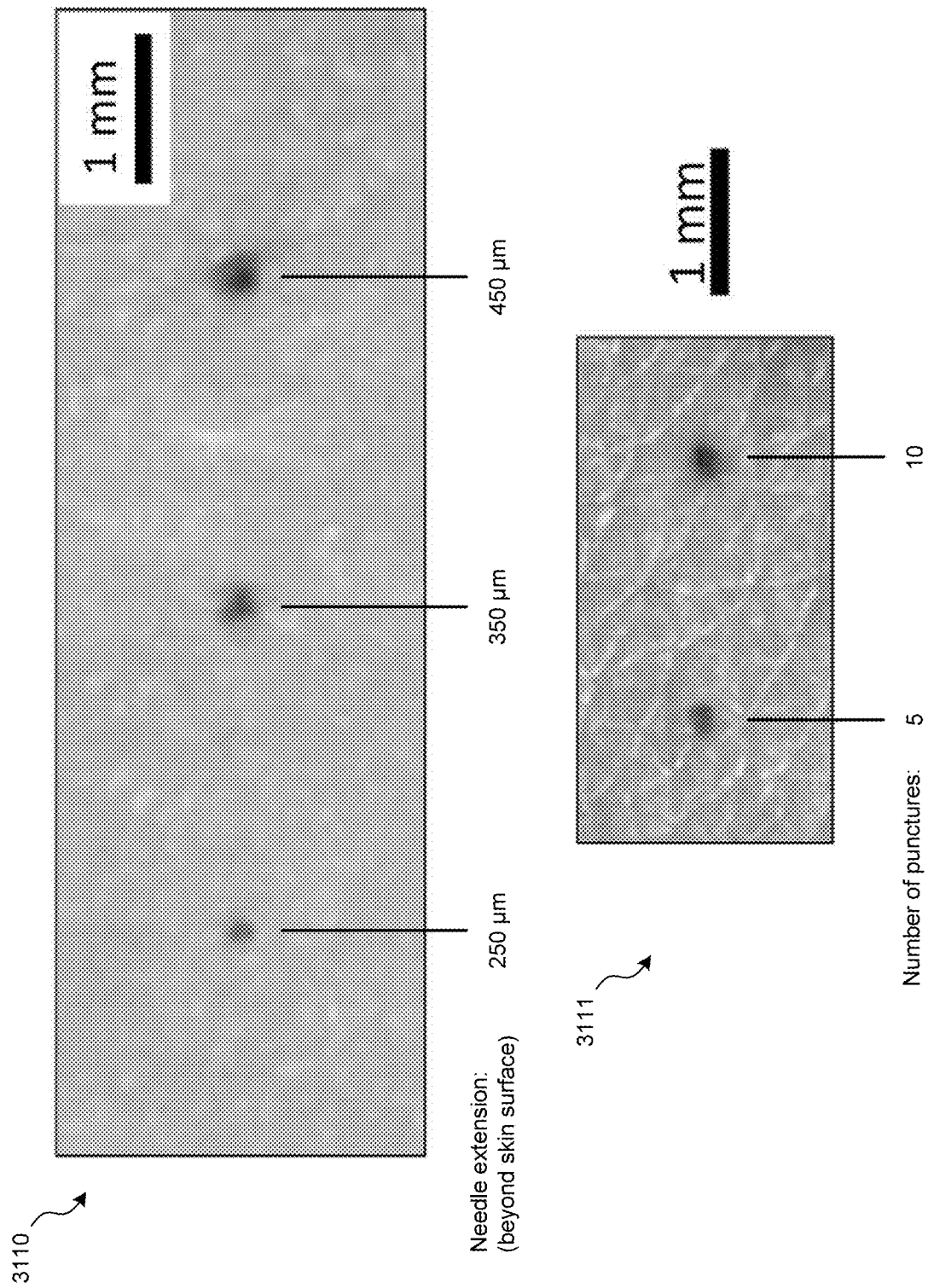
FIG. 26 shows a series of tattoo dots produced with varying puncture settings to control the visual outcome of tattoo dots.

FIG. 26 shows a series of tattoo dots produced with varying puncture settings to control the visual outcome of tattoo dots. The top image 3110 shows the effect of varying the needle extension setting (left to right, extensions of 250 µm, 350 µm, 450 µm beyond the skin surface). This shows how the needle extension influences the resulting dot characteristics (e.g., shape, size, etc.). The bottom image 3111 shows tattoo dots applied with 5 and 10 punctures per dot, at the same needle extension setting of 350 µm beyond the upper skin surface. The number of punctures influences the resulting characteristics of the dots. The resulting dot size, color intensity and total ink content are calculated based on image analysis techniques. The experiments show that all three visual properties can be efficiently controlled by the puncture settings.

Tattoo dots can form the building blocks of a tattoo design. The tattoo dots may not fall on a rectangular grid, which allows optimized spatial resolution. High resolution tattoos can be created by tattooing systems, remote servers, etc. For example, resolutions as high as 5 dots per millimeter may be achieved, based on a mean tattoo dot size of 200 µm. A tattoo with dimensions 10 cm by 5 cm may contain approximately 125,000 tattoo dots, where the visual appearance of each dot may be controlled by varying the puncture settings as shown in FIGS. 25 and 26. In some embodiments, the dot pitch can be 5 µm, 10 µm, 25 µm, 50 µm, 100 µm, 250 µm, 500 µm, 1 mm, 2 mm, or another pitch and the mean dot size can be 100 µm, 200 µm, 300 µm, 400 µm, 500 µm or another mean dot sizes.

Cleaning Operations

Systems disclosed herein can perform one or more cleaning operations before, during, and/or after tattooing. Before tattooing, cleaning can sanitize the tattooing site. During tattooing, cleaning can remove excess fluids, such as ink, bodily fluids, lubricant, etc. Cleaning allows for a clear observation of the skin by machine vision systems. The lubricant can have multiple roles. First, it acts as a lubricant for the contactor and needle to provide the proper interaction (e.g., sliding along the skin, gliding against the skin, etc.) with the skin. Needle lubrication can facilitate puncture, and contactor lubrication can inhibit excessive friction between the skin and the contactor. Second, the lubricant can act as a stain barrier. For example, when ink is applied on skin, the ink may stain the skin if no lubricant is applied to create a barrier. Without lubricant, the cleaning action is difficult and ink stain may remain after the removal of the excess ink. Through application of a lubricant, such as a hydrophobic silicone-based compound, a barrier is created over the skin. The ink drop may not cross the lubricant barrier, thereby preventing staining of the skin. The excess ink may be removed without resulting in staining or mitigating staining of the skin.

The contactor can also facilitate cleaning. The contactor can be firmly in contact with the skin during tattooing such that any excess fluids are kept within the contactor window. If no contactor is used, the ink and other fluid may runoff the tattoo area, stain other portions of the skin and potentially carry pathogen outside the tattoo area. The contactor can help reduce the extent of the cleaning as well as protecting against contamination. Suction systems can be used to remove excess fluid. The suction head may be integrated to the contactor window edge for edge suction and/or the suction may include a nozzle that runs across the tattoo window in the vicinity of the needle cartridge. The shape of the nozzle can be selected to provide suction in all conditions. For example, a badly positioned nozzle may be too far from the skin to remove small drops of excessive liquids. In another example, the nozzle may be positioned too close to the skin and may seal against the skin, removing the protective lubricant protective layer. The nozzle distance and angle of attack are selected to remove all excess liquid without removing a layer of lubricant and without sealing against the skin. A nozzle angle of attack may be inclined (e.g., a longitudinal axis of the nozzle may be inclined from the normal to the skin) such that the nozzle does not form a seal (e.g., an airtight seal, fluid-tight seal, etc.) with the skin, allowing the nozzle to be as close to the skin as desired. The excess fluid suctioned off the skin by the suction system may be collected in a collection container and discarded. The suction line may also be disposable or sterilizable.

Some amount of skin staining may be acceptable if the observation by the machine vision system can be performed effectively as described herein. The cleaning action may be repeated if the machine vision system cannot perform its tasks effectively. For example, residual ink may occult the field of view of the machine vision. The machine vision step used in position may be unable to perform the position and deformation analysis and may trigger additional cleaning. The additional cleaning may remove the occlusion due to excess fluid.

Movement and Position Detection

The tattooing systems disclosed herein can be operated based, at least in part, on detection of movement, positional information, needle detection, or the like. The tattooing process may be paused in response to detecting movement of the skin being tattooed. This movement may be detected by a single sensor or multiple sensor embodiment. Machine vision can be used to visualize the skin and may be used to detect changes in skin position. If the skin changes position, the visible set or pattern of fiducials (e.g. pattern 342*b* in FIG. 6A) may be altered and detected using machine vision. A global approach may also be used by comparing consecutive images during the tattoo process. If a change occurs, the two consecutive images may be different which may result in rapid detection of any potential movement. The image variation may then be evaluated to determine whether a movement actually occurred. For example, some pixel color and density value from one picture may be compared to the color and density value of a consecutive picture. This can be done very rapidly compared to the speed of tattooing. If the difference is large enough, the full evaluation of the portion of the skin position by pattern analysis (for example method 357 of FIG. 7), which is a slower process compared to tattooing, can be performed. The rapid analysis process may be hindered by the appearance of excess fluid and camera movement, resulting in a slower confirmation process.

Other sensor(s) may be used to simplify the process. For example, a secondary optical sensor may be integrated to the contactor to observe changes from image to image of a portion of the skin that is not being tattooed. The detection by the optical sensor may be used to trigger a full observation of the position of the portion of the skin being tattooed by the machine vision system. In some embodiments, the optical sensor includes a light source (e.g., a light-emitting diode (LED)) and one or more light detectors (e.g., an array of photodiodes). The light detector(s) can output images or other data for determining movement of the skin.

Non-optical sensors and systems may be used. The non-optical sensors can include one or more accelerometers, gyroscopes, vibration sensors, etc., that may be used to detect skin movement. For example, when the skin moves, this movement may be picked up as a vibration which triggers a pause and an evaluation of the position of the skin. Additionally or alternatively, the dielectric property of the skin may be used to evaluate movement. In the case of movement, the electrical path between the needle electrode and the measurement electrode is changed, resulting in a variation in impedance. This variation may be used to detect movement of the portion of the skin being tattooed. The coordinate of the tattoo dot would likewise be updated to account for the change of position of the portion of the skin being tattooed. A controller (e.g., controller 1400 of FIG. 20) can be programmed to compensate for the change of skin position.

Tattooing Processes and Events

A temporary pause may be initiated during the tattoo process by either the operator, the client or the machine itself. In case of a client or operator interruption, a command or tactile switch may be available. In the case of a machine triggered interruption, a warning message may be displayed (e.g., via the input/output 1408 or display 1422 of FIG. 20) to inform the operator that a pause was triggered as well as an error or warning message. In normal operation triggering, the aforementioned temporary pause may cause the tattoo machine to pause the tattooing process. Setting granularity can include, but is not limited to, pausing between dots or between the executions of all the dots within a tattoo window. When the tattoo process is ready to resume the tattoo operator or client may resume the tattooing process without a requirement for recalibration or reinitiating of the tattoo machine. The operator may instead decide to trigger a stop if the tattoo process cannot be resumed or at the request of the client.

A stop of the tattoo process may be triggered by the operator, using either a switch or a command line. The tattoo progress information is dumped from the core to a restart file to assist with the eventual resuming of the tattooing process, and the actuators are put in a safe position which would allow the client to disengage from the machine safely. In the case, alignment may be disrupted and a recalibration of the tattoo machine may be required. To resume tattooing after a stop, the client can reengage with the machine and the tattoo area can be centered in the tattoo frame. Recalibration is achieved by initially performing a scan (e.g., a partial or comprehensive scan) of the tattoo area before moving in the vicinity of the last completed dot area and recommencing the tattooing process. If the tattoo stencil is not sufficiently preserved for the performance of machine vision, a new stencil may be applied and machine vision can assess the location of the next tattoo dot by scanning the completed portion of the tattoo. Because it may be difficult for an operator to exactly align a stencil with a partially completed tattoo, the new applied stencil lattice is free floating. This means that the position of the reference tattoo design is not initially fixed within the lattice. The machine vision can be used to scan the tattoo area completely, in particular the already completed area of the tattoo. This allows using a digital image correlation or other image analysis method to identify the exact position of the partially completed tattoo in the newly applied lattice. The position of the reference design within the digital reference lattice is then calculated from this digital image correlation and the tattoo process can be resumed where the partial tattoo was initially stopped. The same or similar strategy may be used when the expected tattoo is larger than the tattoo frame, in which case the stop function is triggered to position the client's skin such that the non-tattooed part of the tattoo is now centered in the tattoo frame while still some of the completed partial tattoo is also visible to provide sufficient machine vision information for position referencing. This stop and shift strategy is repeated until the tattoo is fully completed.

The systems can provide optimal tattoo frame placements for a tattoo design. The frame placements can be displayed (e.g., inserted, overlaid, etc.) on a reference image of the body part with stenciling, a reference stenciling image (e.g., an image of the applied stenciling), etc. For example, a display (e.g., display of controller 108 of FIG. 1B, display 1640 of FIG. 21, display 1422 of FIG. 20, etc.) can display the frame placements with respect to the reference image.

In some embodiments, systems provide positioning features for locating the non-tattooed skin with respect to the tattoo frame or another component. In some embodiments, the system includes one or more projection lighting devices (e.g., LED lighting devices, laser devices, etc.) configured to project one or more images (e.g., arrows, tattoo boundary markers, targets for centering in a window of the tattoo frame, etc.) on the skin or frame. After the skin is positioned with respect to the frame, the system can analyze and confirm proper placement. If adjustments are needed, additional positioning information can be provided to the user.

In some embodiments, stenciling can include positioning information for sequentially positioning the body part with respect to the tattoo frame. For example, the positioning information can be used to align the body part with one or more features of the frame by, for example, centering a non-tattooed part of the body part. The system can analyze completed portions of the tattoo and can, if needed, instruct the user to move the body part to enable tattooing to be resumed based on the fiducial and/or applied dots. The positioning information can be reference frames, sizing features, targets, locators surrounding fiducials, etc. In some embodiments, the system generates positioning features based on analysis of fiducials, applied portions of tattoos, and/or other reference features. Additionally or alternatively, one or more positioning features can be integrated into the tattoo frame and be activatable direction indicators, such as light sources (e.g., arrow-shaped light sources).

When generating a tattooing protocol for large tattoos, the systems disclosed herein can generate a positioning protocol to be provided to a user. To avoid long periods of uncomfortable tattooing, the system can determine sequences of tattooing for pain management. For example, tattoo sections can be assigned a pain score and a protocol can be generated based on one or more criteria, such as maximum length of substantially continuous tattooing with a threshold pain score, anticipated pain based on tattooing area (e.g., sensitive areas have a high pain or discomfort score, etc.).

In the event of an emergency or critical event (as determined by the client and/or the tattoo operator), a command or tactile emergency switch may be available for that purpose. In normal operation, triggering the emergency switch will cut power to the actuators (directly and indirectly) and dumps the tattoo progress information from the core to a restart file to assist with the eventual resuming of the tattooing process. The passive safety of the actuator may allow the client to remove themselves from the tattoo machine when the actuator is unpowered. The resume function of the tattoo in case of an emergency stop is similar to the one for a stop.

The restart data and/or files for the emergency stop and standard stop may be transferred to the cloud or to a detachable storage media and may be used in another machine altogether. This may allow completion on another machine, for example, in case of critical failure of the machine or if the client wishes to complete their tattoo at another location/store/shop. The restart data and/or file may contain the original tattoo file, the ID of the machine that performed the work, diagnostics of the machine at the time of tattoo, ID of tattooed or tested dot in the design and ID of remaining dots, the dot parameter table for the tattoo, the raw data files collected by the sensors and machine vision systems and all other data generated in the original session. Other information in the restart file may include identifying the tattoo session and client information as well as other information input by the operator.

The tattoo systems may also encompass recovery methods in the case of machine malfunction. Based on the gravity of the machine malfunction, a warning or a pause or a stop or an emergency stop may be initiated by the operator, automatically by the machine or by the client.

External malfunction may include loss of reliable power, such as during a power outage. One embodiment of the invention includes an uninterruptible power supply (UPS) which allows providing power in case of outage, at least long enough to complete the ongoing tattoo. In case the tattoo is not finished within the predicted battery life of the UPS, the operator or machine itself may trigger the stop function of the equipment.

The automated tattoo machine includes automated and manual diagnostic function that evaluates if the device is operating nominally. As part of this disclosure, we present some of the diagnostic function for critical system. This is not construed as exhaustive and it shall be assumed that each subsystem has its own operational diagnostic function to verify nominal operation.

One potential source of malfunction is a disposable malfunction, in particular a needle malfunction, an electrode malfunction or an ink delivery malfunction.

Needle malfunction may be identified by a change of the galvanic response of the needle when in contact with the skin, a change in the perceived dot quality by the machine vision system, by the operator or the client observation or response or by ink delivery to the skin failure as observed by the machine vision. In case of a needle malfunction, the machine may trigger an error message and pause the machine and/or the operator may trigger a pause. The operator may decide to trigger a stop if a replacement of the needle is warranted. The client is allowed to disengage from the machine while the operator diagnose and address the needle malfunction by issuing a needle replacement. The tattoo process may resume as specified by the stopping process. If the needle cartridge was replaced, dry dots may need to be resumed from the start in order to account from the variability of needle sharpness and length which may affect puncture settings. Note that if dry dots are done a second time, their position with respect to the tattoo may be shifted slightly in order to avoid puncturing the skin at the location of previous punctures as this may shift the measurements.

Electrode malfunctions are identified by the addition of a test electrode or internal circuitry which purpose is to verify resistance of each electrode connection. In case of electrode failure, the process of the tattoo may be paused to replace the electrodes. The or internal circuitry electrode may also be replaced. Electrode contact resistance may be tested at the beginning and throughout the tattoo process to verify operation. A stop may or may not be triggered by the operator depending on whether or not dry punctures need to be reevaluated.

Ink delivery malfunction may be detected when the ink delivery is too close to the capacity of the reservoir, if no ink is observed to exit the needle tip or if the dot on the skin seems to be executed with an inappropriate amount of ink. A pause or stop may be triggered to refill the reservoir, exchange the ink delivery line or replace the needle cartridge. In case of no disruption to the tattoo process, a pause may be sufficient. In case the needle cartridge is replaced, the process specific to needle replacement may be executed.

Detected actuation failure may trigger a pause (for transient failure such as motor overheating), stop, or an emergency stop (for a power or mechanical failure) in order to protect the client. The operator may decide to resume the process at a later time and trigger a maintenance flag for the machine.

In general consideration, any diagnostic error from the machine may trigger a pause, a stop or an emergency stop, which may be addressed by the operator during the tattoo session or by a subsequent maintenance. Corrective action (positive or negative) may be taken in response to any errors, malfunctions, failures, or other adverse events (e.g., excess skin deformation, machine vision errors, etc.), such as, but not limited to, those described throughout this application.

The robotic systems can use a dot database. The number of punctures for a specific ink dot can be referred to in the dot database. This is the number of times the needle will touch and puncture the skin at the same location for the purpose of transferring ink. This number of punctures affects the final size and color intensity of the ink dot. The tattoo device can pilot the number of punctures performed at a certain position to achieve various tattoo dot diameter and for varying the color intensity to achieve various area coverage in the design and for color tone and color gradient with the same ink. The number of punctures at the same location can be varied from 1 to 100 punctures which the system algorithm attributes to different tone, gradient and dot size. Puncture number at a location can be selected to vary gradient, tone and/or dot size. The robotic system can include an ink quality monitor configured to monitor the ink quality based on, for example, ink viscosity, optical characteristics of ink (e.g., color intensity, tone, etc.), or the like. The robotic system can determine the number of punctures at a location based, at least in part, on ink characteristics, such as viscosity, optical characteristics, retention in skin, etc. For example, the number of punctures can be increased or decreased for high color intensity ink or low color intensity ink, respectively.

Tracking and Positioning Technologies

The positioning algorithm disclosed in this patent in relation to FIGS. 5,6,7 is distinguished from previously available tracking-based global positioning algorithms. Tracking-based global positioning methods and algorithms can be used to calculate the relative positioning of a surface of interest with respect to the camera, or vice versa. These methods can operate by (i) collecting a series of images (e.g., images from one or more cameras) of the surface of interest at different times or corresponding to different relative positioning of the camera(s) and the surface, (ii) identification of unique features on the surface of interest, either pre-determined or selected during operation, (iii) tracking the positions of the features on each image over time, and (iv) calculating the relative positioning of the surface of interest with respect to the camera(s), based on the geometric relationships between the positions of tracked features on the camera image. Tracking-based global positioning methods for controlling robotic arms to manipulate objects in 2D or 3D space can be used. Tracking-based global positioning methods can pose certain limitations in their application for automatic tattooing. First, the features should be sufficiently distinct from each other in appearance, to be uniquely identified and tracked across different images. This may limit the number of distinct tracking points which may be placed on the surface (e.g. "surface" being the skin surface in a tattooing application). Second, the precision of the identified locations of the features is typically limited the order of a millimeter, which may prevent use of the technology for high-precision tattooing applications. For example, based on a 10 mega-pixel camera taking images from a distance of 1-2 meters (typical operating space of a robotic arm). These two aspects would limit the resolution, accuracy and precision of tattoos robotically applied on a body part based on a tracking-based global positioning method.

In contrast, a pattern-detection based machine vision method, for example, as described in relation to FIG. 7, may be used to overcome the above limitations and identify the position of a tattooing head, as well as the local deformation of the skin, with a much higher precision (e.g., detected skin position within 10-100 um of actual skin position). The pattern-based method described in FIG. 7 can include approaching the skin surface with a robotic system to capture close-up, high-resolution camera images of a pattern of fiducial markers on the skin. The system can identify the position of the camera relative to the skin by searching for the detected pattern within the entire pattern known prior to actuation. In this method, the machine vision camera (e.g., machine vision camera 131 in FIG. 2, machine vision camera 430 in FIG. 8, etc.) is attached to (and moves with) the tattoo shuttle (e.g., tattoo shuttle 104 in FIG. 2, or tattoo shuttle 404 in FIG. 8), which may be positioned on the body by a gantry system or a robotic arm. The images being analyzed can be close-up, high-resolution images of the surface (a subset of the area being tattooed), which dramatically increases the resolution, accuracy and precision.

Patterns can be analyzed. For example, referring to step 367 of the method in FIG. 7, the position of the tattoo head on the body is identified by matching the partial pattern in the image, to the entire pattern, which is performed by a search algorithm. In some methods, the images do not need to contain the entire tattoo area, which would require a minimum distance to the skin and thus would decrease the resolution of the machine vision-based image analysis and consequently would decrease the spatial accuracy of the tattoo. In some methods, the pattern of fiducials may be either naturally-occurring or synthetically created and applied on the skin, for example, using a stencil (See step 530 in FIG. 9). For example, FIG. 6A shows an image captured by a machine vision camera, which reveals a portion of a pattern. The pattern in this example is produced by omission of stencil dots, while the visible dots inform the local deformation and rotation of the skin (step 366 in FIG. 7). After analysis of fiducials and the pattern they form (See FIG. 6B), the position of the tattoo head is identified (e.g., step 367 of FIG. 7) by searching for the detected portion of the pattern within the entire pattern (See FIG. 5A). The machine vision methods disclosed can eliminates the need to track individually-unique features from a minimum viewing distance, which are at the limiting aspects of tracking-based global positioning methods discussed herein.

In some tattooing methods, tracking techniques are used concurrently or sequentially. Global positioning can be used to analyze and track the position of body part, stenciling, and other identifiable features for developing a tattooing routine. Machine vision methods can then be used to track individual features at the tattoo site while applying ink to the site. In some methods, multiple tracking techniques are used simultaneously for tracking redundancy.

Multi-Stage Tattooing

A multi-stage tattooing process may be performed to achieve multi-spatial tattooing. Each stage can apply portion(s) of the tattoo with specific characteristics. A high-precision stage, for example, can be performed for high spatial precision tattooing (e.g., achieving a spatial accuracy in placement of tattoo dots within 10-50 um of their targeted locations) on generally curved body parts. A low-precision stage, for example, can be performed for rapid tattooing of a relatively large area. An example two-stage process can include (1) global positioning of a tattoo head on the body part, coming in stable contact with the skin, and (2) local positioning and actuation of a tattoo needle with high precision. This method can substantially increase the precision of tattoo execution by moving the burden of positional accuracy from the global positioning stage to the local positioning stage. The first global positioning stage corresponds to the gross spatial positioning of the tattooing head on the body part, which may be curved. The actuation of the tattooing head may be achieved by, for example, a multi-axis robotic arm (e.g., 6-axis robotic arm), a 2 axis or 3 axis gantry system, or a combination of both where the tattooing head is attached to a gantry system through additional actuators, thus allowing rotational and translational movement of the tattooing head. The spatial control of the first stage (i.e., the global positioning stage) to position the tattoo head on a desired part of the body may be performed by a combination of technologies, such as LIDAR-based 3D surface reconstruction, machine vision systems based on tracking reference features on the skin, etc. The precision of a global positioning stage alone may be in the order of a millimeter or more (e.g., 0.5 mm, 1 mm, 2 mm, 3 mm, 4 mm, 5 mm, etc.) due to (i) vibration-based and actuation-based limitations of a robotic arm, and (ii) optical limitations of a machine vision camera placed at a distance. Such systems may be unable to achieve high spatial accuracy and resolution in tattoo execution (e.g., tattoo dots, tattoo lines or other design features applied within 1-50 μm, 10-100 μm, 20-150 μm, etc. of their targeted locations).

The multi-stage process enables the desired accuracy, precision, and/or resolution in the second stage (i.e., the local positioning stage), which starts after the tattooing head comes into contact with the skin. The presence of one or more machine vision devices attached to the tattooing head can provide target spatial precision, including high spatial precision. For example, the machine vision technology described in connection to FIGS. 5A, 5B, 6A, 6B, and 7 may be used in a second or high-precision stage, to (i) identify the precise position of the tattooing head on the skin, (ii) identify the local deformation and rotation of the skin under the tattooing head with high precision, (iii) map the coordinates of dots on the tattoo design onto their corresponding coordinates on the skin, and (iv) accordingly position the tattoo needle on the skin surface to execute the tattoo dots with high spatial accuracy and precision. The desirable accuracy of the two-stage or multi-stage process results from performing the machine vision analysis and the subsequent control of the tattoo needle, only after the tattooing head comes into contact with the skin. For example, such contact may be achieved by the contactors or contactor systems disclosed herein.

Pain Management

The system disclosed herein can be used to manage pain by using one or more pain inhibitors. The pain inhibitors can include one or more analgesic elements configured to cool tissue an effective amount to inhibit, limit, or substantially prevent pain. Analgesic elements can be, for example, Peltier devices, thermoelectric cooling elements, cryo-elements capable of applying cryogenic or cooled fluids to control the temperature of tissue being tattooed via conduction, convection, or combinations thereof. For example, tissue can be cooled to or below an analgesic temperature such that the temperature of the tissue remains cooled during piercing. The analgesic effect can minimize, limit, or substantially prevent pain felt by the client during the injection process or portion thereof. The tattoo or inking head or another component can include or carry analgesic elements configured to produce an analgesic effect without thermally damaging the tissue.

In some procedures, tissue can be cooled to a temperature equal to or lower than an analgesic temperature at which nerve tissue is at least partially numbed to block temperature-induced pain signals from being perceived by the brain. Additionally, the system can control the temperature of the targeted tissue to prevent or control tissue freezing to prevent unwanted freezing pain and/or injury. Without being bound by theory, cooling of the epidermal and dermal tissue can create a conduction block in epidermal, dermal and sub-dermal sensory nerve fibers innervating these tissues, thereby providing an analgesic effect. In addition to the blocking or reduction of nerve conduction sensory nerve fibers for prevention and/or reduction of acute somatic pain perception, local cold exposure may also reduce post-puncture swelling, inflammation, and bleeding, through vasoconstriction, and thereby reduce pain and fear associated with the tattooing process. In some embodiments, cooling can be used post injection to inhibit, limit, or substantially prevent unwanted side effects (e.g., swelling, inflammation, pain, etc.).

The cooling can create temporary or reversible conduction blocks in sensory nerve fibers innervating tissue, thereby providing the analgesic effect. In one procedure, a target area or site can be rapidly numbed in less than about 5 seconds, 10 seconds, 1 minute, 5 minutes, 10 minutes, 20 minutes, 60 minutes, 90 minutes, or other desired cooling period. The analgesic elements or cooled fluid (e.g., blown air, flowing liquid, etc.) can be at a temperature within a range of about −20° Celsius to about 5° Celsius, about −15° Celsius to about 5° Celsius, or about −5° Celsius to about 2° Celsius, or other suitable temperature ranges for achieving desired analgesic effect. In some embodiments, cooling rates of the skin surface or targeted tissue can be equal to or greater than about 0.01° C./minute, 0.1° C./minute, 1° C./minute, 5° C./minute, or other desired cooling rates selected based on, for example, client comfort. The target area tissue can be at a temperature less than 0° Celsius, 5° Celsius, 10° Celsius, 15° Celsius, or other suitable temperature when punctured. The target temperature can be selected based on the number of injection sites to be tattooed within a period of time and desired analgesic effect. A controller or tattooing module can be programmed to cause the system to cool tissue from normal temperature to a cooled temperature to anesthetize the bulk tissue at the target area or site. For example, the target tissue can be cooled to a temperature equal to or lower than about 0° C., 1° C., 2° C., 3° C., 4° C., 5° C., 6° C., 7° C., 8° C., 9° C., 10° C. or 15° C. The skin can be monitored using one or more temperature sensors, optical sensors, or freeze detect sensors to avoid and/or counteract adverse cooling events, such as tissue freezing.

CONCLUSION

The construction and arrangement of the elements of the systems and methods as shown in the embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. It should be noted that the elements and/or assemblies of the apparatus may be constructed from any of a wide variety of materials that provide sufficient strength or durability to, for example, repeatedly apply tattoos. Any embodiment or design described herein is not necessarily to be construed as preferred or advantageous over other embodiments or designs. Accordingly, all such modifications are intended to be included within the scope of the present inventions. The order or sequence of any process or method steps, including the steps discussed in connection with the algorithms discussed herein may be varied or re-sequenced according to alternative embodiments. Other substitutions, modifications, changes, and omissions may be made in the design, operating conditions, and arrangement of the embodiments without departing from scope of the present disclosure or from the spirit of the appended claims. For example, the techniques disclosed herein can be used to tattoo different articles, including articles made of natural materials, synthetic materials, or the like.

The present disclosure contemplates systems and methods which may be implemented or controlled by one or more controllers to perform the actions as described in the disclosure. For example, in some embodiments, the controller, whether part of a tattooing apparatus or a separate controller, may be configured to process the measured data from the sensors, perform the recording, appending, or storing of the data (e.g., puncture data, ink data, needle data, skin data, etc.) and/or any calculated values within the different tables or maps described, perform all described and any similarly suitable algorithms, and control operation of any disclosed parts or components in a manner necessary or appropriate for proper function, operation, and/or performance of any disclosed systems or methods. For example, the controllers (e.g., controller 108, controller 109, etc.) can store data and calculate values based on the stored data.

The controllers can include machine-readable media and one or more processors, Programmable Logic Controllers, Distributed Control Systems, secure processors, memory, and the like. Secure storage may also be implemented as a secure flash memory, secure serial EEPROM, secure field programmable gate array, or secure application-specific integrated circuit. Processors can be standard central processing units or secure processors. Secure processors can be special-purpose processors (e.g., reduced instruction set processors) that can withstand sophisticated attacks that attempt to extract data or programming logic. A secure processor may not have debugging pins that enable an external debugger to monitor the secure processor's execution or registers. In other embodiments, the system may employ a secure field programmable gate array, a smartcard, or other secure devices. Other types of computing devices can also be used.

Memory can include memory, such as standard memory, secure memory, or a combination of both memory types. By employing a secure processor and/or secure memory, the system can ensure that both data and instructions are highly secure. Memory can be incorporated into the other components of the controller system and can store computer-executable or processor-executable instructions, including routines executed by a programmable computing device. In some embodiments, the memory can store programs for preset configurations. Stored programs (e.g., tattooing programs, calibration programs, graphic mapping programs, etc.) can be modified by a subject, operator, or tattoo artist to provide flexibility. Tattooing programs can be configured for tattooing animals, articles, goods, or the like. For example, some tattooing programs can be for tattooing animals (e.g., living humans or farm animals) and other tattooing programs can be for tattooing articles (e.g., purses, footwear, clothing, automobile seats, etc.).

Controllers can be in communication with the components of the tattooing apparatus via, for example, a direct wired connection, a wireless connection, or a network connection. The controller 108 of FIG. 1B, for example, can be a handheld electronic device, such as a tablet, smart phone, or the like, and it can include digital electronic circuitry, firmware, hardware, memory, a computer storage medium, a computer program, processor(s) (including programmed processors), or the like. In other embodiments, the controller 108 is a computer (e.g., a tower, a desktop, or a laptop) connected to the apparatus 100 via a wired or wireless connection. The controller 108, or the controller 109, can be used to modify stencils, as discussed in connection with FIG. 3A. The controller 109 (illustrated schematically in FIG. 1B) can include input element in the form of buttons or a touch screen for individually controlling the apparatus. In one embodiment, controllers 108 and 109 can include a user interface for inputting, modifying, and/or controlling any system component or process step described in this disclosure.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures, and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

The headings provided herein are for convenience only and are not intended to limit or interpret the scope or meaning of the technology. Although the figures may show a specific order of method steps, the order of the steps may differ from what is depicted. Also, two or more steps may be performed concurrently or with partial concurrence. All such variations are within the scope of the disclosure. Likewise, software implementations could be accomplished with standard programming techniques with rule based logic and other logic to accomplish the various measuring steps, calculating steps, storing steps, calibrating steps, and any other steps for proper coordination and operation of the systems and methods described above. Aspects of the described technology can be modified, if necessary, to employ the systems, functions, and concepts of the various references described above to provide yet further embodiments. For purposes of this disclosure, the terms customer and subject are interchangeable. Tattoos can be applied to animals (e.g., skin of mammals, including humans, pigs, cattle, farm animals, etc.), articles, natural materials (e.g., leather), synthetic materials, or other tattooable items. For example, tattoos can be applied to leather goods (e.g., belts, wallets, backpacks, etc.) using the systems, tattoo apparatus, and methods disclosed herein. In one embodiment, the tattooing system 90 of FIG. 1B can be configured to tattoo a leather boot, bag, or other article, for example. While the above description details certain embodiments and describes the best mode contemplated, no matter how detailed, various changes can be made. Implementation details may vary considerably, while still being encompassed by the technology disclosed herein. The various aspects and embodiments disclosed herein are for purposes of illustration and are not intended to be limiting, with the true scope and spirit being indicated by the following claims.

What is claimed is:

1. A tattoo device comprising:
    at least one sensor configured to detect at least one characteristic of a portion of skin;

a needle assembly including a tattoo needle and a needle motor which oscillates the needle;

an actuator assembly coupled to the needle assembly and including a first actuator configured to move the needle assembly relative to the skin to control a piercing depth of the tattoo needle, and a second actuator configured to control number of punctures per tattoo dot by engaging and disengaging the tattoo needle with the skin during oscillations; and a controller in communication with the at least one sensor and the actuator assembly, wherein the controller is programmed to:

determine a piercing depth and a number of needle punctures for a tattoo dot based at least in part on the detected at least one characteristic of the portion of skin, and command the first actuator to position the needle assembly such that the tattoo needle extends to the determined piercing depth and to command the second actuator to position the tattoo needle such that the tattoo needle, which is being oscillated by the needle motor, punctures the skin for the determined number of needle punctures to apply ink to form the tattoo dot.

2. The tattoo device of claim 1, further comprising a positioning assembly configured to move the needle assembly, wherein the controller is programmed to command the positioning assembly to move the needle assembly to robotically apply tattoo dots to form a tattoo, the first actuator includes a stepper motor operable to move the needle assembly relative to the skin to set a maximum needle extension, and the second actuator includes a solenoid actuator operable to engage and disengage the needle with the skin during oscillations.

3. The tattoo device of claim 1, wherein the controller is further programmed to cause the second actuator to move the needle assembly toward the skin upon initiation of the determined number of needle punctures and to move the needle assembly away from the skin upon completion of the determined number of needle punctures, and wherein the tattoo needle includes a plurality of ink delivery needles coupled together.

4. The tattoo device of claim 1, wherein the at least one characteristic of the portion of skin includes at least one of a skin elasticity, impedance, or thickness.

5. The tattoo device of claim 1, wherein the at least one characteristic of the portion of skin includes one or more of the following:

at least one of a skin elasticity, impedance, or thickness of an epidermal layer of the skin, at least one of a skin elasticity, impedance, or thickness of a dermal layer of the skin, and/or at least one of a skin elasticity, impedance, or thickness of multiple layers of the skin.

6. The tattoo device of claim 1, wherein the at least one sensor is configured to detect a depth of a tattoo needle at a puncture event based at least in part on a relationship between a contact impedance variation of the tattoo needle puncturing the skin and the depth of the tattoo needle in the skin.

7. The tattoo device of claim 1, wherein the controller is programmed to receive output from the at least one sensor indicative of the detected at least one characteristic of the portion of skin, and determine a skin puncture event based on the received output for controlling tattooing of the skin.

8. The tattoo device of claim 7, wherein the skin puncture event is an initial contact of a tattoo needle with the skin based on the received output.

9. The tattoo device of claim 7, wherein the skin puncture event is an epidermis puncture initiation.

10. The tattoo device of claim 7, wherein the skin puncture event has a maximum depth reached by a tattoo needle in an epidermal layer.

11. The tattoo device of claim 7, wherein the skin puncture event reaches a junction between an epidermal and a dermal layer of the skin.

12. The tattoo device of claim 7, wherein the skin puncture event reaches a junction between a dermal and a hypodermal layer of the skin.

13. A tattoo device comprising:

at least one sensor configured to detect at least one characteristic of a portion of skin;

a needle assembly including a tattoo needle and a needle motor, wherein the needle motor is configured to oscillate the tattoo needle;

an actuator assembly including a first actuator configured to move the needle assembly relative to the skin to control a piercing depth of the tattoo needle, and a second actuator configured to control a number of punctures per tattoo dot by the tattoo needle being oscillated by the needle motor; and a controller in communication with the at least one sensor and the actuator assembly, wherein the controller is programmed to determine a piercing depth and a number of punctures for a respective tattoo dot based at least in part on the detected characteristic of the portion of skin, and command the first actuator to position the needle assembly to position the tattoo needle, when extended, to the determined piercing depth and to command the second actuator to move the needle assembly such that the tattoo needle punctures the skin for the determined number of punctures to apply the respective tattoo dot.

14. The tattoo device of claim 13, further comprising a positioning assembly configured to move the tattoo needle, wherein the controller is programmed to receive tattoo data for a tattoo and command the positioning assembly to move tattoo needle based on the tattoo data to robotically apply the tattoo.

15. The tattoo device of claim 13, wherein the controller is further programmed to cause the second actuator to move the tattoo needle assembly toward the skin upon initiation of the determined number of needle punctures and away from the skin upon completion of the determined number of punctures.

16. The tattoo device of claim 13, wherein the at least one characteristic of the portion of skin includes at least one of a skin elasticity, impedance, or thickness.

17. The tattoo device of claim 13, wherein the at least one characteristic of the portion of skin includes:

at least one of a skin elasticity, impedance, or thickness of an epidermal layer of the skin, at least one of a skin elasticity, impedance, or thickness of a dermal layer of the skin, and/or at least one of a skin elasticity, impedance, or thickness of multiple layers of the skin.

18. The tattoo device of claim 13, wherein the controller is further programmed to receive output from the at least one sensor indicative of the detected at least one characteristic of the portion of skin, and identify a skin puncture event based on the received output.

19. The tattoo device of claim 18, wherein the skin puncture event is an initial contact of a needle with the skin based on the output.

20. The tattoo device of claim 18, wherein the skin puncture event is an epidermis puncture initiation.

21. The tattoo device of claim 18, wherein the skin puncture event is has maximum depth reached by a needle in an epidermal layer.

22. The tattoo device of claim 18, wherein the skin puncture event reaches a junction between an epidermal and a dermal layer of the skin.

23. The tattoo device of claim 18, wherein the skin puncture event reaches a junction between a dermal and a hypodermal layer of the skin.

24. A method for robotic tattooing, comprising:

measuring with at least one sensor at least one characteristic of a portion of skin corresponding to a dot position;

controlling a piercing depth of at least one needle tip for the dot position based at least in part on the at least one characteristic of the portion of skin measured when the at least one needle tip pierces the skin; and depositing pigment from the at least one needle tip at the dot position.

25. The method of claim 24, wherein the dot position is one of a plurality of dot positions, and the method is repeated for each dot position of the plurality of dot positions.

26. The method of claim 24, wherein the dot position is one of a plurality of dot positions, and the measuring step is repeated for some of the plurality of dot positions, and wherein the at least one characteristic of a portion of skin for the remainder of the plurality of dot positions is determined based at least on interpolation from the at least one characteristic of the portion of skin of the measured dot positions.

27. The method of claim 24, wherein the at least one characteristic of the portion of skin includes at least one of a skin elasticity, impedance, or thickness.

28. The method of claim 24, further comprising detecting a depth of the at least one needle corresponding to a puncture event based at least in part on a relationship between (1) a contact impedance of the at least one needle puncturing the skin and (2) the depth of the at least one needle in the skin.

* * * * *